United States Patent
Kubota et al.

(10) Patent No.: US 7,241,606 B2
(45) Date of Patent: Jul. 10, 2007

(54) α-ISOMALTOSYLGLUCOSACCHARIDE SYNTHASE, PROCESS FOR PRODUCING THE SAME AND USE THEREOF

(75) Inventors: Michio Kubota, Okayama (JP); Keiji Tsusaki, Okayama (JP); Takanobu Higashiyama, Okayama (JP); Shigeharu Fukuda, Okayama (JP); Toshio Miyake, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 0 days.

(21) Appl. No.: 10/089,549

(22) PCT Filed: Jul. 25, 2001

(86) PCT No.: PCT/JP01/06412

§ 371 (c)(1),
(2), (4) Date: Apr. 1, 2002

(87) PCT Pub. No.: WO02/10361

PCT Pub. Date: Feb. 7, 2002

(65) Prior Publication Data

US 2003/0194762 A1    Oct. 16, 2003

(30) Foreign Application Priority Data

Aug. 1, 2000 (JP) .............................. 2000-233364
Aug. 2, 2000 (JP) .............................. 2000-234937

(51) Int. Cl.
*C12N 9/10* (2006.01)
(52) U.S. Cl. .............................. 435/193; 435/4; 435/6; 435/69.1; 435/183; 435/252.3; 435/252.5; 435/320.1; 536/23.2
(58) Field of Classification Search .................... 435/4, 435/6, 41, 69.1, 183, 193, 194, 200–210, 435/252.3, 320.1, 243, 252.31; 536/23.2–23.7
See application file for complete search history.

(56) References Cited

U.S. PATENT DOCUMENTS

| 4,521,252 A | 6/1985 | Miyake et al. |
| RE33,047 E | 9/1989 | Miyake et al. |
| 5,786,196 A | 7/1998 | Cote et al. |
| 5,888,776 A | 3/1999 | Cote et al. |
| 5,889,179 A | 3/1999 | Cote et al. |

FOREIGN PATENT DOCUMENTS

| EP | 0 606 753 A2 | 12/1993 |
| EP | 0 628 630 A2 | 6/1994 |
| JP | 58-23799 A | 2/1983 |
| JP | 58-72598 A | 4/1983 |
| WO | WO 01/90338 A1 | 11/2001 |

OTHER PUBLICATIONS

Kim, Yeon-Kye, et al "Enzymatic Preparation of Novel Non-reducing Oligosaccharides Having an Isomaltosyl Residue by Using the transfer Action of Isomaltodextranase from *Arthrobacter globiformis* T6", Biosci. Biotech. Biochem., 1995. 59(7):1367-1369.

Wychoff, H.A., et al, "Isolation and Characterization of Microorganisms with Alternan Hydrolytic Activity", Current Microbiology. 1996. 32:343-348.

Kow-Jen Duan et al "Transglucosylation of a Fungal α-Glucosidase: The Enzyme Properties and Crrelation of Isomaltooligosaccharide Production" Annals New York Academy of Sciences 1995 p. 325-328.

Nishimoto Tomoyuki "The Current Study of Cyclo-tetrasaccharide Focused on the Synthesizing System from Starch" Trends in Glycoscience and Glycotechnology, vol. 14, No. 80, Nov. 2002 p. 323.

Yeon-Kye Kim et al "Enzymatic Preparation of Novel Non-reducing Oligosaccharides Having an Isomaltosyl Residue by Using the Transfer Action of Isomaltodextranase from *Arthrobacter globiformis* T6" Bioscience, Biotechnology and Biochemistry vol. 59, No. 7, 1995 pp. 1367-1369.

*Primary Examiner*—Manjunath Rao
(74) *Attorney, Agent, or Firm*—Browdy and Neimark, PLLC

(57) ABSTRACT

The object of the present invention is to provide an α-isomaltosylglucosaccharide-forming enzyme, process of the same, cyclotetrasaccharide, and saccharide composition comprising the saccharide which are obtainable by using the enzyme; and is solved by establishing an α-isomaltosylglucosaccharide-forming enzyme which forms a saccharide, having a glucose polymerization degree of at least three and having both the α-1,6 glucosidic linkage as a linkage at the non-reducing end and the α-1,4 glucosidic linkage other than the linkage at the non-reducing end, by catalyzing the α-glucosyl-transfer from a saccharide having a glucose polymerization degree of at least two and having the α-1,4 glucosidic linkage as a linkage at the non-reducing end without substantially increasing the reducing power; α-isomaltosyl-transferring method using the enzyme; method for forming α-isomaltosylglucosaccharide; process for producing a cyclotetrasaccharide having the structure of cyclo{→6)-α-D-glucopyranosyl-(1→3)-α-D-glucopyranosyl-(1→6)-α-D-glucopyranosyl-(1→3)-α-D-glucopyranosyl-(1→} using both the α-isomaltosylglucosaccharide-forming enzyme and the α-isomaltosyl-transferring enzyme; and the uses of the saccharides obtainable therewith.

3 Claims, 33 Drawing Sheets

US 7,241,606 B2

α-ISOMALTOSYLGLUCOSACCHARIDE SYNTHASE, PROCESS FOR PRODUCING THE SAME AND USE THEREOF

TECHNICAL FIELD

The present invention relates to a novel α-isomaltosylglucosaccharide-forming enzyme, process and uses of the same, more particularly, to a novel α-isomaltosylglucosaccharide-forming enzyme, process for producing the enzyme, α-glucosyl-transferring method using the enzyme, process for producing a cyclotetrasaccharide having the structure of cyclo{→6)-α-D-glucopyranosyl-(1→3)-α-D-glucopyranosyl-(1→6)-α-D-glucopyranosyl-(1→3)-α-D-glucopyranosyl-(1→} using both the enzyme and an α-isomaltosyl-transferring enzyme, and compositions comprising these saccharides.

BACKGROUND ART

There have been known saccharides composed of glucose molecules as constituent saccharides, for example, partial starch hydrolysates, produced from starches as materials, including amylose, amylodextrin, maltodextrin, maltooligosaccharide, and isomaltooligosaccharide. Also, these saccharides are known to have usually reducing and non-reducing groups at. their molecular ends and exhibit reducibility. In general, partial starch hydrolysates can be expressed with an index of dextrose equivalent (DE), a scale of reducing power based on the dry solid. Those with a relatively high DE value are usually known to have properties of a relatively low molecular weight, relatively low viscosity, strong sweetness and reactivity, easy reactivity with amino group-containing substances such as amino acids and proteins that may induce browning and unpleasant smell, and easily cause deterioration. To improve these defects, there has long been desired a method for lowering or eliminating the reducing power without altering glucose molecules as constituent saccharides of partial starch hydrolysates. For example, as disclosed in *Journal of American Chemical Society*, Vol. 71, pp. 353–358 (1949), it was reported that a method for forming α-, β-, and γ-cyclodextrins that are composed of 6–8 glucose molecules linked together via the α-1,4 glucosidic linkage by contacting amylases, derived from microorganisms of the species *Bacillus macerans*, with starches. Nowadays, these cyclodextrins are produced on an industrial scale and used in diversified fields using their inherent properties such as non-reducibility, tasteless, and enclosing ability. As disclosed, for example, in Japanese Patent Kokai Nos. 143,876/95 and 213,283/95 applied for by the same applicant as the present invention, it is known a method for producing trehalose, composed of two glucose molecules linked together via the α,α-linkage, by contacting a non-reducing saccharide-forming enzyme and a trehalose-releasing enzyme with partial starch hydrolysates such as maltooligosaccharide. At present, trehalose has been industrially produced from starches and used in different fields by using its advantageous non-reducibility, mild- and high quality-sweetness. As described above, trehalose having a glucose polymerization degree (DP) of two, and α-, β-, and γ-cyclodextrins having a DP of 6–8 are produced on an industrial scale and used in view of their advantageous properties, however, the types of non- or low-reducing saccharides are limited, so that more diversified saccharides other than these saccharides are greatly required.

Recently, a new type of cyclotetrasaccharide, composed of glucose units, was reported. *European Journal of Biochemistry*, Vol. 226, pp. 641–648 (1994) shows that a cyclic tetrasaccharide having the structure of cyclo{→6)-α-D-glucopyranosyl-(1→3)-α-D-glucopyranosyl-(1→6)-α-D-glucopyranosyl-(1→3)-α-D-glucopyranosyl-(1→} (may be called "cyclotetrasaccharide" throughout the specification) is formed by contacting a hydrolyzing enzyme, alternanase, with alternan linked with glucose molecules via the alternating α-1,3 and α-1,6 bonds, followed by crystallization in the presence of methanol as an organic solvent.

Cyclotetrasaccharide or a non-reducing saccharide having a cyclic structure, exhibits an inclusion ability to stabilize volatile organic compounds, and does not cause an amino carbonyl reaction, and therefore it is expected to be used and processed with lesser fear of browning and deterioration.

However, the material alternan and alternanase, which are needed for producing the saccharide, are not easily obtainable, and the microorganisms for their production are not easily available.

Under such conditions, the present inventors succeeded in producing cyclotetrasaccharide by contacting, as a material, a saccharide having the α-1,6 glucosidic linkage as a linkage of non-reducing end and having a glucose polymerization degree of at least three (may be called "α-isomaltosylglucosaccharide" throughout the specification) with an α-isomaltosyl-transferring enzyme which specifically hydrolyzes the α-isomaltosyl moiety and the resting glucosylsaccharide moiety and then transfers the α-isomaltosyl moiety to its acceptor to form cyclotetrasaccharide, as disclosed in Japanese Patent Application Nos. 149,484/2000 and 229,557/2000. The α-isomaltosyl-transferring enzyme is an enzyme which forms cyclotetrasaccharide from α-isomaltoglucosaccharide by α-isomaltosyl-transferring reaction and has the following physicochemical properties:

(1) Action

Forming cyclotetrasaccharide having the structure of cyclo{→6)-α-D-glucopyranosyl-(1→3)-α-D-glucopyranosyl-(1→6)-α-D-glucopyranosyl-(1→3)-α-D-glucopyranosyl-(1→} from a saccharide having a glucose polymerization degree of at least three and having both the α-1,6 glucosidic linkage as a linkage at the non-reducing end and the α-1,4 glucosidic linkage other than the above linkage;

(2) Molecular Weight

Having a molecular weight of about 82,000 to about 136,000 daltons when determined on sodium dodecyl sulfate (SDS) polyacrylamide gel electrophoresis (PAGE);

(3) Isoelectric Point (pI)

Having a pI of about 3.7 to about 8.3 when determined on isoelectrophoresis using ampholine;

(4) Optimum Temperature

Having an optimum temperature of about 45° C. to about 50° C. when incubated at a pH of 6.0 for 30 min;

(5) Optimum pH

Having an optimum pH of about 5.5 to about 6.5 when incubated at 35° C. for 30 min;

(6) Thermal Stability

Having a thermostable range at temperatures of about 45° C. or lower when incubated at a pH of 6.0 for 60 min; and (7) pH Stability Having a stable pH range at about 3.6 to about 10.0 when incubated at 4° C. for 24 hours.

Referring to the material saccharides for cyclotetrasaccharide, it should desirably be produced from the abundant and low-cost starches, however, since α-isomaltosyl-transferring enzyme does not directly act on starches, the following procedure is actually employed: Starches are first converted into such an α-isomaltosylglucosaccharide having the above specified structure, for example, relatively-low molecular weight isomaltooligosaccharides such as panose and isomaltosylmaltose, and then subjected to the action of α-isomaltosyl-transferring enzyme to form cyclotetrasaccharide.

It was found that, when used panose as a material for cyclotetrasaccharide, the yield of the saccharide from the material is about 44% to the material, based on the weight of the dry solid (d.s.b.). Similarly, in the case of using isomaltosylmaltose as a material, the yield of cyclotetrasaccharide is about 31%, d.s.b., while in the case of using starches as a material, they should be contacted with enzymes such as α-amylase, starch debranching enzyme, β-amylase, and α-glucosidase to form relatively-low molecular weight isomaltooligosaccharides including panose, and the yield of cyclotetrasaccharide is quite as low as about 15%, d.s.b.

Although the actual production of cyclotetrasaccharide is feasible from starches even with such a low yield, the production cost may be increased. Under these circumstances, it is desired to establish a novel method for producing cyclotetrasaccharide in a relatively high yield using easily available materials such as starches.

DISCLOSURE OF INVENTION

The object of the present invention is to provide an α-isomaltosylglucosaccharide-forming enzyme, process of the same, cyclotetrasaccharide obtainable therewith, saccharides comprising cyclotetrasaccharide, and uses thereof.

To solve the above object, the present inventors widely screened microorganisms, which produce a novel enzyme usable for preparing cyclotetrasaccharide from starches as a material in a relatively high yield, with an expectation of obtaining such an enzyme. As a result, they unexpectedly found that the microorganisms of the genus *Bacillus* or *Arthrobacter* such as *Bacillus globisporus* C9 strain, *Bacillus globisporus* C11 strain, *Bacillus globisporus* N75 strain, and *Arthrobacter globiformis* A19 (hereinafter may be called "Strain C9", "Strain C11", "Strain N75", and "Strain A19"), which were isolated from soils, that form both an α-isomaltosyl-transferring enzyme, as disclosed in Japanese Patent Application Nos. 149,484/2000 and 229,557/2000, and a novel α-isomaltosylglucosaccharide-forming enzyme, which has been pursued by the present inventors. The present inventors accomplished this invention by firstly finding the fact that the yield of cyclotetrasaccharide, aimed at by the present inventors, can be greatly improved by contacting relatively-low molecular weight glucosyl saccharides which include partial starch hydrolysates with α-isomaltosylglucosaccharide-forming enzyme and α-isomaltosyl-transferring enzyme; revealed the properties of α-isomaltosylglucosaccharide-forming enzyme, and preparation method of α-isomaltosylglucosaccharide-forming enzyme; α-glucosyl-transferring reaction using α-isomaltosylglucosaccharide-forming enzyme, process for producing α-isomaltosylglucosaccharide; cyclotetrasaccharide or saccharide compositions comprising cyclotetrasaccharide, obtainable by using α-isomaltosylglucosaccharide-forming enzyme and α-isomaltosyl-transferring enzyme; and process for producing these saccharides. Also, the present inventors established food products, cosmetics, and pharmaceuticals which comprise cyclotetrasaccharide or saccharide compositions comprising the cyclotetrasaccharide, and thus accomplished this invention.

BEST MODE FOR CARRYING OUT THE INVENTION

Figure 1:
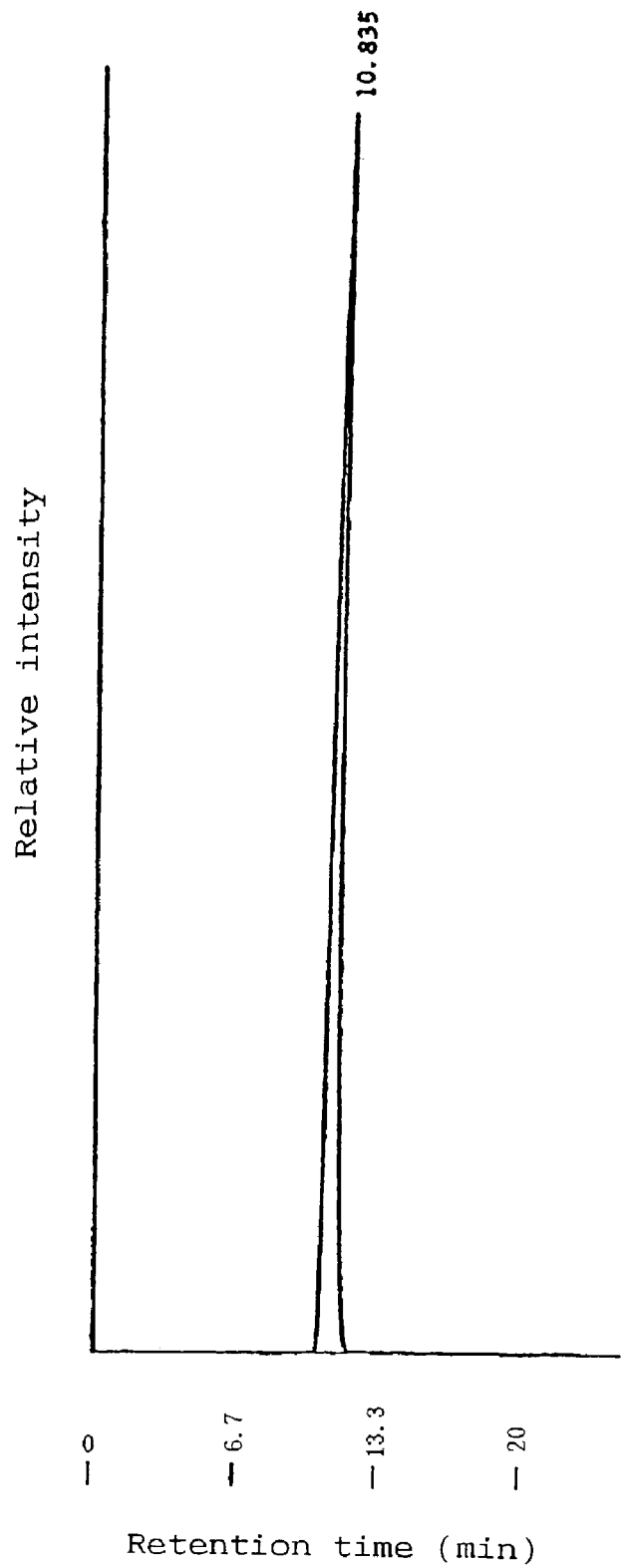
FIG. 1 is an elution pattern of a saccharide, obtained by α-isomaltosyl-transferring enzyme from a microorganism of the species *Bacillus globisporus* C9 strain, when determined on high-performance liquid chromatography.

The following are the identification results of Strain C9, Strain C11, Strain N75, and Strain A19, which produce the novel α-isomaltosylglucosaccharide-forming enzyme of the present invention. The identification tests were conducted in accordance with the methods as described in "*Biseibutsu-no-Bunrui-to-Dotei*" (Classification and Identification of Microorganisms), edited by Takeji Hasegawa, published by Japan Scientific Societies Press, Tokyo, Japan (1985).

<Strain C9>

<A. Morphology>
Characteristics of cells when incubated at 27° C. in nutrient broth agar
Existing usually in a rod shape of 0.5–1.0×1.5–5 μm,
Exhibiting no polymorphism,
Possessing motility,
Forming spherical spores at an intracellular end and swelled sporangia, and
Gram stain, positive;

<B. Cultural Property>
(1) Characteristics of colonies formed when incubated at 27° C. in nutrient broth agar plate;
Shape: Circular colony having a diameter of 1–2 mm after two days incubation
Rim: Entire
Projection: Hemispherical shape
Gloss: Dull
Surface: Smooth
Color: Opaque and pale yellow
(2) Characteristics of colony formed when incubated at 27° C. in nutrient broth agar plate;
Growth: Roughly medium
Shape: Radiative
(3) Characteristics of colony formed when stab cultured at 27° C. in nutrient broth agar plate;
Liquefying the agar plate.

<C. Physiological Properties>
(1) VP-test: Negative
(2) Indole formation: Negative
(3) Gas formation from nitric acid: Positive
(4) Hydrolysis of starch: Positive
(5) Formation of pigment: Forming no soluble pigment
(6) Urease: Positive
(7) Oxidase: Positive
(8) Catalase: Positive
(9) Growth conditions: Growing at a pH of 5.5–9.0 and a temperature of 10–35° C.
(10) Oxygen requirements: Aerobic
(11) Utilization of carbon source and acid formation

| Carbon source | Utilization | Acid formation |
|---|---|---|
| D-Glucose | + | + |
| Glycerol | + | + |
| Sucrose | + | + |
| Lactose | + | + |

Note:
The symbol "+" means yes or positive.

(12) Mol % guanine (G) plus cytosine (C) of DNA: 40%
These bacteriological properties were compared with those of known microorganisms with reference to *Bergey's Manual of Systematic Bacteriology*, Vol. 2 (1986). As a result, it was revealed that the microorganism was identified with a microorganism of the species *Bacillus globisporus*. The microorganism had a feature, not disclosed in any literature, of forming both α-isomaltosylglucosaccharide-forming enzyme, which produces α-isomaltosylglucosaccharide from partial starch hydrolyzates, and α-isomaltosyl-transferring enzyme which produces cyclotetrasaccharide from α-isomaltosylglucosaccharide by transferring α-isomaltosyl residue.

Based on these results, the present inventors named this microorganism "*Bacillus globisporus* C9", and deposited it on Apr. 25, 2000, in International Patent Organism Depositary National Institute of Advanced Industrial Science and Technology Tsukuba Central 6, 1-1, Higashi 1-Chome Tsukuba-shi, Ibaraki-ken, 305–8566, Japan. The deposition of the microorganism was accepted on the same day by the institute under the accession number of FERM BP-7143.

<Strain C11>

<A. Morphology>
Characteristics of cells when incubated at 27° C. in nutrient broth agar
Existing usually in a rod shape of 0.5–1.0×1.5–5 μm,
Exhibiting no polymorphism,
Possessing motility,
Forming spherical spores at an intracellular end and swelled sporangia, and
Gram stain, positive;

<B. Cultural Property>
(1) Characteristics of colonies formed when incubated at 27° C. in nutrient broth agar plate;
Shape: Circular colony having a diameter of 1–2 mm after two days incubation
Rim: Entire
Projection: Hemispherical shape
Gloss: Dull
Surface: Smooth
Color: Opaque and pale yellow
(2) Characteristics of colony formed when incubated at 27° C. in nutrient broth agar plate;
Growth: Roughly medium
Shape: Radiative
(3) Characteristics of colony formed when stab cultured at 27° C. in nutrient broth agar plate;
Liquefying the agar plate <C. Physiological Properties>
(1) VP-test: Negative
(2) Indole formation: Negative
(3) Gas formation from nitric acid: Positive
(4) Hydrolysis of starch: Positive
(5) Formation of pigment: Forming no soluble pigment
(6) Urease: Positive
(7) Oxidase: Positive
(8) Catalase: Positive
(9) Growth conditions: Growing at a pH of 5.5–9.0 and a temperature of 10–35° C.
(10) Oxygen requirements: Aerobic
(11) Utilization of carbon source and acid formation

| Carbon source | Utilization | Acid formation |
|---|---|---|
| D-Glucose | + | + |
| Glycerol | + | + |
| Sucrose | + | + |
| Lactose | + | + |

Note:
The symbol "+" means yes or positive.

(12) Mol % guanine (G) plus cytosine (C) of DNA: 39%
These bacteriological properties were compared with those of known microorganisms with reference to *Bergey's Manual of Systematic Bacteriology*, Vol. 2 (1986). As a result, it was revealed that the microorganism was identified with a microorganism of the species *Bacillus globisporus*.

The microorganism had a feature, not disclosed in any literature, of forming both α-isomaltosylglucosaccharide-forming enzyme, which produces α-isomaltosylglucosaccharide from partial starch hydrolyzates, and α-isomaltosyl-transferring enzyme which produces cyclotetrasaccharide from the α-isomaltosylglucosaccharide by transferring α-isomaltosyl residue.

Based on these results, the present inventors named this microorganism "*Bacillus globisporus* C11 ", and deposited it on Apr. 25, 2000, in International Patent Organism Depositary National Institute of Advanced Industrial Science and Technology Tsukuba Central 6, 1-1, Higashi 1-Chome Tsukuba-shi, Ibaraki-ken, 305–8566, Japan. The deposition of the microorganism was accepted on the same day by the institute under the accession number of FERM BP-7144.

<Strain N75>

<A. Morphology>
Characteristics of cells when incubated at 27° C. in nutrient broth agar
Existing usually in a rod form of 0.5–1.0×1.5–5 μm,
Exhibiting no polymorphism,
Possessing motility,
Forming spherical spores at an intracellular end and swelled sporangia, and
Gram stain, positive;

<B. Cultural Property>
(1) Characteristics of colonies formed when incubated at 27° C. in nutrient broth agar plate;
Shape: Circular colony having a diameter of 1–2 mm after two days incubation
Rim: Entire
Projection: Hemispherical shape
Gloss: Dull
Surface: Smooth
Color: Opaque and pale yellow
(2) Characteristics of colony formed when incubated at 27° C. in nutrient broth agar plate;
Growth: Roughly medium
Shape: Radiative
(3) Characteristics of colony formed when stab cultured at 27° C. in nutrient broth agar plate;
Liquefying the agar plate <C. Physiological Properties>
(1) VP-test: Negative
(2) Indole formation: Negative
(3) Gas formation from nitric acid: Positive
(4) Hydrolysis of starch: Positive
(5) Formation of pigment: Forming no soluble pigment
(6) Urease: Negative
(7) Oxidase: Positive
(8) Catalase: Positive
(9) Growth conditions: Growing at a pH of 5.7–9.0 and a temperature of 10–35° C.
(10) Oxygen requirements: Aerobic
(11) Utilization of carbon source and acid formation

| Carbon source | Utilization | Acid formation |
| --- | --- | --- |
| D-Glucose | + | + |
| Glycerol | + | + |
| Sucrose | + | + |
| Lactose | + | + |

Note:
The symbol "+" means yes or positive.

(12) Mol % guanine (G) plus cytosine (C) of DNA: 40%

These bacteriological properties were compared with those of known microorganisms with reference to *Bergey's Manual of Systematic Bacteriology*, Vol. 2 (1986). As a result, it was revealed that the microorganism was identified with a microorganism of the species *Bacillus globisporus*. The microorganism had a feature, not disclosed in any literature, of forming both α-isomaltosylglucosaccharide-forming enzyme, which produces α-isomaltosylglucosaccharide from partial starch hydrolyzates, and α-isomaltosyl-transferring enzyme which produces cyclotetrasaccharide from the α-isomaltosylglucosaccharide by transferring α-isomaltosyl residue.

Based on these results, the present inventors named this microorganism "*Bacillus globisporus* N75", and deposited it on May 16, 2001, in International Patent Organism Depositary National Institute of Advanced Industrial Science and Technology Tsukuba Central 6, 1-1, Higashi 1-Chome Tsukuba-shi, Ibaraki-ken, 305–8566, Japan. The deposition of the microorganism was accepted on the same day by the institute under the accession number of FERM BP-7591.

<Strain A19>

<A. Morphology>
(1) Characteristics of cells when incubated at 27° C. in nutrient broth agar;
Existing usually in a rod form of 0.4–0.8×1.0–4.0 μm
Exhibiting polymorphism,
Possessing no motility,
Forming no spore, and
Gram stain, positive;
(2) Characteristics of cells when incubated at 27° C. in EYG agar plate;
Exhibiting a growth cycle of bacillus and cocci <B. Cultural Property>
(1) Characteristics of colonies formed when incubated at 27° C. in nutrient broth agar plate;
Shape: Circular colony having a diameter of 2–3 mm after one day incubation
Rim: Entire
Projection: Hemispherical shape
Gloss: Dull
Surface: Smooth
Color: Opaque and pale yellow
(2) Characteristics of colony formed when incubated at 27° C. in nutrient broth agar plate;
Growth: Roughly medium
Shape: Filamentous
(3) Characteristics of colony formed when stab cultured at 27° C. in nutrient broth agar plate;
Not liquefying the agar plate.

<C. Physiological Properties>
(1) Hydrolysis of starch: Negative
(2) Formation of pigment: Forming no soluble pigment
(3) Urease: Positive
(4) Oxidase: Positive
(5) Catalase: Positive (6) Oxygen requirements: Aerobic
(7) Main diamino acid of cell wall: Lysine
(8) Peptidoglycan type of cell wall: Lysine-alanine
(9) N-acyl type of cell wall: Acetyl
(10) Sugar component of cell wall: Galactose, glucose, rhamnose, and mannose
(11) Vitamin requirements: Negative
(12) Mol % guanine (G) plus cytosine (C) of DNA: 62%
(13) DNA-DNA homology: Having a 66.5% of DNA-DNA homology when compared with *Arthrobacter globiformis*, ATCC 8010.

These bacteriological properties were compared with those of known microorganisms with reference to *Bergey's Manual of Systematic Bacteriology*, Vol. 2 (1986). As a result, it was revealed that the microorganism was identified with a microorganism of the species *Bacillus globisporus*. The microorganism had a feature, not disclosed in any literature, of forming both α-isomaltosylglucosaccharide-forming enzyme, which produces α-isomaltosylglucosaccharide from partial starch hydrolyzates, and α-isomaltosyl-transferring enzyme which produces cyclotetrasaccharide from the α-isomaltosylglucosaccharide by transferring α-isomaltosyl residue.

Based on these results, the present inventors named this microorganism "*Arthrobacter globiformis* A19", and deposited it on May 16, 2001, in International Patent Organism Depositary National Institute of Advanced Industrial Science and Technology Tsukuba Central 6, 1-1, Higashi 1-Chome Tsukuba-shi, Ibaraki-ken, 305–8566, Japan. The deposition of the microorganism was accepted on the same day by the institute under the accession number of FERM BP-7590.

In the present invention, any microorganisms of the genera Bacillus, Arthrobacter, and others, as well as their mutants can be appropriately used as long as they form α-isomaltosylglucosaccharide-forming enzyme. These microorganisms can be easily screened by using conventional screening methods for microorganisms with an index of the physicochemical properties of the α-isomaltosylglucosaccharide-forming enzyme of the present invention.

An α-isomaltosyl-transferring enzyme derived from a microorganism of the genus *Arthrobacter* (hereinafter may be called "Strain S1"), isolated by the present inventors from a soil in Okayama-shi, Okayama, Japan, can be advantageously used in the present invention as the α-isomaltosyl-transferring enzyme which produces cyclotetrasaccharide from α-isomaltosylglucosaccharide by transferring α-isomaltosyl residue. The identification tests were conducted in accordance with the methods as described in "*Biseibutsu-no-Bunrui-to-Dotei*" (Classification and Identification of Microorganisms), edited by Takeji Hasegawa, published by Japan Scientific Societies Press, Tokyo, Japan (1985).

<Strain S1>

<A. Morphology>
Characteristics of cells when incubated at 27° C. in nutrient broth agar;
Existing usually in a rod form of 0.3–0.7×0.8–3.5 μm
Exhibiting polymorphism
Possessing no motility
Forming no spore
Gram stain: Positive (2) Characteristics of cells when incubated at 27° C. in EYG agar plate;
Exhibiting a growth cycle of bacillus and cocci <B. Cultural Property>
(1) Characteristics of colonies formed when incubated at 27° C. in nutrient broth agar plate;
Shape: Circular colony having a diameter of 2–3 mm after one day incubation
Rim: Entire
Projection: Hemispherical shape
Gloss: Dull
Surface: Smooth
Color: Opaque and pale yellow
(2) Characteristics of colony formed when incubated at 27° C. in nutrient broth agar plate;
Growth: Roughly medium
Shape: Filamentous
(3) Characteristics of colony formed when stab cultured at 27° C. in nutrient broth agar plate;
Not liquefying the agar plate.

<C. Physiological Properties>
(1) Hydrolysis of starch: Negative
(2) Formation of pigment: Forming no soluble pigment
(3) Urease: Positive
(4) Oxidase: Positive
(5) Catalase: Positive
(6) Oxygen requirements: Aerobic
(7) Main diamino acid of cell wall: Lysine
(8) Peptidoglycan type of cell wall: Lysine-alanine
(9) N-acyl type of cell wall: Acetyl
(10) Sugar component of cell wall: Galactose, glucose, rhamnose, and mannose
(11) Vitamin requirements: Negative
(12) Mol % guanine (G) plus cytosine (C) of DNA: 65%
(13) DNA-DNA homology: Having 84.4% of DNA-DNA homology when compared with *Arthrobacter ramosus*, ATCC 13727.

These bacteriological properties were compared with those of known microorganisms with reference to *Bergey's Manual of Systematic Bacteriology*, Vol. 2 (1986). As a result, it was revealed that the microorganism was identified with a microorganism of the species *Arthrobacter ramosus*. The microorganism had a feature, not disclosed in any literature, forming both α-isomaltosylglucosaccharide-forming enzyme, which produces α-isomaltosylglucosaccharide from partial starch hydrolyzates, and α-isomaltosyl-transferring enzyme which produces cyclotetrasaccharide from the α-isomaltosylglucosaccharide by transferring α-isomaltosyl residue.

Based on these results, the present inventors named this microorganism "*Arthrobacter ramosus* S1", and deposited it on May 16, 2001, in International Patent Organism Depositary National Institute of Advanced Industrial Science and Technology Tsukuba Central 6, 1-1, Higashi 1-Chome Tsukuba-shi, Ibaraki-ken, 305–8566, Japan. The deposition of the microorganism was accepted on the same day by the institute under the accession number of FERM BP-7592.

In the present invention, any mutant of *Arthrobacter ramosus* S1 can be appropriately used in the present invention as long as it forms α-isomaltosylglucosaccharide-forming enzyme. Such a mutant can be easily screened by conventional screening methods for microorganisms with an index of the physicochemical properties of the α-isomaltosyl-transferring enzyme usable the present invention.

Any nutrient culture medium can be used in the invention as long as the above-mentioned microorganisms can grow therein and produce the α-isomaltosylglucosaccharide-forming enzyme; synthetic- and natural-nutrient culture media can be arbitrarily used. The carbon sources usable in the present invention are those which the microorganisms assimilate for their growth: Examples such are starches and phytoglycogen from plants; glycogen and pullulan from animals and microorganisms; saccharides such as glucose, fructose, lactose, sucrose, mannitol, sorbitol, and molasses; and organic acids such as citric acid and succinic acid. The concentrations of these carbon sources in nutrient culture media are appropriately changed depending on their kinds. The nitrogen sources usable in the present invention are, for example, inorganic nitrogen compounds such as ammonium salts and nitrates; and organic nitrogen-containing substances such as urea, corn steep liquor, casein, peptone, yeast extract, and beef extract. The inorganic ingredients usable in the present invention are, for example, calcium salts, magnesium salts, potassium salts, sodium salts, phosphates, and other salts of manganese, zinc, iron, copper, molybdenum, and cobalt. If necessary, amino acids and vitamins can be appropriately used in combination.

The microorganisms used in the present invention are cultured under aerobic conditions at temperatures, usually, in the range of 4–40° C., preferably, 20–37° C.; and at pHs of 4–10, preferably, pHs of 5–9. The cultivation time used in the present invention is set to a time or longer than that required for the growth initiation of the microorganisms, preferably, 10–150 hours. The concentration of dissolved oxygen (DO) in nutrient culture media is not specifically restricted, but usually it is in the range of 0.5–20 ppm and it can be kept within the range by means of controlling the level of aeration, stirring, adding oxygen to air, and increasing the inner pressure of fermentors. The cultivation is freely carried out batchwise or in continuous manner.

After completion of the culture of microorganisms, the enzyme of the present invention is collected. Inasmuch as the activity of the enzyme is found in both cells and cell-free cultures, the latter can be collected as crude enzyme solutions and the intact cultures can be used as crude enzyme solutions. Conventional liquid-solid separation methods can be employed to remove cells from the cultures; methods to centrifuge the cultures, filtrate the cultures with precoat filters, and filter with plane filters or follow fibers can be appropriately used to remove cells from the cultures. As described above, cell-free cultures can be used as crude enzyme solutions, however, they may be concentrated prior to use by salting out using ammonium sulfate, sedimentation using acetone and alcohol, concentration in vacuo, and concentration using plane membranes and hollow fibers.

Cell-free solutions and their concentrates, which contain the enzyme of the present invention, can be used intact or after immobilizing the enzyme using conventional methods. In this case, for example, conjugation methods using ion-exchangers, covalent bonding/adsorption methods using resins and membranes, and inclusion methods using high-molecular weight substances can be appropriately employed.

The enzyme solutions usually contain the α-isomaltosyl-glucosaccharide-forming enzyme of the present invention and α-isomaltosyl-transferring enzyme. If necessary, the α-isomaltosylglucosaccharide-forming enzyme of the present invention can be used after being separated/purified by conventional methods. As an example, an electrophoretically homogenous α-isomaltosylglucosaccharide-forming enzyme according to the present invention can be obtained by salting out to concentrate the enzyme in the cultures, dialyzing the concentrated crude enzyme, purifying the dialyzed solution by sequential chromatographies of anion-exchange column chromatography using a resin of "SEPA-BEADS FP-DA13", affinity chromatography using a gel of "SEPHACRYL HR S-200", hydrophobic chromatography using a gel of "BUTYL-TOYOPEARL 650M", and affinity chromatography using a gel of "SEPHACRYL HR S-200".

The α-isomaltosylglucosaccharide-forming enzyme of the present invention has the characteristic physicochemical properties that it forms, via the α-glucosyl-transfer, a saccharide, which has a glucose polymerization degree of at least three and has both the α-1,6 glucosidic linkage as a linkage at the non-reducing end and the α-1,4 glucosidic linkage other than the above linkage, from a material saccharide which has a glucose polymerization degree of at least two and has the α-1,4 glucosidic linkage as a linkage at the non-reducing end, without substantially increasing the reducing power of the material saccharide; it has no dextran-forming ability; and it is inhibited by EDTA (ethylenediaminetetraacetic acid). More particularly, the enzyme has the physicochemical properties as shown in the below; and the saccharide, which has both a glucose polymerization degree of at least two and the α-1,4 glucosidic linkage as a linkage at the non-reducing end, includes, for example, one or more saccharides selected from maltooligosaccharides, maltodextrins, amylodextrins, amyloses, amylopectins, soluble starches, gelatinized starches, and glycogens:

(1) Action
Forming a saccharide having a glucose polymerization degree of at least three and having both the α-1,6 glucosidic linkage as a linkage at the non-reducing end and the α-1,4 glucosidic linkage other than the above linkage, via the α-glucosyl-transfer from a saccharide having a glucose polymerization degree of at least two and having the α-1,4 glucosidic linkage as a linkage at the non-reducing end, without substantially increasing the reducing power of the material saccharide;

(2) Molecular Weight
Having a molecular weight of about 74,000 to about 160,000 daltons when determined on SDS-PAGE;

(3) Isoelectric Point
Having an isoelectric point of about 3.8 to about 7.8 when determined on isoelectrophoresis using ampholine;

(4) Optimum Temperature
Having an optimum temperature of about 40° C. to about 50° C. when incubated at a pH of 6.0 for 60 min;
Having an optimum temperature of about 45° C. to about 55° C. when incubated at a pH of 6.0 for 60 min in the presence of 1 mM $Ca^{2+}$;
Having an optimum temperature of 60° C. when incubated at a pH of 8.4 for 60 min; or
Having an optimum temperature of 65° C. when incubated at a pH of 8.4 for 60 min in the presence of 1 mM $Ca^{2+}$;

(5) Optimum pH
Having an optimum pH of about 6.0 to about 8.4 when incubated at 35° C. for 60 min;

(6) Thermal Stability
Having a thermostable region at temperatures of about 45° C. or lower when incubated at a pH of 6.0 for 60 min,
Having a thermostable region at temperatures of about 50° C. or lower when incubated at a pH of 6.0 for 60 min in the presence of 1 mM $Ca^{2+}$,
Having a thermostable region at temperatures of about 55° C. or lower when incubated at a pH of 8.0 for 60 min, and Having a thermostable region at temperatures of about 60° C. or lower when incubated at a pH of 8.0 for 60 min in the presence of 1 mM $Ca^{2+}$;

(7) pH Stability

Having a stable pH region at about 4.5 to about 10.0 when incubated at 4° C. for 24 hours; and (8) N-terminal amino acid sequence tyrosine-valine-serine-serine-leucine-glycine-asparagine leucine-isoleucine, SEQ ID NO:1 histidine-valine-serine-alanine-leucine-glycine asparagine-leucine-leucine, SEQ ID NO:11 alanine-proline-leucine-glycine-valine-glutamine -arginine-alanine-glutamine-phenylalanine -glutamine-serine-glycine SEQ ID NO:18

The substrates usable for the α-isomaltosyl-glucosaccharide-forming enzyme of the present invention include polysaccharides having the 1,4-glucosidic linkage such as starches, amylopectins, amyloses, and glycogens; and partial starch hydrolyzates such as amylodextrins, maltodextrins, and maltooligosaccharides obtainable by partially hydrolyzing the above polysaccharides with amylases, acids, etc. These glucosyl saccharides having the α-1,4 glucosidic linkage can be further treated with a branching enzyme (EC 2.4.1.18) such as a branching enzyme for the substrates. Examples of partial starch hydrolyzates of glucosyl saccharides treated with amylases are those which are hydrolyzed with α-amylase (EC 3.2.1.1), β-amylase (EC 3.2.1.2), maltotriose-forming enzyme (EC 3.2.1.116), maltotetraose-forming enzyme (EC 3.2.1.60), maltopentaose-forming enzyme, and maltohexaose-forming amylase (EC 3.2.1.98) as disclosed in "Handbook of Amylases and Related Enzymes", published by Pergamon Press, Tokyo, Japan (1988). In the case of preparing partial starch hydrolyzates, debranching enzymes such as pullulanase (EC 3.2.1.41) and isoamylase (EC 3.2.1.68) can be arbitrarily used.

The starches as the substrates include terrestrial starches from crops such as corns, wheats, and rices; and subterranean starches such as potatoes, sweet potatoes, and tapioca. Preferably, these starches are gelatinized and/or liquefied into a liquid form in use. The lower the degree of partial hydrolysis, the higher the yield of cyclotetrasaccharide becomes, and therefore the DE is set to a level of about 20 or lower, preferably, about 12 or lower, and more preferably, about five or lower.

The acceptors for transferring reaction by the α-isomaltosylglucosaccharide-forming enzyme of the present invention include the above substrates per se, monosaccharides such as glucose, xylose, galactose, fructose, arabinose, fucose, sorbose, and N-acetylglucosamine; oligosaccharides such as trehalose, isomaltose, isomaltotriose, cellobiose, gentibiose, lactose, and sucrose; and others such as maltitol and L-ascorbic acid.

The concentration of substrates is not specifically restricted, and the enzymatic reaction of the present invention proceeds even when used in a low concentration as low as 0.1% (w/w) (throughout the specification, "% (w/w)" is abbreviated as "%" hereinafter, unless specified otherwise). However, one percent or higher concentrations are preferably used for an industrial scale production. The substrate solutions may be those in a suspension form which contain incompletely-dissolved insoluble substrates. The substrate concentration is preferably 40% or lower, and more preferably, 30% or lower.

The temperatures for the enzymatic reaction used in the present invention are those which proceed the enzymatic reaction, i.e., those up to about 65° C., preferably, about 30° C. to about 55° C. The pHs for the enzymatic reaction are usually set to 4.5–10, preferably, about 5.5 to about 9. The time for the enzymatic reaction can be appropriately set depending on the enzymatic reaction efficiency.

By contacting the α-isomaltosylglucosaccharide formed by the above enzymatic reaction with α-isomaltosyl-transferring enzyme, cyclotetrasaccharide is produced in a satisfactorily yield. The α-isomaltosyl-transferring enzyme can be allowed to act on substrates after the action and the inactivation of the α-isomaltosylglucosaccharide-forming enzyme of the present invention. Preferably, these α-isomaltosylglucosaccharide-forming enzyme and α-isomaltosyl-transferring enzyme can be used in combination to facilitate the production of cyclotetrasaccharide from starches or partial hydrolyzates thereof in a high yield of about 30%, d.s.b., or higher, and the production from glycogen in a yield of about 80%, d.s.b., or higher. The formation mechanism of cyclotetrasaccharide by the above combination use can be estimated as follows based on the reaction properties of the two enzymes:

(1) The α-isomaltosylglucosaccharide-forming enzyme of the present invention acts on the α-1,4 glucosyl residue at the non-reducing end of a saccharide, which has a glucose polymerization of at least two and has the α-1,4 glucosidic linkage as a linkage at the non-reducing end, such as starches, glycogen, and partial starch hydrolyzates thereof, to release a glucose residue; and then intermolecularly transfers the released glucose residue to the hydroxyl group at C-6 of the glucose of other saccharide and forms a saccharide having an α-isomaltosyl residue at the non-reducing end;

(2) The α-isomaltosyl-transferring enzyme acts on the saccharide having an α-isomaltosyl residue at the non-reducing end, and then intermolecularly transfers the residue to the hydroxyl group at C-3 of a glucose residue of other saccharide having an α-isomaltosyl residue at the non-reducing end and forms a saccharide having an isomaltosyl-1,3-isomaltosyl residue at the non-reducing end;

(3) The α-isomaltosyl-transferring enzyme acts on the saccharide having an isomaltosyl-1,3-isomaltosyl residue at the non-reducing end to release the isomaltosyl-1,3-isomaltosyl residue from the saccharide by the intermolecular transferring action, and then cyclizes the released isomaltosyl-1,3-isomaltosyl saccharide into cyclotetrasaccharide; and (4) Through the steps (1) to (3), cyclotetrasaccharide is formed from the resulting saccharide with no isomaltosyl-1,3-isomaltosyl residue, and the yield of cyclotetrasaccharide is highly increased by sequentially repeating the steps (1) to (3).

As explained above, it can be estimated that, when used in combination, the α-isomaltosylglucosaccharide-forming enzyme of the present invention and α-isomaltosyl-transferring enzyme repeatedly act on their substrates to increase the yield of cyclotetrasaccharide.

During the cyclotetrasaccharide-forming reaction, optionally, other saccharide-transferring enzyme(s) can be advantageously used in combination to improve the yield of cyclotetrasaccharide; when two types of enzymes, i.e., α-isomaltosylglucosaccharide-forming enzyme and α-isomaltosyl-transferring enzyme are allowed to act, for example, on an about 15% solution of partial starch hydrolyzate, cyclotetrasaccharide is produced in a yield of about 55%, while the use of three types of enzymes, i.e., α-isomaltosylglucosaccharide-forming enzyme, α-isomaltosyl-transferring enzyme, and cyclomaltodextrin glucanotransferase, under the same conditions as above, increases the maximum yield of cyclotetrasaccharide by about 5–10% to an improved yield of about 60–65%.

In the case of forming cyclomaltodextrin, it can be produced by culture methods using microorganisms capable of forming both α-isomaltosylglucosaccharide-forming enzyme and α-isomaltosyl-transferring enzyme which specifically hydrolyzes the linkage between the α-isomaltosyl moiety and the resting glucosylsaccharide moiety of α-isomaltosylglucosaccharide formed by the α-isomaltosylglucosaccharide-forming enzyme, and then transfers the released α-isomaltosyl moiety to an acceptor.

As the culture media used in the above methods using microorganisms, any synthetic or natural media can be used as long as they contain saccharides having a glucose polymerization degree of at least two and having the α-1,4 glucosidic linkage as a linkage at the non-reducing end and in which the microorganisms can grow. As for the other conditions for culturing microorganisms, those which are used to form the α-isomaltosylglucosaccharide-forming enzyme of the present invention can be employed.

The cultures, obtained by the above enzymatic reaction and culture, can be used intact as solutions comprising cyclotetrasaccharide or saccharide compositions of the same. In general, they can be purified before use in such a manner of using one or more of the following purification methods alone or in combination: Decoloration with activated charcoal, desalting by ion-exchange resins in a H or OH form, and column chromatographies such as ion-exchange column chromatography, column chromatography using activated charcoal, and silica gel column chromatography, separation using organic solvents such as alcohols and acetone, membrane separation using adequate separability, hydrolysis of the remaining saccharides using enzymes such as amylases including α-amylase, β-amylase, glucoamylase (EC 3.2.1.3), and α-glucosidase (EC 3.2.1.20), and hydrolysis and removal of the remaining saccharides by fermentation with yeasts or by alkaline treatment.

Particularly, ion-exchange column chromatography is preferably used as an industrial scale production method; column chromatography using strong-acid cation exchange resins as disclosed, for example, in Japanese Patent Kokai Nos. 23,799/83 and 72,598/83. Using the column chromatography, the contaminating saccharides can be removed to advantageously produce cyclotetrasaccharide with an improved content of the objective saccharide or saccharide compositions comprising the same. In this case, any one of fixed-bed, moving bed, and semi-moving bed methods can be appropriately used.

The resulting cyclotetrasaccharide and saccharide compositions comprising the same can be appropriately concentrated into syrupy products, and optionally they can be further dried into powdery products.

To produce cyclotetrasaccharide crystals, for example, high cyclotetrasaccharide content solutions, having a concentration of about 30–90% and a purity of about at least 50% of cyclotetrasaccharide, are placed in a crystallizer optionally in the presence of an organic solvent, and then gradually cooled while stirring in the presence of 0.1–20%, d.s.b., of a seed crystal to the cyclotetrasaccharide at temperatures of 95° C. or lower, preferably, 10–90° C., to obtain massecuites. The methods to collect cyclotetrasaccharide crystals and molasses with such crystals include, for example, conventional methods such as separation, block pulverization, fluidized granulation, and spray drying methods.

The resulting cyclotetrasaccharide according to the present invention is a stable, high-quality, low sweetness, non-reducing white power, and is almost free of browning, smelling, and deterioration of materials even when mixed or processed therewith: The materials are particularly, for example, amino acid-containing substances such as amino acids, oligopeptides, and proteins.

Since cyclotetrasaccharide has an inclusion ability, it effectively inhibits the dispersion and quality deterioration of flavorful components and effective ingredients, and stably retains them. For such a purpose, the combination use of cyclotetrasaccharide and other cyclic saccharide(s) such as cyclodextrins, branched cyclodextrins, cyclodextrans, and cyclofructans can be advantageously used to improve the level of the inclusion ability of cyclotetrasaccharide, if necessary. The above cyclic saccharides such as cyclodextrins usable in the present invention should not be restricted to those with a high purity, and can be advantageously a relatively-low purity of cyclotetrasaccharide such as partial starch hydrolyzates containing a large quantity of maltodextrins and cyclodextrins.

Since cyclotetrasaccharide is not hydrolyzed by amylase and α-glucosidase, it is substantially free of assimilation by the body when orally administered. Also, the saccharide is not substantially assimilated by intestinal microorganisms, and therefore it can be used as an extremely-low caloric water-soluble dietary fiber. Cyclotetrasaccharide can be also used as a sweetener substantially free from causing dental caries because it is scarcely assimilated by dental caries-inducing microorganisms. The saccharide prevents the adhesion and solidification of powdery products. The cyclotetrasaccharide of the present invention per se is a natural sweetener with a satisfactory stability but with no toxicity, harm, and side effect, and because of these it can be advantageously used for tablets and sugar-coated tablets in combination with binders such as pullulan, hydroxyethyl starch, and polyvinylpyrrolidone. Furthermore, cyclotetrasaccharide has properties of osmosis-controlling ability, filler-imparting ability, gloss-imparting ability, moisture-retaining ability, viscosity, crystallization prevention ability for other saccharides, insubstantial fermentability, etc.

Thus, the cyclotetrasaccharide and the saccharide compositions comprising the same of the present invention can be arbitrary used as a sweetener, taste-improving agent, quality-improving agent, stabilizer, preventive of discoloration, excipient, etc., in a variety of compositions such as food products, tobaccos, cigarettes, feeds, pet foods, cosmetics, and pharmaceuticals.

The cyclotetrasaccharide and the saccharide compositions comprising the same of the present invention can be used in combination with one or more other sweeteners, for example, powdered syrup, glucose, isomerized sugar, sucrose, maltose, trehalose, honey, maple sugar, sorbitol, maltitol, dihydrochalcone, stevioside, α-glycosyl stevioside, sweetener of *Momordica grosvenori*, glycyrrhizin, thaumatin, L-aspartyl L-phenylalanine methyl ester, saccharin, acesulfame K, sucralose, glycine, and alanine; and fillers such as dextrins, starches, and lactose. Particularly, the cyclotetrasaccharide and the saccharide compositions comprising the same can be suitably used as a low-caloric sweetener, diet sweetener, or the like in combination with one or more low-caloric sweeteners such as meso-erythritol, xylitol, and maltitol; and/or one or more sweeteners with a relatively-high sweetening power such as α-glycosyl stevioside, thaumatin, L-aspartyl L-phenylalanine methyl ester, saccharin, acesulfame K, and sucralose.

The cyclotetrasaccharide and the saccharide compositions comprising the same of the present invention can be arbitrarily used intact or after mixing with fillers, excipients, binders, etc., and then formed into products with different shapes such as granules, spheres, plates, cubes, and tablets.

The cyclotetrasaccharide and the saccharide compositions comprising the same of the present invention well harmonize with other tastable materials having sour-, acid-, salty-, delicious-, astringent-, and bitter-tastes; and have a satisfactorily high acid- and heat-tolerance. Thus, they can be favorably used as sweeteners, taste-improving agents, quality-improving agents, etc., to sweeten and/or improve the taste and quality of food products in general, for example, a soy sauce, powdered soy sauce, miso, "funmatsu-miso" (a powdered miso), "moromi" (a refined sake), "hishio" (a refined soy sauce), "furikake" (a seasoned fish meal), mayonnaise, dressing, vinegar, "sanbai-zu" (a sauce of sugar, soy sauce and vinegar), "funmatsu-sushi-su" (powdered vinegar for sushi), "chuka-no-moto" (an instant mix for Chinese dish), "tentsuyu" (a sauce for Japanese deep-fat fried food), "mentsuyu" (a sauce for Japanese vermicelli), sauce, catsup, "yakiniku-no-tare" (a sauce for Japanese grilled meat), curry roux, instant stew mix, instant soup mix, "dashi-no-moto" (an instant stock mix), mixed seasoning, "mirin" (a sweet sake), "shin-mirin" (a synthetic mirin), table sugar, and coffee sugar. Also, the cyclotetrasaccharide and the saccharide compositions comprising the same of the present invention can be arbitrarily used to sweeten and improve the taste and quality of "wagashi" (Japanese cakes) such as "senbei" (a rice cracker), "arare" (a rice cake cube), "okoshi" (a millet-and-rice cake), "gyuhi" (a starch paste), "mochi" (a rice paste) and the like, "manju" (a bun with a bean-jam), "uiro" (a sweet rice jelly), "an" (a bean jam) and the like, "yokan" (a sweet jelly of beans), "mizu-yokan" (a soft adzuki-bean jelly), "kingyoku" (a kind of yokan), jelly, pao de Castella, and "amedama" (a Japanese toffee); Western confectioneries such as a bun, biscuit, cracker, cookie, pie, pudding, butter cream, custard cream, cream puff, waffle, sponge cake, doughnut, chocolate, chewing gum, caramel, nougat, and candy; frozen desserts such as an ice cream and sherbet; syrups such as a "kajitsu-no-syrup-zuke" (a preserved fruit) and "korimitsu" (a sugar syrup for shaved ice); pastes such as a flour paste, peanut paste, and fruit paste; processed fruits and vegetables such as a jam, marmalade, "syrup-zuke" (fruit pickles), and "toka" (conserves); pickles and pickled products such as a "fukujin-zuke" (red colored radish pickles), "bettara-zuke" (a kind of whole fresh radish pickles), "senmai-zuke" (a kind of sliced fresh radish pickles), and "rakkyo-zuke" (pickled shallots); premixes for pickles and pickled products such as a "takuan-zuke-no-moto" (a premix for pickled radish), and "hakusai-zuke-no-moto" (a premix for fresh white rape pickles); meat products such as a ham and sausage; products of fish meat such as a fish ham, fish sausage, "kamaboko" (a steamed fish paste), "chikuwa" (a kind of fish paste), and "tenpura" (a Japanese deep-fat fried fish paste); "chinmi" (relish) such as a "uni-no-shiokara" (salted guts of sea urchin), "ika-no-shiokara" (salted guts of squid), "su-konbu" (processed tangle), "saki-surume" (dried squid strips), "fugu-no-mirin-boshi" (a dried mirin-seasoned swellfish), seasoned fish flour such as of Pacific cod, sea bream, shrimp, etc; "tsuku-dani" (foods boiled down in soy sauce) such as those of layer, edible wild plants, dried squid, small fish, and shellfish; daily dishes such as a "nimame" (cooked beans), potato salad, and "konbu-maki" (a tangle roll); milk products; canned and bottled products such as those of meat, fish meat, fruit, and vegetable; alcoholic beverages such as a synthetic sake, fermented liquor, sake, fruit wine, sparkling alcoholic beverage, beer; soft drinks such as a coffee, cocoa, juice, carbonated beverage, sour milk beverage, and beverage containing a lactic acid bacterium; instant food products such as instant pudding mix, instant hot cake mix, instant juice or soft drink, instant coffee, "sokuseki-shiruko" (an instant mix of adzuki-bean soup with rice cake), and instant soup mix; and other foods and beverages such as solid foods for babies, foods for therapy, health/tonic drinks, peptide foods, and frozen foods. The cyclotetrasaccharide and the saccharide compositions comprising the same of the present invention can be arbitrary used to prolong or retain the flavor and taste of fresh-baked Japanese and Western confectioneries and to improve the taste preference of feeds and pet foods for animals and pets such as domestic animals, poultry, honey bees, silk worms, and fish; and also they can be arbitrary arbitrarily used as a sweetener, taste-improving agent, flavoring substance, quality-improving agent, and stabilizer in other products in a paste or liquid form such as a tobacco, cigarette, tooth paste, lipstick, rouge, lip cream, internal liquid medicine, tablet, troche, cod liver oil in the form of drop, cachou, oral refrigerant, gargle, cosmetic, and pharmaceutical. When used as a quality-improving agent or stabilizer, the cyclotetrasaccharide and the saccharide compositions comprising the same of the present invention can be arbitrarily used in biologically active substances susceptible to lose their effective ingredients and activities, as well as in health foods and pharmaceuticals containing the biologically active substances. Examples of such biologically active substances are liquid preparations containing lymphokines such as $\alpha$-, $\beta$- and $\gamma$-interferons, tumor necrosis factor-$\alpha$ (TNF-...$\alpha$), tumor necrosis factor-$\beta$ (TNF-13), macrophage migration inhibitory factor, colony-stimulating factor, transfer factor, and interleukin 2; liquid preparations containing hormones such as insulin, growth hormone, prolactin, erythropoietin, and follicle-stimulating hormone; biological preparations such as BCG vaccine, Japanese encephalitis vaccine, measles vaccine, live polio vaccine, smallpox vaccine, tetanus toxoid, Trimeresurus antitoxin, and human immunoglobulin; antibiotics such as penicillin, erythromycin, chloramphenicol, tetracycline, streptomycin, and kanamycin sulfate; liquid preparations containing vitamins such as thiamine, riboflavin, L-ascorbic acid, cod liver oil, carotenoid, ergosterol, and tocopherol; highly unsaturated fatty acids and ester derivatives thereof such as EPA, DHA, and arachidonic acid; solutions of enzymes such as lipase, elastase, urokinase, protease, $\beta$-amylase, isoamylase, glucanase, and lactase; extracts such as ginseng extract, snapping turtle extract, chlorella extract, aloe extract, and propolis extract; and royal jelly. By using the cyclotetrasaccharide and the saccharide compositions comprising the same of the present invention, the above biologically active substances and other pastes of living microorganisms such as viruses, lactic acid bacteria, and yeasts can be arbitrarily prepared into health foods and pharmaceuticals in a liquid, paste, or solid form, which have a satisfactorily-high stability and quality with less fear of losing or inactivating their effective ingredients and activities.

As mentioned above, the following effects and features are also effectively exerted when used with other ingredients which are generally used externally: The effects of preventing the volatilization or the keeping of ingredients of fragrances and flavors, preventing syneresis, crystallization of other saccharides, and deterioration of proteins, lipids, and active ingredients, retaining moisture, and stabilizing emulsified conditions, which are exerted by the cyclotetrasaccharide and the saccharide compositions comprising the same;

and the features of stability and filler-imparting ability inherent to the cyclotetrasaccharide and the saccharides.

Similarly as other naturally occurring saccharides, since the cyclotetrasaccharide and the saccharide compositions comprising the same of the present invention quite scarcely stimulate the skin when applied thereupon and effectively retain the moisture in the skin, they can be advantageously incorporated into external dermal compositions for use. In the external dermal compositions, the cyclotetrasaccharide and the saccharide compositions comprising the same of the present invention can be usually used in an appropriate combination with one or more dermatologically applicable other ingredients of oils and lipids, waxes, hydrocarbons, fatty acids, esters, alcohols, surfactants, dyes, flavors, hormones, vitamins, plant extracts, animal extracts, microbial extracts, salts, ultraviolet absorbents, photosensitizing dyes, antioxidants, antiseptics/bactericides, antiperspirants/deodorants, refreshments, chelating agents, skin whitening agents, anti-inflammatories, enzymes, saccharides, amino acids, and thickening agents. For example, in the field of cosmetics, the external dermal compositions can be provided in the form of a lotion, cream, milky lotion, gel, powder, paste, or block, for example, cleaning cosmetics such as soaps, cosmetic soaps, washing powders for the skin, face washing creams, facial rinses, body shampoos, body rinses, shampoos, and powders for washing hair; cosmetics for hair such as set lotions, hair blows, stick pomades, hair creams, pomades, hair sprays, hair liquids, hair tonics, hair lotions, hair restorers, hair dyes, treatments for scalp, hair cosmetics, gloss-imparting hair oils, hair oils, and combing oils; base cosmetics such as cosmetic lotions, vanishing creams, emollient creams, emollient lotions, cosmetic packs in the form of a jelly peel off, jelly wiping, paste washing, powders, cleansing creams, cold creams, hand creams, hand lotions, milky lotions, moisture-imparting liquids, after/before shaving lotions, after shaving creams, after shaving foams, before shaving creams, and baby oils; makeup cosmetics such as foundations in the form of a liquid, cream or solid, talcum powders, baby powders, body powders, perfume powders, makeup bases, powders in the form of a cream, paste, liquid, solid or powder, eye shadows, eye creams, mascaras, eyebrow pencils, eyelash makeups, rouges, rouge lotions; perfume cosmetics such as perfumes, paste/powder perfumes, eau de Colognes, perfume Colognes, and eau de toilette; suntan and suntan preventive cosmetics such as suntan creams, suntan lotions, and suntan oils; nail cosmetics such as manicures, pedicures, nail colors, nail lacquers, and nail makeup materials; eyeliner cosmetics; rouges and lipsticks such as lipsticks, lipcreams, paste rouges, and lip-glosses; oral cosmetics such as tooth pastes and mouth washes; and bath cosmetics such as bath salts/oils, and bath cosmetic materials. In the field of pharmaceuticals, the external dermal compositions can be provided in the form of a wet compresses, sprays, applications, bath agents, sticking agents, ointments, pastes, embrocations, lotions, and cataplasms.

Concrete examples of the other ingredients, which can be incorporated into the external dermal compositions along with the cyclotetrasaccharide and the saccharide compositions comprising the same, are oils and fats including plant oils in the form of a liquid at ambient temperature such as an avocado oil, almond oil, olive oil, sesame oil, safflower oil, soy bean oil, camellia oil, persic oil, castor oil, and cotton seed oil; plant fats in the form of a solid at ambient temperature such as a cacao fat, palm fat/oil, and vegetable wax; and animal oils such as mink oil, egg yolk oil, and turtle oil.

Examples of the waxes usable in the present invention are plant waxes such as a hohoba oil, carnauba was, and candelilla wax; animal waxes such as a sperm oil, Baird's beaked while oil, beeswax, whale oil, and lanoline; and mineral oils such as a montan wax.

The carbohydrates usable in the present invention are, for example, mineral carbohydrates such as a paraffin or solid paraffin, liquid paraffin, ceresin, microcrystalline wax, and petrolatum; and animal hydrocarbons such as squalane and squalene.

Examples of the fatty acids usable in the present invention are lauric acid, myristic acid, palmitic acid, stearic acid, oleic acid, behenic acid, undecylenic acid, lanolin fatty acid, hard lanolin fatty acid, soft lanolin fatty acid, isostearic acid, and derivatives thereof.

The alcohols usable in the present invention are, for example, higher alcohols including polyalcohols such as lauryl alcohol, cetanol, setostearyl alcohol, stearyl alcohol, oleyl alcohol, behenyl alcohol, lanolin alcohol, hydrogenated lanolin alcohol, hexyldecanol, octyldodecanol, and polyethylene glycol; lower alcohols including polyalcohols such as ethanol, propanol, isopropanol, butanol, ethylene glycol, propylene glycol, and glycerine; and derivatives thereof.

Examples of the esters usable in the present invention are hexyl laurate, isopropyl myristate, myristyl myristate, cetyl myristate, octyl dodecyl myristate, isopropyl palmitate, butyl stearate, cholesteryl stearate, cholesteryl acetate, cholesteryl n-lactate, cholesteryl caproate, cholesteryl laurate, cholesteryl myristate, cholesteryl palmitate, cholesteryl stearate, cholesteryl 12-hydroxystearate, decyl oleate, octyldodecyl oleate, isopropyl lanolin fatty acid, glycerine trimyristate, propylene glycol dioleate, myristyl lactate, cetyl lactate, lanolin acetate, hexyldecyl dimethyloctanoate, and derivatives thereof.

The surfactants usable in the present invention are, for example, anionic surfactants such as zinc laurate, zinc myristate, zinc palmitate, magnesium stearate, sodium lauryl sulfate, sodium polyoxyethylene laurylether sulfate, triethanolamine polyoxyethylene laurylether sulfate, polyoxyethylene cetylether phosphate, polyoxyethylene alkylphenylether phosphate, sodium N-lauroyl sarcosinate, coconut fatty acid sarcosinate triethanolamine, coconut fatty acid sodium methyltaurate, and soybean phospholipid; cationic surfactants such as stearyltrimethylammonium chloride, distearyldimethylammonium chloride, benzalkonium chloride, cetylpyridinium chloride, alkylisoquinolinium bromide, and. . . dodecyldimethyl 2-phenoxyethylammonium bromide; amphoteric ion surfactants such as sodium β-laurylaminopropionate, betaine lauryldimethylamino acetate, and 2-alkyl-N-carboxymethyl-N-hydroxyethyl imidazolinium betaine; non-ionic surfactants such as glyceryl monostearate, self-emulsifying, glyceryl monostearate, lipophilic, sorbitan monolaurate, sorbitan monooleate, sucrose fatty acid ester, undecylenic acid monoethanolamide, coconut oil diethanolamide, polyethylene glycol monooleate, myristyl lactate, cetyl lactate, polyoxyethylene cetylether, polyoxyethylene octylphenylether, polyoxyethylene sorbitol monolaurate, polyoxyethylene sorbitan monolaurate, polyoxyethylene sorbitan monostearate, polyoxyethylene sorbitan trioleate, polyoxyethylene sorbitol tetraoleate, polyoxyethylene castor oil, and polyoxyethylene hydrogenated castor oil; and derivatives thereof.

Examples of the dyes usable in the present invention are red tar dyes such as amaranth, erythrosine, rose bengal, acid red, lake red C, lithol red, rhodamine, brilliant lake red, eosine YS, violamine R, brilliant fast scarlet, Ponceau R, orange tar dyes such as dibromofluorescein, permanent orange, erythrosine yellow NA, and orange I; yellow tar dyes such as tartrazine, sunset yellow, uranin, benzidine yellow G, naphthol yellow S, and yellow AB; green tar dyes such as fast green FCF, alizarin cyanine green F, light green SF yellow, and naphthol green B; blue tar dyes such as brilliant blue FCF, indigo carmine, indigo, patent blue NA, carbanthrene blue, and sudan blue; brown tar dyes such as resorcin brown; purple tar dyes such as alizarin purple and alizarin purple; black tar dyes such as naphthol blue black; inorganic pigments such as zinc oxide, titanium oxide, cobalt hydroxide, aluminum hydroxide, talc, kaolin, mica, bentonite, manganese violet, and mica titanium; carotenoid pigments such as β-carotenoid, lycopene, and crocin; flavonoid pigments such as sisonine, saffrol yellow, rutin, and quercetin; flavin pigments such as riboflavin; quinone pigments such as cochineal, alizarine, and shikonin; and derivatives thereof.

The fragrances used generally in external dermal uses can be roughly classified into natural plant and animal fragrances, synthetic fragrances, and mixtures thereof in an appropriate combination. Examples of the animal fragrances include musk, civetone, and ambergris. The plant fragrancese are, for example, distillations, i.e., essential oils, obtainable by distilling, for example, with water vapor anise seeds, basil leaves, caraway fruit, cinnamon barks, coriander seeds, lavender flowers, nutmeg seeds, peppermint leaves, rose flowers, rosemary flowers, seeds, and leaves, and thyme leaves; extracts classified generally into absolutes, resinoids, oleo resins, and tinctures depending on properties and processes. Examples of the synthetic fragrances are acetophenone, anisole, benzyl alcohol, butyl acetate, camphor, citral, citronellol, cuminaldehyde, estragol, ethylvaniline, geranyl acetate, linarol, menthol, methyl p-cresol, methyl salicylate, phenyl acetate, vanillin, and derivatives thereof. In the present invention, fragrance compositions mixed with the aforesaid flavors in an appropriate combination can be arbitrarily used.

The hormones usable in the present invention include, for example, follicle hormones such as estrone and estradiol; gestagens such as progesterone and pregnenolone; and adrenal cortex hormones such as cortisone, hydrocortisone, and prednisolone. The vitamins usable in the present invention are, for example, vitamin A compounds such as retinol, retinoic acid, α-, β- and γ-carotenes, and derivatives thereof; vitamin B compounds such as thiamine (vitamin B1), riboflavin (vitamin B2), vitamin B6 including pyridoxine, pyridoxal, and pyridoxamine, and derivatives thereof; vitamin C compounds such as L-ascorbic acid, 2-O-α-D-glucosyl-L-ascorbic acid, acyl derivatives, alias lipophilic vitamin C, of L-ascorbic acid and glycosyl-L-ascorbic acid, and other L-ascorbic acid derivatives such as L-ascorbic acid sulfate ester; vitamin D compounds such as ergocalciferol, cholecalciferol, and derivatives thereof; and vitamin E compounds such as α-, β-, γ- and δ-tocopherol, α-, β-, γ- and δ-tocotrienol, and derivatives thereof.

Examples of the plant extracts usable in the present invention are, in addition to the aforesaid plant extracts used a fragrances, extracts such as those of chamomile, sage, aloe, scarlet sage, *Angelica keiskei*, avocado, nettle, fennel, oolong tea, coak tree bark, barley, *Abelmoschus esculentus*, allspice, seaweed, chinese quince, licorice, quince seed, gardenia, *Sasa albo-marginata*, cinnamon, black tea, rice bran, fermented rice bran, *Stevia rebaudiana*, celery, Japanese green gentian, soy bean, thyme, tea, common camellia, *Ligusticurn acutilobum*, corn, carrot, *Rosa rugosa*, hinoki (Japanese cypress), dishcloth gourd, safflower, pine, peach, eucalyptus, creeping saxif rage, yuzu (citron), lily, Job's tears, Mugwort, *Cyanophta* (blue-green algae), seaweed, apple, *Serratia marcescens*, and lettuce; and compounds isolated from plants such as hinokitiol, azulene, chlorophyll, and glycyrrhizin. The animal extracts usable in the present invention include placenta extracts.

Examples of the extracts of microorganisms are yeast extracts. The salts usable in the external dermal composition of the present invention advantageously include those which can be used generally in conventional external dermal compositions, as well as sea water, deep sea water, dried ingredients of sea water, and natural salts, including those in the form of a liquid, such as mineral salts.

The ultraviolet absorbers usable in the present invention include, for example, p-aminobenzoic acid, p-dimethylaminobenzoic acid ethylhexylester, p-methoxycinnamic acid ethylhexylester, 2-(hydroxy-5-methylphenyl)benzotriazole, oxibenzozone, urocanic acid, ethyl urocanate, and derivatives thereof; organic substances capable of shielding ultraviolet rays such as 5-chlorouracil, and guanine cytosine. Examples of the photosensitive dyes usable in the present invention are 2,2'[3'-[2-(3-heptyl-4-methyl-2-thiazolin-2-ylidene)ethyridene]propenylene]bis[3-heptyl-4-methyl thiazolinium iodide] alias "PLATONIN", 2-[2-(3-heptyl-4-methyl-2-thiazolin-2-ylidene)methine]-3-heptyl-4-methyl thiazolinium iodide alias "PIONIN", 6-[2-[(5-bromo-2-pyridyl)amino]vinyl]-1-ethyl-2-picolinium iodide alas "TAKANAL", 2-(2-anilino vinyl)-3,4-dimethyl-oxazolinium iodide alas "LUMINEX", and derivatives thereof.

In addition to the aforesaid compounds having antioxidation ability, the antioxidants usable in the present invention include, for example, propyl gallate, butyl gallate, octyl gallate, dodecyl gallate, nordihydroguaiaretic acid (NDGA), t-butylhydroxyanisole (BHA), butylated hydroxytoluene (BHT), 4-hydroxymethyl-1-2,6-di-t-butylphenol, and derivatives thereof.

Examples of the aseptics and bactericides usable in the present invention include, in addition to the aforesaid compounds with aseptic or bactericidal activities, phenol compounds such as phenol, p-chloro metacresol, resorcin, p-oxy benzoate, and cresol; acid compounds including those in a salt form such as benzoic acid, sorbic acid, salicylic acid, and boric acid; bisphenol halides such as hexachlorophene, bithionol, and dichiorophene; amides such as 3,4,4'-trichiorocarvaniride, undecylenic acid monoethanolamide; quaternary ammonium compounds such as benzalkonium chloride, benzethonium chloride, and decalinium chloride; chiorhexidine hydrochloride, 1-hydroxypyridine-2-thione, lysozyme chloride; and derivatives thereof.

The antiperspirants/deodorants usable in the present invention are, for example, aluminum chloride, zinc chloride, chlorohydroxy aluminum, aluminum chlorohydroxy allantoinate, aluminum dihydroxy allantoinate, and aluminum chlorohydrate. Examples of the refreshments usable in the present invention include menthol, mint/peppermint oil, camphor, thymol, spirantol, and methyl salicylic acid. The chelating agents usable in the present invention are, for example, derivatives of ethylenediaminetetraacetic acid, tripolyphosphoric acid, hexamethacrylic acid, dihydroethylglycine, citric acid, tartaric acid, gluconic acid, and sugar acid.

In addition to the aforesaid compounds with skin whitening activity, the skin whitening agents usable in the present invention are, for example, nucleic acids such as antisense oligonucleotides including antisense oligonucleotides to a tyrosinase gene; kojic acid, lactic acid, anthranilic acid, cumarin, benzotriazole, imidazoline, pyrimidine, dioxane, furan, pyrone, nicotinic acid, arbutin, baicalin, baicalein, and berberine, and derivatives thereof; melanin formation inhibitors, tyrosinase formation inhibitors, and tyrosinase inhibitors.

Examples of the anti-inflammatory agents usable in the present invention include, in addition to the aforesaid those with such anti-inflammatory activity, for example, allantoin, allantoin acetyl-DL-methionine, β-glycyrrhetinic acid allantoinate, ichthammol, indomethacin, acetylsalicylic acid, diphenhydramine chloride, guaiazulene, camazulene, chlorpheniramine maleate, glycyrrhizinic acid, glycyrrhetinic acid, and oriental gromurel extract. Examples of the enzymes usable in the present invention are those from microorganisms of the genera *Bacillus* and *Streptomyces*, and yeasts; and those from plants and animals such as protease, lipase, and lysozyme.

The saccharides usable in the present invention are, for example, oligosaccharides such as sucrose, maltose, fructose, lactose, and trehalose; cyclic saccharides, excluding cyclotetrasaccharide, such as cyclodextrins; sugar alcohols such as maltitol, sorbitol, mannitol, xylitol, and arabitol; polysaccharides such as hyaluronic acid, chondroitin sulfate, pullulan, cellulose, starch, dextran, pectin, carrageenan, guar gum, corn syrup, gum arabic, tragacanth gum, xanthan gum, and chitin, their derivative and partial hydrolyzates. Examples of the amino acids usable in the present invention are glycine, serine, threonine, tyrosine, cysteine, cystine, asparagine, glutamine, 2-pyrrolidone-5-carboxylic acid, hydroxyproline, pipecolic acid, sarcosine, homocysteine, homoserine, citrulline, aspartic acid, glutamic acid, cysteine sulfonic acid, argininosuccinic acid, arginine, lysine, histidine, ornithine, alanine, valine, leucine, isoleucine, methionine, phenylalanine, tryptophane, proline, β-alanine, taurine, β-aminobutyric acid, γ-aminobutyric acid, and salts thereof.

The thickening agents usable in the present invention includes, in addition to the aforesaid compounds having viscosity-imparting ability, for example, water-soluble high molecular substances such as quince seed, sodium alginate, cationated cellulose, hydroxyethyl cellulose, carboxymethyl cellulose, carboxymethyl starch, propylene glycol alginate, collagen, keratin, hydroxypropyl trimethylammonium chloride ether, poly vinyl alcohol, polyvinylpyrrolidone, polyvinylpyrrolidone-vinylacetate copolymer, polyethylene imine, sodium polyacrylate, polyvinylmethyl ether, and carboxyvinylpolymer; electrolytes such as sodium chloride, potassium chloride, and sodium sulfate; and oily materials.

Although the above examples may not completely cover all the compatible salts of the above-exemplified compounds/ingredients if they have such salts, any salt acceptable for external dermal agents other than the above-exemplified salts can be arbitrarily used in the present invention.

The methods for incorporating the cyclotetrasaccharide or the saccharide compositions comprising the same according to the present invention into the aforesaid compositions are those which can incorporate the cyclotetrasaccharide and the saccharide compositions into a variety of compositions before completion of their processings, and which can be appropriately selected among the following conventional methods; mixing, kneading, dissolving, melting, soaking, penetrating, dispersing, applying, coating, spraying, injecting, crystallizing, and solidifying. The amount of the cyclotetrasaccharide or the saccharide compositions comprising the same to be preferably incorporated into the final compositions is usually in an amount of at least 0.1%, desirably, at least 1%.

The following experiments explain the present invention in detail:

Experiment 1

Preparation of Non-Reducing Cyclotetrasaccharide by Culturing

A liquid medium consisting of 5% (w/v) of "PINE-DEX #1", a partial starch hydrolysate commercialized by Matsutani Chemical Ind., Tokyo, Japan, 1.5% (w/v) of "ASA-HIMEAST", a yeast extract commercialized by Asahi Breweries, Ltd., Tokyo, Japan, 0.1% (w/v) of dipotassium phosphate, 0.06% (w/v) of sodium phosphate dodecahydrate, 0.05% (w/v) magnesium sulfate heptahydrate, and water was placed in a 500-ml Erlenmeyer flask in an amount of 100 ml, sterilized by autoclaving at 121° C. for 20 min, cooled, and then seeded with *Bacillus globisporus* C9 strain, FERM BP-7143, followed by culturing under rotary-shaking conditions at 27° C. and 230 rpm for 48 hours and centrifuging the resulting culture to remove cells to obtain a supernatant. The supernatant was autoclaved at 120° C. for 15 min and then cooled, and the resulting insoluble substances were removed by centrifugation to obtain a supernatant.

To examine the saccharides in the supernatant, they were separated from the supernatant by silica gel thin-layer chromatography (abbreviated as "TLC" hereinafter) using, as a developer, a mixture solution of n-butanol, pyridine, and water (=6:4:1), and, as a thin-layer plate, "KIESELGEL 60", an aluminum plate (20×20 cm) for TLC commercialized by Merck & Co., Inc., Rahway, USA.

The coloration of the separated total sugars by the sulfuric acid-methanol method and the reducing saccharides by the diphenylamine-aniline method detected that a non-reducing saccharide was positive on the former detection method but negative on the latter detection method, and had an Rf value of 0.31.

About 90 ml of the supernatant before the saccharide detection was adjusted to pH 5.0 and 45° C. and then incubated for 24 hours after admixed with 1,500 units per gram of solids of "TRANSGLUCOSIDASE L AMANO™", an α-glucosidase commercialized by Amano Pharmaceutical Co., Ltd., Aichi, Japan, and 75 units per gram of solids of a glucoamylase commercialized by Nagase Biochemicals, Ltd., Kyoto, Japan. Thereafter, the resulting culture was adjusted to pH 12 by the addition of sodium hydroxide and boiled for two hours to decompose the remaining reducing sugars. After removing insoluble substances by filtration, the resulting solution was decolored and desalted with "DIAION PK218" and "DIAION WA30", cation exchange resins commercialized by Mitsubishi Chemical Industries, Ltd., Tokyo, Japan, and further desalted with "DIAION SK-1B", commercialized by Mitsubishi Chemical Industries, Ltd., Tokyo, Japan, and "AMBERLITE IRA411", an anion exchange resin commercialized by Japan Organo Co., Ltd., Tokyo, Japan, followed by decoloring with an activated charcoal, membrane filtered, concentrated by an evaporator, and lyophilized in vacuo to obtain about 0.6 g, d.s.b., of a saccharide powder.

The analysis of the saccharide on high-performance liquid chromatography (abbreviated as "HPLC" hereinafter) detected a single peak at an elution time of 10.84 min as shown in FIG. 1, and revealed that the saccharide had a high purity of 99.9% or higher. HPLC was carried out using "SHOWDEX KS-801 column", Showa Denko K.K., Tokyo, Japan, at a column temperature of 60° C. and a flow rate of 0.5 ml/min of water, and using "RI-8012", a differential refractometer commercialized by Tosoh Corporation, Tokyo, Japan.

When measured for reducing power of the saccharide on the Somogyi-Nelson's method, the reducing power was below a detectable level, revealing that the specimen was substantially a non-reducing saccharide.

Experiment 2

Structure Analysis on Non-Reducing Saccharide

Fast atom bombardment mass spectrometry (called "FAB-MS") of a non-reducing saccharide, obtained by the method in Experiment 1, significantly detected a proton-addition-molecular ion with a mass number of 649, and this meant that the saccharide had a mass number of 648.

According to conventional manner, the saccharide was hydrolyzed with sulfuric acid and then analyzed for sugar composition. As a result, only D-glucose was detected, revealing that the saccharide was composed of D-glucose molecules or cyclotetrasaccharide composed of four D-glucose molecules in view of the above mass number.

Figure 2:
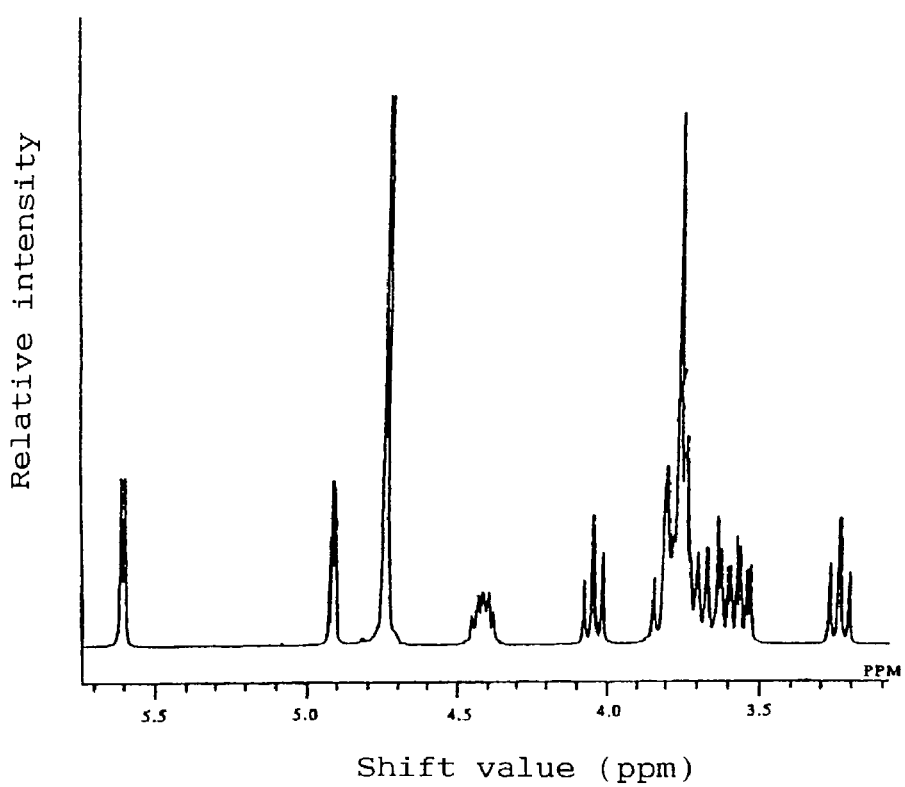
FIG. 2 is a nuclear resonance spectrum ($^1$H-NMR) of cyclotetrasaccharide, obtained by the enzymatic reaction using α-isomaltosyl-transferring enzyme from a microorganism of the species *Bacillus globisporus* C9 strain.
Figure 3:
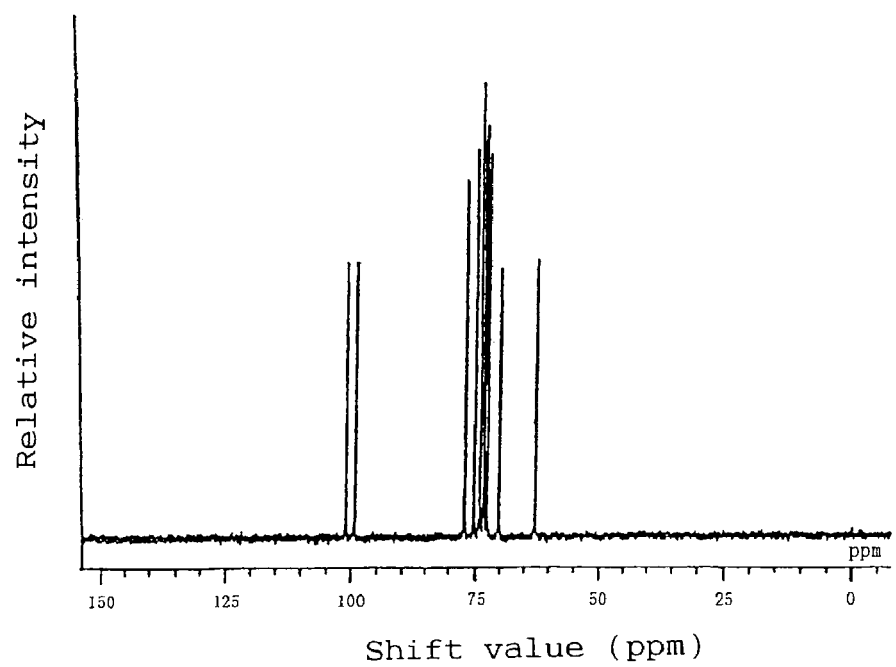
FIG. 3 is a nuclear resonance spectrum ($^{13}$C-NNR) of cyclotetrasaccharide, obtained by the enzymatic reaction using α-isomaltosyl-transferring enzyme from a microorganism of the species *Bacillus globisporus* C9 strain.
Figure 4:
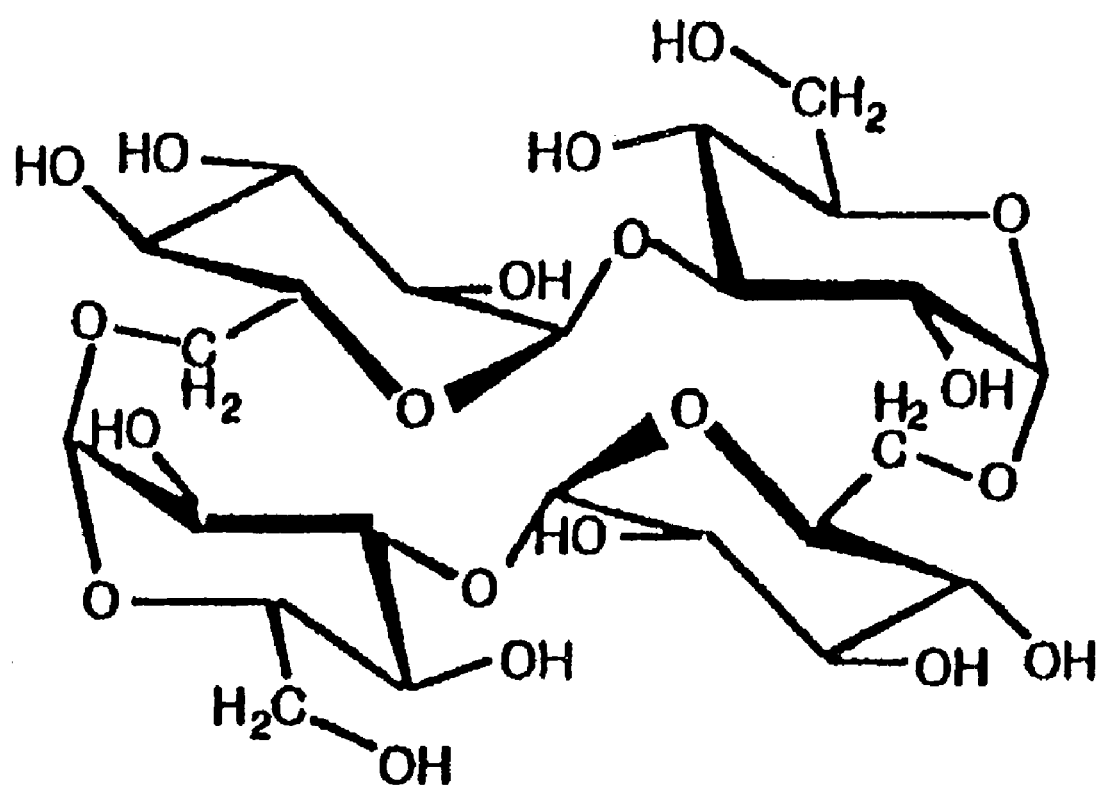
FIG. 4 represents the structure of cyclotetrasaccharide, i.e., cyclo{→6)-α-D-glucopyranosyl-(1→3)-α-D-glucopyranosyl-(1→6)-α-D-glucopyranosyl-(1→3)-α-D-glucopyranosyl-(1→}.

Nuclear magnetic resonance analysis (called "NMR") of the saccharide gave a $^1$H-NMR spectrum as shown in FIG. 2 and a $^{13}$C-NMR spectrum as shown in FIG. 3, and these spectra were compared with those of known saccharides, revealing that they were coincided with a non-reducing cyclic saccharide, cyclo{→6)-α-D-glucopyranosyl-(1→3)-α-D-glucopyranosyl-(1→6)-α-D-glucopyranosyl-(1→3)-α-D-glucopyranosyl-(1→} as disclosed in "*European Journal of Biochemistry*", pp. 641–648 (1994). The data confirmed that the saccharide of the present invention was a cyclotetrasaccharide as shown in FIG. 4, i.e., cyclo{→6)-α-D-glucopyranosyl-(1→3)-α-D-glucopyranosyl-(1→6)-α-D-glucopyranosyl-(1→3)-α-D-glucopyranosyl-(1→}.

Experiment 3

Production of α-isomaltosylglucosaccharide-forming Enzyme from *Bacillus Globisporus* C9 (Strain C9)

A liquid culture medium consisting of 4.0% (w/v) of "PINE-DEX #4", a partial starch hydrolysate commercialized by Matsutani Chemical Ind., Tokyo, Japan, 1.8% (w/v) of "ASAHIMEAST", a yeast extract commercialized by Asahi Breweries, Ltd., Tokyo, Japan, 0.1% (w/v) of dipotassium phosphate, 0.06% (w/v) of sodium phosphate dodecahydrate, 0.05% (w/v) magnesium sulfate heptahydrate, and water was placed in 500-ml Erlenmeyer flasks in a respective amount of 100 ml, sterilized by autoclaving at 121° C. for 20 min, cooled, and then seeded with *Bacillus globisporus* C9 strain, FERM BP-7143, followed by culturing under rotary-shaking conditions at 27° C. and 230 rpm for 48 hours for a seed culture.

About 20L of a fresh preparation of the same liquid culture medium as used in the above seed culture were placed in a 30-L fermentor, sterilized by heating, and then cooled to 27° C. and inoculated with 1% (v/v) of the seed culture, followed by culturing at 27° C. and pH 6.0–8.0 for 48 hours under aeration-agitation conditions. After completion of the culture, the resulting culture, which had about 0.45 unit/ml of the α-isomaltosylglucosaccharide-forming enzyme of the present invention, about 1.5 units/ml of α-isomaltosyl-transferring enzyme, and about 0.95 unit/ml of cyclotetrasaccharide-forming activity, was centrifuged at 10,000 rpm for 30 min to obtain about 18L of a supernatant. When measured for enzymatic activity, the supernatant had about 0.45 unit/ml of the α-isomaltosylglucosaccharide-forming enzyme of the present invention, i.e., a total enzymatic activity of about 8,110 units; about 1.5 units/ml of α-isomaltosyl-transferring enzyme, i.e., a total enzymatic activity of about 26,900 units; and about 0.95 unit/ml of cyclotetrasaccharide-forming activity, i.e., a total enzymatic activity of about 17,100 units.

The activities of these enzymes were assayed as follows:
The α-isomaltosylglucosaccharide-forming enzyme of the present invention was assayed for enzymatic activity by dissolving maltotriose in 100 mM acetate buffer (pH 6.0) to give a concentration of 2% (w/v) for a substrate solution, adding a 0.5 ml of an enzyme solution to a 0.5 ml of the substrate solution, enzymatically reacting the mixture solution at 35° C. for 60 min, suspending the reaction mixture by boiling for 10 min, and quantifying maltose, among the isomaltosyl maltose and maltose formed in the reaction mixture, on HPLC as disclosed in Experiment 1. One unit activity of the α-isomaltosylglucosaccharide-forming enzyme is defined as the enzyme amount that forms one micromole of maltose per minute under the above enzymatic reaction conditions. Throughout the specification, the enzymatic activity of the α-isomaltosylglucosaccharide-forming enzyme means the unit(s) assayed as above.

The α-isomaltosyl-transferring enzyme was assayed for enzymatic activity by dissolving panose in 100 mM acetate buffer (pH 6.0) to give a concentration of 2% (w/v) for a substrate solution, adding a 0.5 ml of an enzyme solution to 0.5 ml of the substrate solution, enzymatically reacting the mixture solution at 35° C. for 30 min, suspending the reaction mixture by boiling for 10 min, and quantifying glucose, among the cyclotetrasaccharide and glucose formed in the reaction mixture, by the glucose oxidase method. One unit activity of the αisomaltosyl-transferring enzyme is defined as the enzyme amount that forms one micromole of glucose per minute under the above enzymatic reaction conditions. Throughout the specification, the enzymatic activity of the α-isomaltosyl-transferring enzyme means the unit(s) assayed as above.

The cyclotetrasaccharide-forming activity is assayed by dissolving "PINE-DEX #100", a partial starch hydrolysate commercialized by Matsutani Chemical Ind., Tokyo, Japan, in 50 mM acetate buffer (pH 6.0) to give a concentration of 2% (w/v) for a substrate solution, adding 0.5 ml of an enzyme solution to 0.5 ml of the substrate solution, enzymatically reacting the mixture solution at 35° C. for 60 min, suspending the reaction mixture by boiling for 10 min, and then further adding to the resulting mixture one milliliter of 50 mM acetate buffer (pH 5.0) with 70 units/ml of "TRANS-GLUCOSIDASE L AMANO™", an α-glucosidase commercialized by Amano Pharmaceutical Co., Ltd., Aichi, Japan, and 27 units/ml of glucoamylase, commercialized by Nagase Biochemicals, Ltd., Kyoto, Japan, and incubated at 50° C. for 60 min, inactivating the remaining enzymes by heating at 100° C. for 10 min, and quantifying cyclotetrasaccharide on HPLC similarly as in Experiment 1. One unit of cyclotetrasaccharide-forming activity is defined as the enzyme amount that forms one micromole of cyclotetrasaccharide per minute under the above enzymatic reaction conditions. Throughout the specification, the cyclotetrasaccharide-forming activity means the activity (units) assayed as above.

Experiment 4

Preparation of Enzyme from *Bacillus Globisporus* C9

Experiment 4-1

About 18L of the supernatant in Experiment 3 was salted out with 80% saturated ammonium sulfate and allowed to stand at 4° C. for 24 hours, and the formed sediments were collected by centrifugation at 10,000 rpm for 30 min, dissolved in 10 mM phosphate buffer (pH 7.5), and dialyzed against a fresh preparation of the same buffer to obtain about 400 ml of a crude enzyme solution with 8,110 units of the α-isomaltosylglucosaccharide-forming enzyme, 24,700 units of α-isomaltosyl-transferring enzyme, and about 15,600 units of cyclotetrasaccharide-forming activity. The crude enzyme solution was subjected to ion-exchange chromatography using 1,000 ml of "SEPABEADS FP-DA13" gel, an ion-exchange resin commercialized by Mitsubishi Chemical Industries, Ltd., Tokyo, Japan. The α-isomaltosylglucosaccharide-forming enzyme and cyclotetrasaccharide were eluted as non-adsorbed fractions without adsorbing on the ion-exchange resin. The resulting enzyme solution was dialyzed against 10 mM phosphate buffer (pH 7.0) with 1M ammonium sulfate, and the dialyzed solution was centrifuged to remove impurities, and subjected to affinity chromatography using 500 ml of "SEPHACRYL HR S-200", a gel commercialized by Amersham Corp., Div. Amersham International, Arlington Heights, Ill., USA. Enzymatically active components adsorbed on the gel and, when sequentially eluted with a linear gradient decreasing from 1M to 0M of ammonium sulfate and a linear gradient increasing from 0mM to 100 mM of maltotetraose, the α-isomaltosylglucosaccharide-forming enzyme and the α-isomaltosyl-transferring enzyme were separately eluted, i.e., the former was eluted with the linear gradient of maltotetraose at about 30 mM and the latter was eluted with the linear gradient of ammonium sulfate at about 0M. Thus, fractions with α-isomaltosyl-transferring activity and those with the α-isomaltosylglucosaccharide-forming activity according to the present invention were separatory collected. No cyclotetrasaccharide-forming activity was found in any of the above fractions and this revealed that a mixture solution of the above fractions with α-isomaltosylglucosaccharide-forming enzyme and α-isomaltosyl-transferring enzyme had also cyclotetrasaccharide-forming activity, and revealed that the activity of forming cyclotetrasaccharide from partial starch hydrolyzates was exerted by the coaction of the activities of the above two types of enzymes.

Methods for separatory purifying the α-isomaltosylglucosaccharide-forming enzyme of the present invention and α-isomaltosyl-transferring enzyme are described in the below:

Experiment 4-2

Purification of α-isomaltosylglucosaccharide-forming Enzyme

A faction of the α-isomaltosylglucosaccharide-forming enzyme of the present invention, obtained in Experiment 4-1, was dialyzed against 10 mM phosphate buffer (pH 7.0) containing 1 M ammonium sulfate. The dialyzed solution was centrifuged to remove insoluble impurities, and the resulting supernatant was fed to hydrophobic chromatography using 350 ml of "BUTYL-TOYOPEARL 650M", a gel commercialized by Tosoh Corporation, Tokyo, Japan. The enzyme was adsorbed on the gel and eluted at about 0.3M ammonium sulfate when eluted with a linear gradient decreasing from 1M to 0M of ammonium sulfate, followed by collecting fractions with the enzyme activity. The fractions were pooled and again dialyzed against 10 mM phosphate buffer (pH 7.0) containing 1M ammonium sulfate. The resulting dialyzed solution was centrifuged to remove impurities and fed to affinity chromatography using "SEPHACRYL HR S-200" gel to purify the enzyme. The amount of enzyme activity, specific activity, and yield of the α-isomaltosylglucosaccharide-forming enzyme in each purification step are in Table 1.

TABLE 1

| Purification step | Enzyme* activity (unit) | Specific activity of enzyme* (unit/mg protein) | Yield (%) |
|---|---|---|---|
| Culture supernatant | 8,110 | 0.12 | 100 |
| Dialyzed solution after salting out with ammonium sulfate | 7,450 | 0.56 | 91.9 |
| Eluate from ion-exchange column chromatography | 5,850 | 1.03 | 72.1 |
| Eluate from affinity column chromatography | 4,040 | 8.72 | 49.8 |
| Eluate from hydrophobic column chromatography | 3,070 | 10.6 | 37.8 |
| Eluate from affinity column chromatography | 1,870 | 13.6 | 23.1 |

Note:
The symbol "*" means the α-isomaltosylglucosaccharide-forming enzyme of the present invention.

The finally purified α-isomaltosylglucosaccharide-forming enzyme specimen was assayed for purity on gel electrophoresis using a 7.5% (w/v) polyacrylamide gel and detected on the gel as a single protein band, i.e., a high purity enzyme specimen.

Experiment 4-3

Purification of α-isomaltosyl-transferring Enzyme

A fraction with α-isomaltosyl-transferring enzyme, which had been separated from a fraction with α-isomaltosylglucosaccharide-forming enzyme by affinity chromatography in Experiment 4-1, was dialyzed against 10 mM phosphate buffer (pH 7.0) containing 1M ammonium sulfate. The resulting dialyzed solution was centrifuged to remove impurities, and subjected to affinity chromatography using "SEPHACRYL HR S-200" gel to purify the enzyme. The amount of enzyme activity, specific activity, and yield of the α-isomaltosyl-transferring enzyme in each purification step are in Table 2.

TABLE 2

| Purification step | Enzyme* activity (unit) | Specific activity of enzyme* (unit/mg protein) | Yield (%) |
|---|---|---|---|
| Culture supernatant | 26,900 | 0.41 | 100 |
| Dialyzed solution after salting out with ammonium sulfate | 24,700 | 1.85 | 91.8 |
| Eluate from ion-exchange column chromatography | 19,400 | 3.41 | 72.1 |
| Eluate from affinity column chromatography | 13,400 | 18.6 | 49.8 |
| Eluate from hydrophobic column chromatography | 10,000 | 21.3 | 37.2 |
| Eluate from affinity column chromatography | 6,460 | 26.9 | 24.0 |

Note:
The symbol "*" means the α-isomaltosyl-transferring enzyme of the present invention.

Experiment 5

Property of α-isomaltosylglucosaccharide-forming Enzyme and α-Isomaltosyl-Transferring Enzyme Experiment 5-1

Property of α-Isomaltosylglucosaccharide-Forming Enzyme

A purified specimen of α-isomaltosylglucosaccharide-forming enzyme, obtained by the method in Experiment 4-2, was subjected to SDS-PAGE using a 7.5% (w/v) of polyacrylamide gel and then determined for molecular weight by comparing with the dynamics of standard molecular markers electrophoresed in parallel, commercialized by Bio-Rad Laboratories Inc., Brussels, Belgium, revealing that the enzyme had a molecular weight of about 140,000±20,000 daltons.

A fresh preparation of the above purified specimen was subjected to isoelectrophoresis using a gel containing 2% (w/v) ampholine commercialized by Amersham Corp., Div. Amersham International, Arlington Heights, Ill., USA, and then measured for pHs of protein bands and gel to determine the isoelectric point of the enzyme, revealing that the enzyme had an isoelectric point of about 5.2±0.5.

Figure 5:
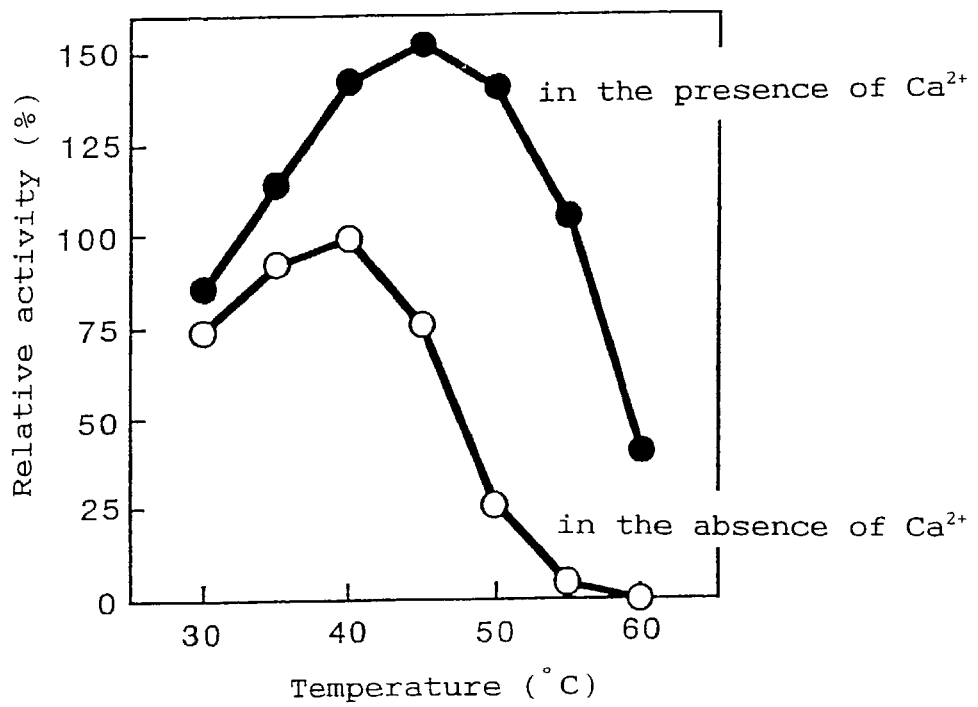
FIG. 5 shows the thermal influence on the enzymatic activity of α-isomaltosylglucosaccharide-forming enzyme from a microorganism of the species *Bacillus globisporus* C9 strain.
Figure 6:
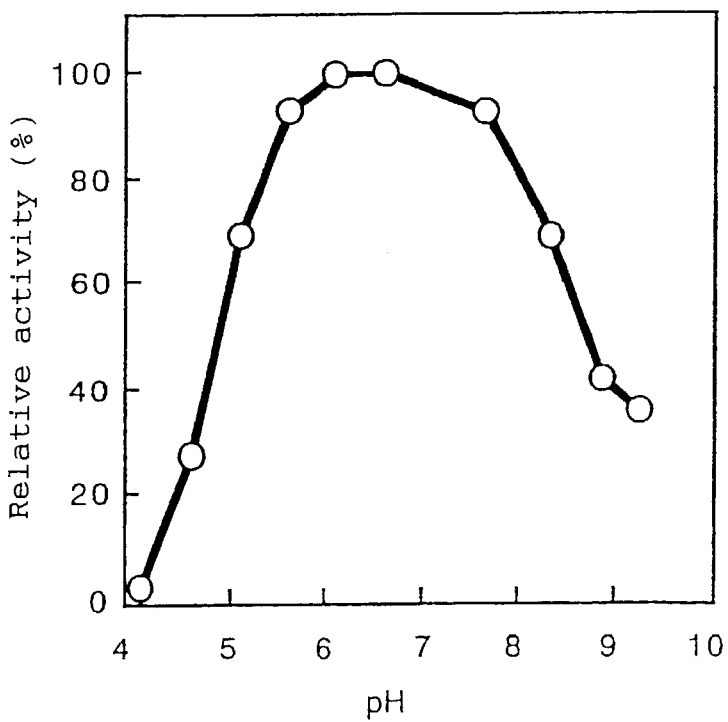
FIG. 6 shows the pH influence on the enzymatic activity of α-isomaltosylglucosaccharide-forming enzyme from a microorganism of the species *Bacillus globisporus* C9 strain.
Figure 7:
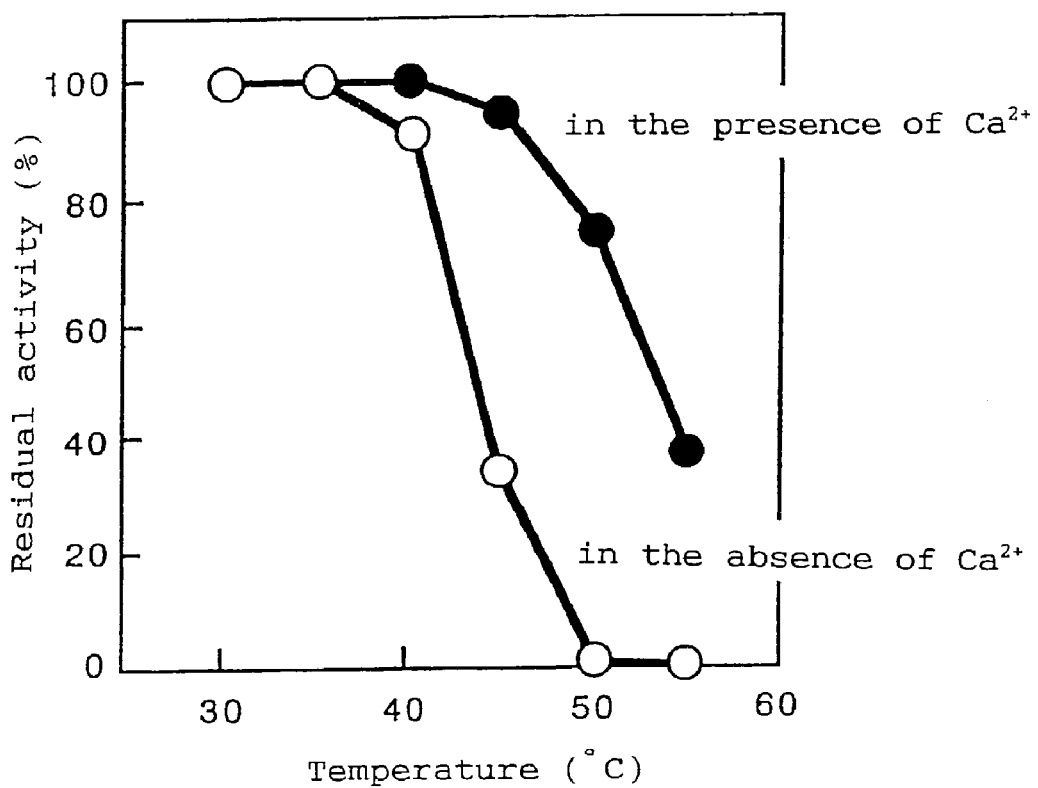
FIG. 7 shows the thermal stability of α-isomaltosylglucosaccharide-forming enzyme from a microorganism of the species *Bacillus globisporus* C9 strain.
Figure 8:
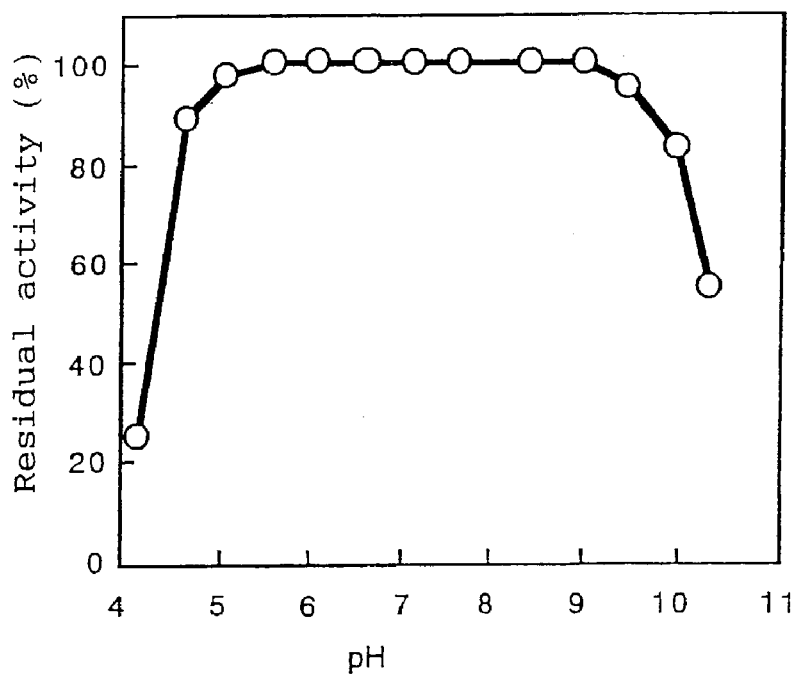
FIG. 8 shows the pH stability of α-isomaltosylglucosaccharide-forming enzyme from a microorganism of the species *Bacillus globisporus* C9 strain.

The influence of temperature and pH on the activity of α-isomaltosylglucosaccharide-forming enzyme was examined in accordance with the assay for the enzyme activity, where the influence of temperature was conducted in the presence or absence of 1 mM $Ca^{2+}$. These results are in FIG. 5 (influence of temperature) and FIG. 6 (influence of pH). The optimum temperature of the enzyme was about 40° C. (in the absence of $Ca^{2+}$) and about 45° C. (in the presence of 1 mM $Ca^{2+}$) when incubated at pH 6.0 for 60 min, and the optimum pH of the enzyme was about 6.0 to about 6.5 when incubated at 35° C. for 60 min. The thermal stability of the enzyme was determined by incubating the testing enzyme solutions in 20 mM acetate buffer (pH 6.0) at prescribed temperatures for 60 min in the presence or absence of 1 mM $Ca^{2+}$, cooling with water the resulting enzyme solutions, and assaying the remaining enzyme activity of each solution. The pH stability of the enzymes was determined by keeping the testing enzyme solutions in 50 mM buffers having prescribed pHs at 4° C. for 24 hours, adjusting the pH of each solution to 6.0, and assaying the remaining enzyme activity of each solution. These results are respectively in FIG. 7 (thermal stability) and FIG. 8 (pH stability). As a result, the enzyme had thermal stability of up to about 35° C. in the absence of $Ca^{2+}$ and about 40° C. in the presence of 1 mM $Ca^{2+}$, and pH stability of about 4.5 to about 9.0.

The influence of metal ions on the activity of α-isomaltosylglucosaccharide-forming enzyme was examined in the presence of 1 mM of each metal-ion according to the assay for the enzyme activity. The results are in Table 3.

TABLE 3

| Metal ion | Relative activity (%) | Metal ion | Relative activity (%) |
|---|---|---|---|
| None | 100 | $Hg^{2+}$ | 4 |
| $Zn^{2+}$ | 92 | $Ba^{2+}$ | 65 |
| $Mg^{2+}$ | 100 | $Sr^{2+}$ | 80 |
| $Ca^{2+}$ | 115 | $Pb^{2+}$ | 103 |
| $Co^{2+}$ | 100 | $Fe^{2+}$ | 98 |
| $Cu^{2+}$ | 15 | $Fe^{3+}$ | 97 |
| $Ni^{2+}$ | 98 | $Mn^{2+}$ | 111 |
| $Al^{3+}$ | 99 | EDTA | 20 |

As evident from the results in Table 3, the enzyme activity was greatly inhibited by $Hg^{2+}$, $Cu^{2+}$, and EDTA, and was also inhibited by $Ba^{2+}$ and $Sr^{2+}$. It was also found that the enzyme was activated by $Ca^{2+}$ and $Mn^{2+}$.

Amino acid analysis of the N-terminal amino acid sequence of the enzyme by "PROTEIN SEQUENCER MODEL 473A", an apparatus of Applied Biosystems, Inc., Foster City, USA, revealed that the enzyme had a partial amino acid sequence of SEQ ID NO:1, i.e., tyrosine-valine-serine-serine-leucine -glycine-asparagine-leucine-isoleucine in the N-terminal region.

Experiment 5-2

Property of α-isomaltosyl-transferring Enzyme

A purified specimen of α-isomaltosyl-transferring enzyme, obtained by the method in Experiment 4-3, was subjected to SDS-PAGE using a 7.5% (w/v) of polyacrylamide gel and then determined for molecular weight by comparing with the dynamics of standard molecular markers electrophoresed in parallel, commercialized by Bio-Rad Laboratories Inc., Brussels, Belgium, revealing that the enzyme had a molecular weight of about 112,000±20,000 daltons.

A fresh preparation of the above purified specimen was subjected to isoelectrophoresis using a gel containing 2% (w/v) ampholine commercialized by Amersham Corp., Div. Amersham International, Arlington Heights, Ill., USA, and then measured for pHs of protein bands and gel to determine the isoelectric point of the enzyme, revealing that the enzyme had an isoelectric point of about 5.5±0.5.

Figure 9:
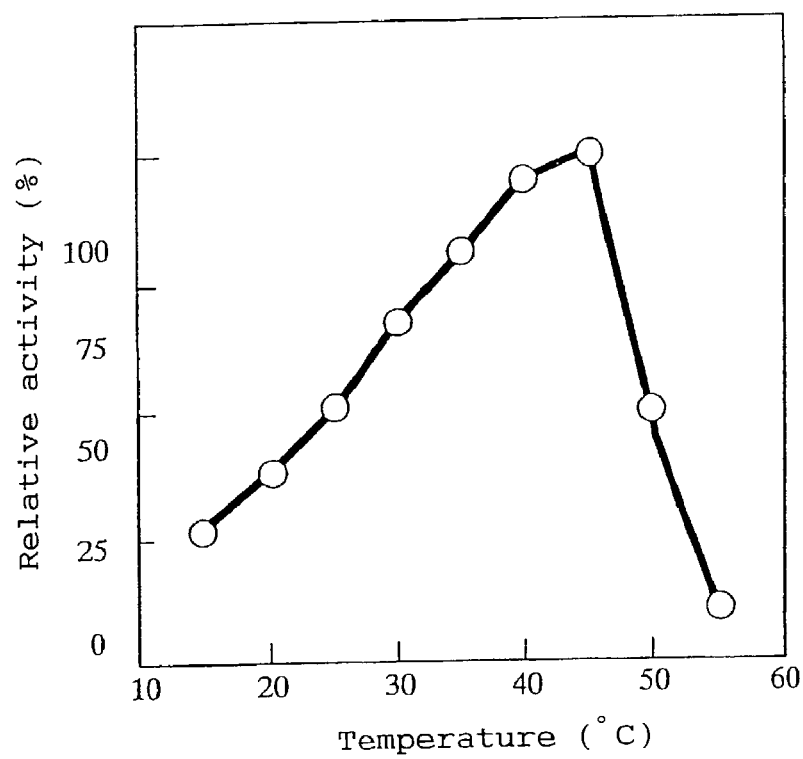
FIG. 9 shows the thermal influence on the enzymatic activity of α-isomaltosyl-transferring enzyme from a microorganism of the species *Bacillus globisporus* C9 strain.
Figure 10:
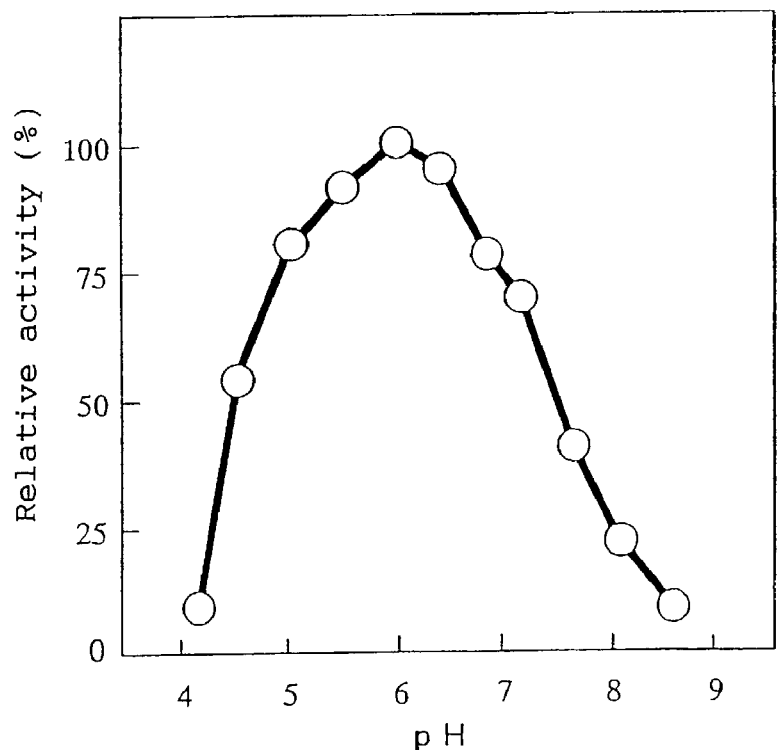
FIG. 10 shows the pH influence on the enzymatic activity of α-isomaltosyl-transferring enzyme from a microorganism of the species *Bacillus globisporus* C9 strain.
Figure 11:
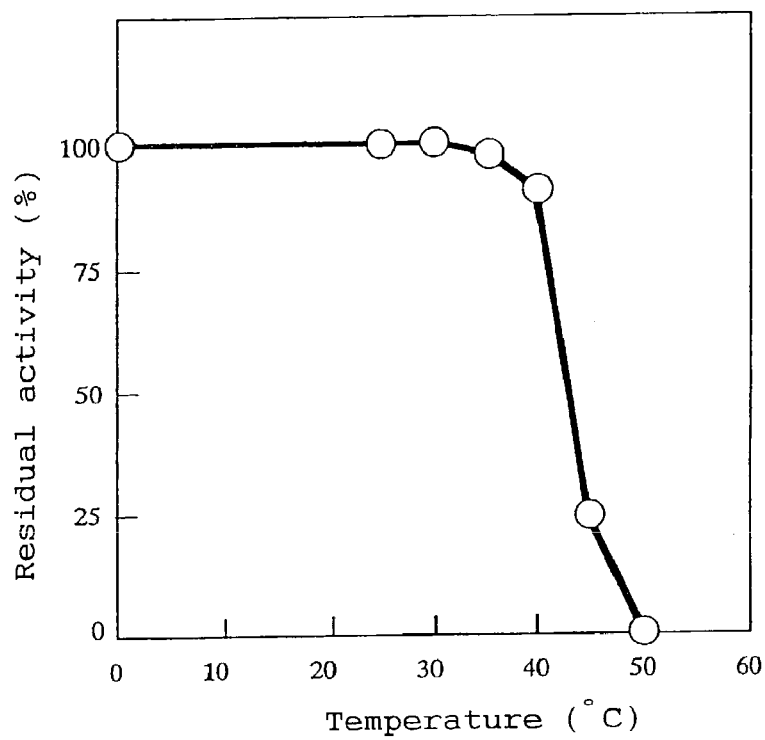
FIG. 11 shows the thermal stability of α-isomaltosyl-transferring enzyme from a microorganism of the species *Bacillus globisporus* C9 strain.
Figure 12:
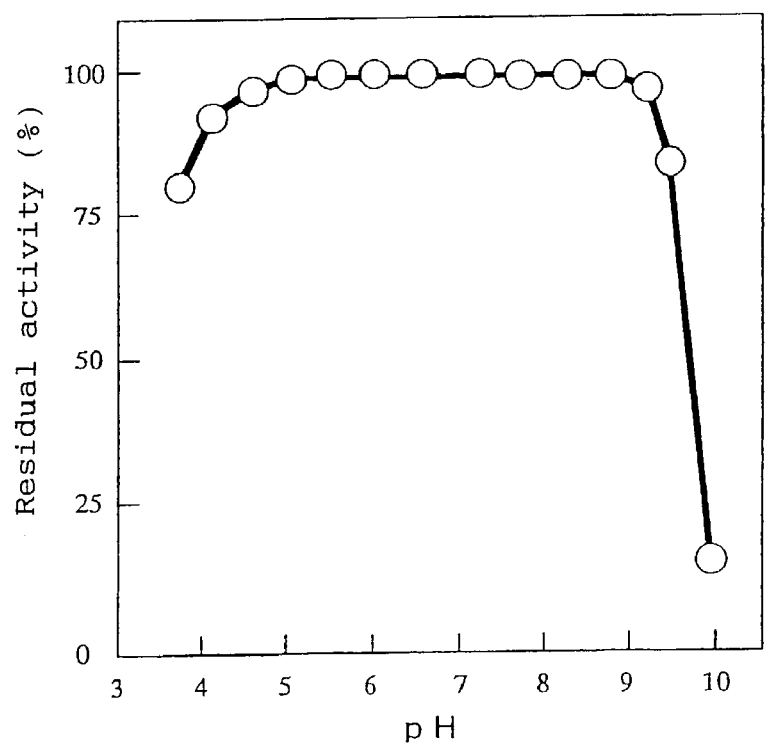
FIG. 12 shows the pH stability of α-isomaltosyl-transferring enzyme from a microorganism of the species *Bacillus globisporus* C9 strain.

The influence of temperature and pH on the activity of α-isomaltosyl-transferring enzyme was examined in accordance with the assay for the enzyme activity. These results are in FIG. 9 (influence of temperature) and FIG. 10 (influence of pH). The optimum temperature of the enzyme was about 45° C. when incubated at pH 6.0 for 30 min, and the optimum pH of the enzyme was about 6.0 when incubated at 35° C. for 30 min. The thermal stability of the enzyme was determined by incubating the testing enzyme solutions in 20 mM acetate buffer (pH 6.0) at prescribed temperatures for 60 min, cooling with water the resulting enzyme solutions, and assaying the remaining enzyme activity of each solution. The pH stability of the enzyme was determined by keeping the testing enzyme solutions in 50 mM buffers having prescribed pHs at 4° C. for 24 hours, adjusting the pH of each solution to 6.0, and assaying the remaining enzyme activity of each solution. These results are respectively in FIG. 11 (thermal stability) and FIG. 12 (pH stability). As a result, the enzyme had thermal stability of up to about 40° C. and pH stability of about 4.0 to about 9.0.

The influence of metal ions on the activity of α-isomaltosyl-transferring enzyme was examined in the presence of 1 mM of each metal-ion according to the assay for the enzyme activity. The results are in Table 4.

TABLE 4

| Metal ion | Relative activity (%) | Metal ion | Relative activity (%) |
|---|---|---|---|
| None | 100 | $Hg^{2+}$ | 1 |
| $Zn^{2+}$ | 88 | $Ba^{2+}$ | 102 |
| $Mg^{2+}$ | 98 | $Sr^{2+}$ | 101 |
| $Ca^{2+}$ | 101 | $Pb^{2+}$ | 89 |
| $Co^{2+}$ | 103 | $Fe^{2+}$ | 96 |
| $Cu^{2+}$ | 57 | $Fe^{3+}$ | 105 |
| $Ni^{2+}$ | 102 | $Mn^{2+}$ | 106 |
| $Al^{3+}$ | 103 | EDTA | 104 |

As evident from the results in Table 4, the enzyme activity was greatly inhibited by $Hg^{2+}$ and was also inhibited by $Cu^{2+}$. It was also found that the enzyme was not activated by $Ca^{2+}$ and not inhibited by EDTA.

Amino acid analysis of the N-terminal amino acid sequence of the enzyme by "PROTEIN SEQUENCER MODEL 473A", an apparatus of Applied Biosystems, Inc., Foster City, USA, revealed that the enzyme had a partial amino acid sequence of SEQ ID NO:2, i.e, isoleucine-aspartic acid-glycine-valine -tyrosine-histidine-alanine-proline-asparagine-glycine in the N-terminal region.

Experiment 6

Production of α-isomaltosylglucosaccharide-forming Enzyme from *Bacillus Globisporus* C11 (Strain C11)

A liquid nutrient culture medium, consisting of 4.0% (w/v) of "PINE-DEX #100", a partial starch hydrolysate, 1.8% (w/v) of "ASAHIMEAST", a yeast extract, 0.1% (w/v) of dipotassium phosphate, 0.06% (w/v) of sodium phosphate dodecahydrate, 0.05% (w/v) magnesium sulfate heptahydrate, and water was placed in 500-ml Erlenmeyer flasks in a volume of 100 ml each, autoclaved at 121° C. for 20 minutes to effect sterilization, cooled, inoculated with a stock culture of *Bacillus globisporus* C11, FERM BP-7144, and incubated at 27° C. for 48 hours under rotary shaking conditions of 230 rpm. The resulting cultures were pooled and used as a seed culture.

About 20L of a fresh preparation of the same nutrient culture medium as used in the above culture were placed in a 30-L fermentor, sterilized by heating, cooled to 27° C., inoculated with 1% (v/v) of the seed culture, and incubated for about 48 hours while stirring under aeration agitation conditions at 27° C. and pH 6.0–8.0. The resultant culture, having about 0.55 unit/ml of α-isomaltosylglucosaccharide-forming enzyme activity, about 1.8 units/ml of α-isomaltosyl-transferring enzyme activity, and about 1.1 units/ml of cyclotetrasaccharide-forming enzyme activity, was centrifuged at 10,000 rpm for 30 min to obtain about 18L of a supernatant. Measurement of the supernatant revealed that it had about 0.51 unit/ml of α-isomaltosylglucosaccharide-forming enzyme activity, i.e., a total enzyme activity of about 9,180 units; about 1.7 units/ml of α-isomaltosyl-transferring enzyme activity, i.e., a total enzyme activity of about 30,400 units; and about 1.1 units/ml of cyclotetrasaccharide-forming enzyme activity, i.e., a total enzyme activity of about 19,400 units.

Experiment 7

Preparation of Enzyme from *Bacillus Globisporus* C11

An 18L of the supernatant obtained in Experiment 6 was salted out with an 80% saturated ammonium sulfate solution and allowed to stand at 4° C. for 24 hours. Then the salted out sediments were collected by centrifugation at 10,000 for 30 min, dissolved in 10 mM phosphate buffer (pH 7.5), dialyzed against a fresh preparation of the same buffer to obtain about 416 ml of a crude enzyme solution. The crude enzyme solution was revealed to have 8,440 units of the α-isomaltosylglucosaccharide-forming enzyme, about 28,000 units of α-isomaltosyl-transferring enzyme, and about 17,700 units of cyclotetrasaccharide-forming enzyme. When subjected to ion-exchange chromatography using "SEPABEADS FP-DA13" gel, disclosed in Experiment 4-1, the above three types of enzymes were eluted as non-adsorbed fractions without adsorbing on the gel. The non-adsorbed fractions with those enzymes were pooled and dialyzed against 10 mM phosphate buffer (pH 7.0) containing 1 M ammonium sulfate, and the dialyzed solution was centrifuged to remove impurities. The resulting supernatant was fed to affinity chromatography using 500 ml of "SEPHACRYL HR S-200" gel to purify the enzyme. Active enzymes was adsorbed on the gel and sequentially was eluted with a linear gradient decreasing from 1M to 0M of ammonium sulfate and a linear gradient increasing from 0 mM to 100 mM of maltotetraose, followed by separate elution of α-isomaltosyl-transferring enzyme and the α-isomaltosylglucosaccharide-forming enzyme, where the former enzyme was eluted with the linear gradient of ammonium sulfate at a concentration of about 0.3M and the latter enzyme was eluted with a linear gradient of maltotetraose at a concentration of about 30 mM. Therefore, fractions with the α-isomaltosylglucosaccharide-forming enzyme of the present invention and those with α-isomaltosyl-transferring enzyme were separately collected and recovered. Similarly as in the case of *Bacillus globisporus* C9 in Experiment 4, it was found that no cyclotetrasaccharide-forming activity was found in any fraction in this column chromatography, and that an enzyme mixture solution of both fractions of α-isomaltosylglucosaccharide-forming enzyme and α-isomaltosyl-transferring enzyme showed cyclotetrasaccharide-forming activity, revealing that the activity of forming cyclotetrasaccharide from partial starch hydrolyzates was exerted in collaboration with the enzyme activities of these enzymes.

The methods for separately purifying the α-isomaltosyl-glucosaccharide-forming enzyme of the present invention and α-isomaltosyl-transferring enzyme are disclosed hereinafter:

Experiment 7-2

Purification of α-isomaltosylglucosaccharide-forming Enzyme

A faction of the α-isomaltosylglucosaccharide-forming enzyme of the present invention was dialyzed against 10 mM phosphate buffer (pH 7.0) containing 1M ammonium sulfate. The dialyzed solution was centrifuged to remove insoluble impurities, and the resulting supernatant was fed to hydrophobic chromatography using 350 ml of "BUTYL-TOYOPEARL 650M", a gel commercialized by Tosoh Corporation, Tokyo, Japan. The enzyme adsorbed on the gel was eluted at about 0.3M ammonium sulfate when eluted with a linear gradient decreasing from 1M to 0M of ammonium sulfate, followed by collecting fractions with the enzyme activity. The fractions were pooled and dialyzed against 10 mM phosphate buffer (pH 7.0) containing 1M ammonium sulfate. The resulting dialyzed solution was centrifuged to remove impurities and fed to affinity chromatography using "SEPHACRYL HR S-200" gel to purify the enzyme. The amount of enzyme activity, specific activity, and yield of the α-isomaltosylglucosaccharide-forming enzyme in each purification step are in Table 5.

TABLE 5

| Purification step | Enzyme* activity (unit) | Specific activity of enzyme* (unit/mg protein) | Yield (%) |
|---|---|---|---|
| Culture supernatant | 9,180 | 0.14 | 100 |
| Dialyzed solution after salting out with ammonium sulfate | 8,440 | 0.60 | 91.9 |
| Eluate from ion-exchange column chromatography | 6,620 | 1.08 | 72.1 |
| Eluate from affinity column chromatography | 4,130 | 8.83 | 45.0 |
| Eluate from hydrophobic column chromatography | 3,310 | 11.0 | 36.1 |
| Eluate from affinity column chromatography | 2,000 | 13.4 | 21.8 |

Note:
The symbol "*" means the α-isomaltosylglucosaccharide-forming enzyme of the present invention.

The finally purified α-isomaltosylglucosaccharide-forming enzyme specimen was assayed for purity on gel electrophoresis using a 7.5% (w/v) polyacrylamide gel and detected on the gel as a single protein band, meaning a high purity enzyme specimen.

Experiment 7-3

Purification of α-isomaltosyl-transferring Enzyme

A fraction of α-isomaltosyl-transferring enzyme, which had been separated from a fraction with α-isomaltosylglucosaccharide-forming enzyme by the affinity chromatography in Experiment 7-1, was dialyzed against 10 mM phosphate buffer (pH 7.0) containing 1M ammonium sulfate. The dialyzed solution was centrifuged to remove insoluble impurities, and the resulting supernatant was fed to hydrophobic chromatography using 350 ml of "BUTYL-TOYOPEARL 650M", a gel commercialized by Tosoh Corporation, Tokyo, Japan. The enzyme adsorbed on the gel and then it was eluted at about 0.3M ammonium sulfate when eluted with a linear gradient decreasing from 1M to 0M of ammonium sulfate, followed by collecting fractions with the enzyme activity. The fractions were pooled and dialyzed against 10 mM phosphate buffer (pH 7.0) containing 1M ammonium sulfate. The resulting dialyzed solution was centrifuged to remove impurities and fed to affinity chromatography using "SEPHACRYL HR S-200" gel to purify the enzyme. The amount of enzyme activity, specific activity, and yield of the α-isomaltosyl-transferring enzyme in each purification step are in Table 6.

TABLE 6

| Purification step | Enzyme* activity (unit) | Specific activity of enzyme* (unit/mg protein) | Yield (%) |
| --- | --- | --- | --- |
| Culture supernatant | 30,400 | 0.45 | 100 |
| Dialyzed solution after salting out with ammonium sulfate | 28,000 | 1.98 | 92.1 |
| Eluate from ion-exchange column chromatography | 21,800 | 3.56 | 71.7 |
| Eluate from affinity column chromatography | 13,700 | 21.9 | 45.1 |
| Eluate from hydrophobic column chromatography | 10,300 | 23.4 | 33.9 |
| Eluate from affinity column chromatography | 5,510 | 29.6 | 18.1 |

Note:
The symbol "*" means α-isomaltosyl-transferring enzyme.

Experiment 8

Property of α-isomaltosylglucosaccharide-forming Enzyme and α-isomaltosyl-transferring Enzyme Experiment 8-1

Property of α-isomaltosylglucosaccharide-forming Enzyme

A purified specimen of α-isomaltosylglucosaccharide-forming enzyme, obtained by the method in Experiment 7-2, was subjected to SDS-PAGE using a 7.5% (w/v) of polyacrylamide gel and then determined for molecular weight by comparing with the dynamics of standard molecular markers electrophoresed in parallel, commercialized by Bio-Rad Laboratories Inc., Brussels, Belgium, revealing that the enzyme had a molecular weight of about 137,000±20,000 daltons.

A fresh preparation of the above purified specimen was subjected to isoelectrophoresis using a gel containing 2% (w/v) ampholine commercialized by Amersham Corp., Div. Amersham International, Arlington Heights, Ill., USA, and then measured for pHs of protein bands and gel to determine the isoelectric point of the enzyme, revealing that the enzyme had an isoelectric point of about 5.2±0.5.

Figure 13:
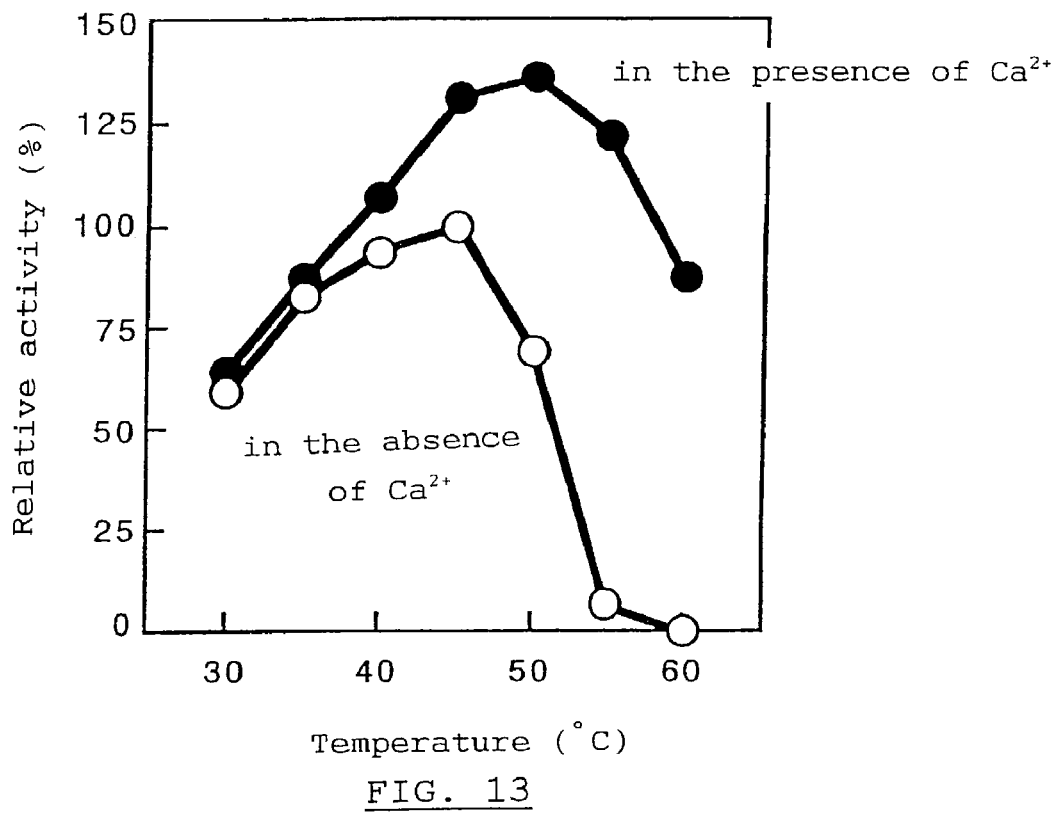
FIG. 13 shows the thermal influence on the enzymatic activity of α-isomaltosylglucosaccharide-forming enzyme from a microorganism of the species *Bacillus globisporus* C11 strain.
Figure 14:
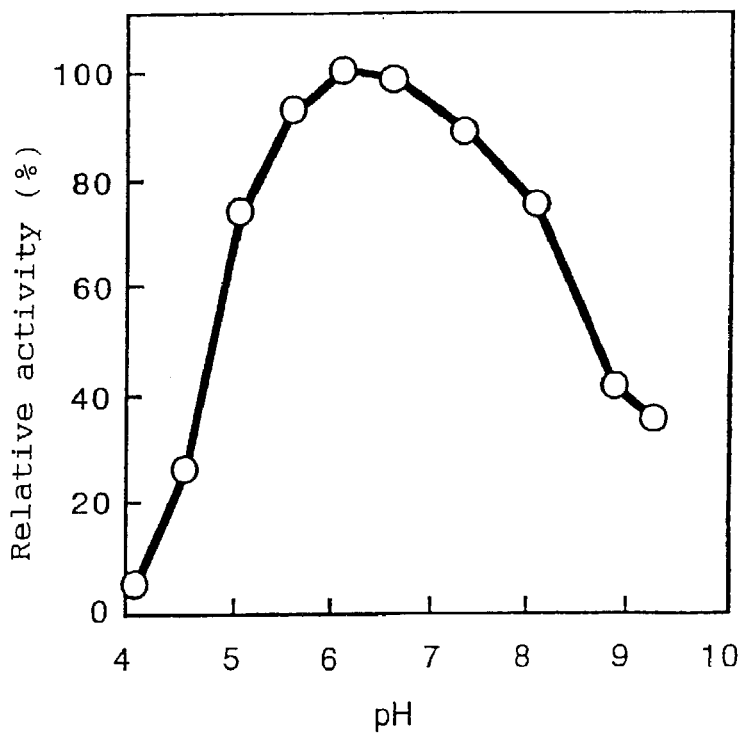
FIG. 14 shows the pH influence on α-isomaltosylglucosaccharide-forming enzyme from a microorganism of the species *Bacillus globisporus* C11 strain.
Figure 15:
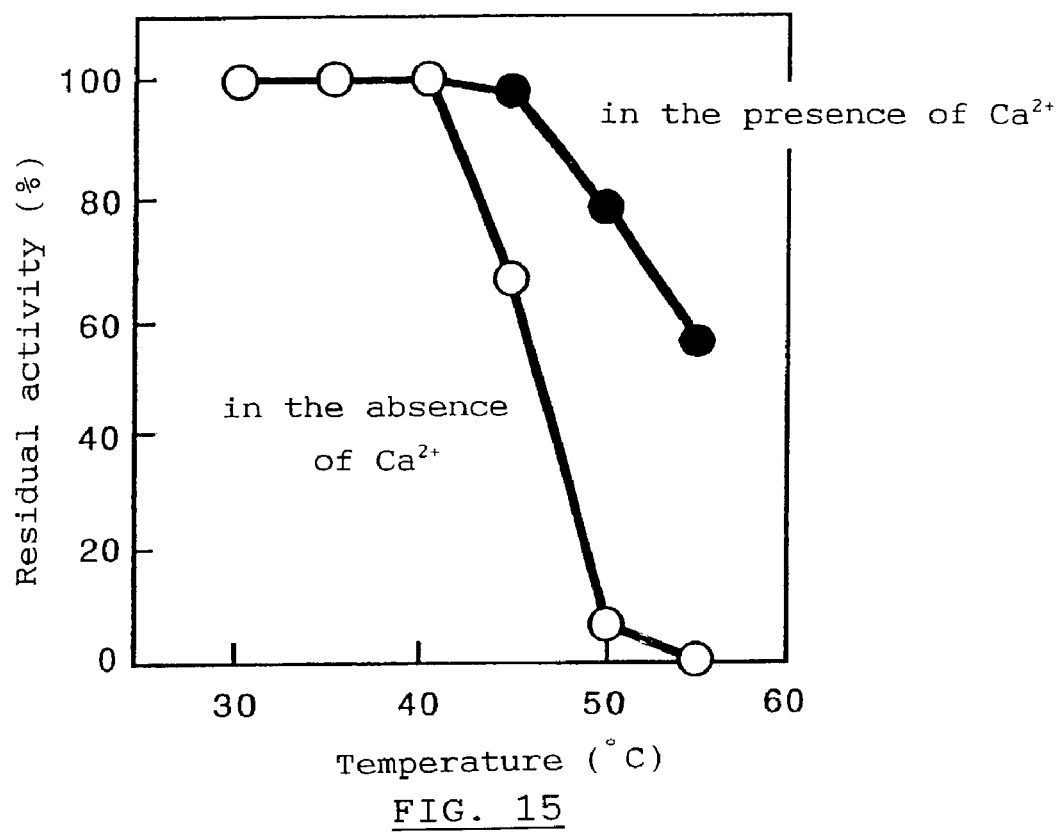
FIG. 15 shows the thermal stability of α-isomaltosylglucosaccharide-forming enzyme from a microorganism of the species *Bacillus globisporus* C11 strain.
Figure 16:
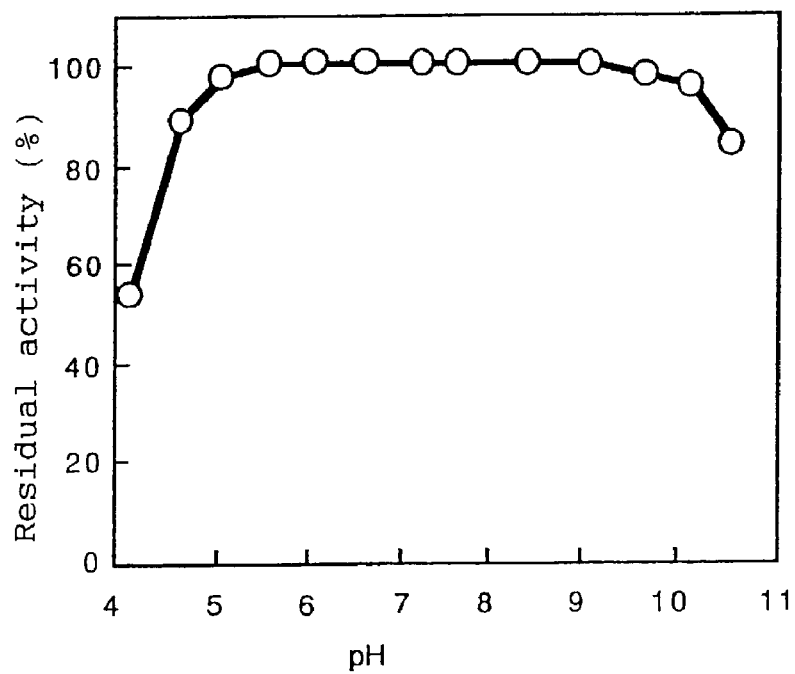
FIG. 16 shows the pH stability of α-isomaltosylglucosaccharide-forming enzyme from a microorganism of the species *Bacillus globisporus* C11 strain.

The influence of temperature and pH on the activity of α-isomaltosylglucosaccharide-forming enzyme was examined in accordance with the assay for the enzyme activity, where the influence of temperature was conducted in the presence or absence of 1 mM $Ca^{2+}$. These results are in FIG. 13 (influence of temperature) and FIG. 14 (influence of pH). The optimum temperature of the enzyme was about 45° C. in the absence of $Ca^{2+}$ and about 50° C. in the presence of 1 mM $Ca^{2+}$ when incubated at pH 6.0 for 60 min. The optimum pH of the enzyme was about 6.0 when incubated at 35° C. for 60 min. The thermal stability of the enzyme was determined by incubating the testing enzyme solutions in 20 mM acetate buffer (pH 6.0) in the presence or absence of 1 mM $Ca^{2+}$ at prescribed temperatures for 60 min, cooling with water the resulting enzyme solutions, and assaying the remaining enzyme activity of each solution. The pH stability of the enzyme was determined by keeping the testing enzyme solutions in 50 mM buffers having prescribed pHs at 4° C. for 24 hours, adjusting the pH of each solution to 6.0, and assaying the remaining enzyme activity of each solution. These results are respectively in FIG. 15 (thermal stability) and FIG. 16 (pH stability). As a result, the enzyme had thermal stability of up to about 40° C. in the absence of $Ca^{2+}$ and up to about 45° C. in the presence of 1 mM $Ca^{2+}$. The pH stability of enzyme was about 5.0 to about 10.0.

The influence of metal ions on the activity of α-isomaltosylglucosaccharide forming enzyme was examined in the presence of 1 mM of each metal-ion according to the assay for the enzyme activity. The results are in Table 7.

TABLE 7

| Metal ion | Relative activity (%) | Metal ion | Relative activity (%) |
| --- | --- | --- | --- |
| None | 100 | $Hg^{2+}$ | 4 |
| $Zn^{2+}$ | 91 | $Ba^{2+}$ | 65 |
| $Mg^{2+}$ | 98 | $Sr^{2+}$ | 83 |
| $Ca^{2+}$ | 109 | $Pb^{2+}$ | 101 |
| $Co^{2+}$ | 96 | $Fe^{2+}$ | 100 |
| $Cu^{2+}$ | 23 | $Fe^{3+}$ | 102 |
| $Ni^{2+}$ | 93 | $Mn^{2+}$ | 142 |
| $Al^{3+}$ | 100 | EDTA | 24 |

As evident from the results in Table 7, the enzyme activity was greatly inhibited by $Hg^{2+}$, $Cu^{2+}$, and EDTA and was also inhibited by $Ba^{2+}$ and $Sr^{2+}$. It was also found that the enzyme was activated by $Ca^{2+}$ and $Mn^{2+}$.

Amino acid analysis of the N-terminal amino acid sequence of the enzyme by "PROTEIN SEQUENCER MODEL 473A", an apparatus of Applied Biosystems, Inc., Foster City, USA, revealed that the enzyme had a partial amino acid sequence of SEQ ID NO:1, i.e, tyrosine-valine-serine-serine-leucine-glycine -asparagine-leucine-isoleucine in the N-terminal region.

The comparison of the partial amino acid sequence in the N-terminal region with that derived from the α-isomaltosylglucosaccharide-forming enzyme from *Bacillus globisporus* C9 in Experiment 5-1 revealed that they were the same and the N-terminal amino acid sequence, commonly found in α-isomaltosylglucosaccharide-forming enzymes, was an amino acid sequence of tyrosine-valine-serine-serine-leucine-glycine -asparagine-leucine-isoleucine of SEQ ID NO:1 in the N-terminal region.

Experiment 8-2

Property of α-isomaltosyl-transferring Enzyme

A purified specimen of α-isomaltosyl-transferring enzyme, obtained by the method in Experiment 7-3, was subjected to SDS-PAGE using a 7.5% (w/v) of polyacrylamide gel and then determined for molecular weight by comparing with the dynamics of standard molecular markers electrophoresed in parallel, commercialized by Bio-Rad Laboratories Inc., Brussels, Belgium, revealing that the enzyme had a molecular weight of about 102,000±20,000 daltons.

A fresh preparation of the above purified specimen was subjected to isoelectrophoresis using a gel containing 2% (w/v) ampholine commercialized by Amersham Corp., Div. Amersham International, Arlington Heights, Ill., USA, and then measured for pHs of protein bands and gel to determine the isoelectric point of the enzyme, revealing that the enzyme had an isoelectric point of about 5.6±0.5.

Figure 17:
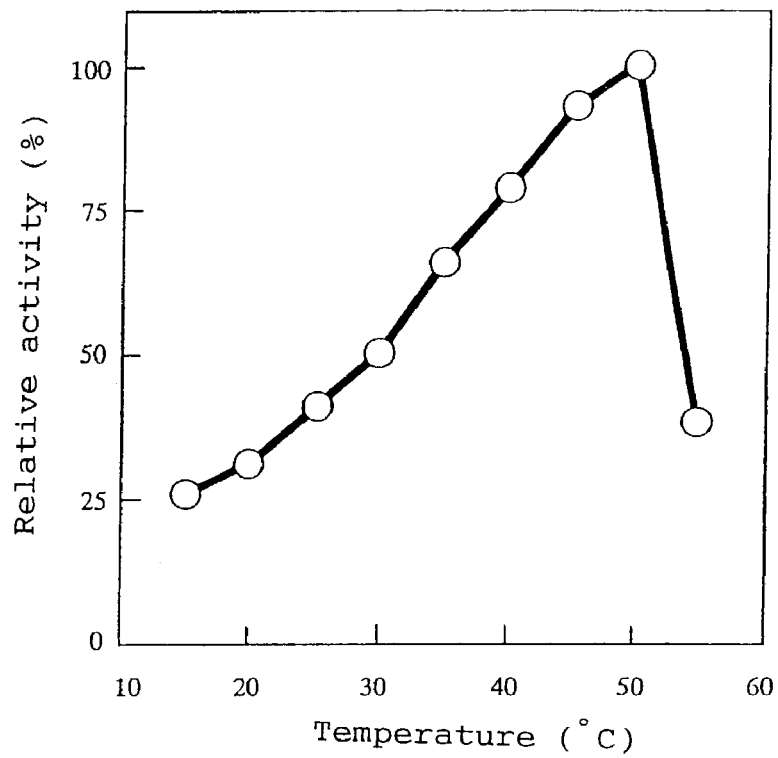
FIG. 17 shows the thermal influence on the enzymatic activity of α-isomaltosyl-transferring enzyme from a microorganism of the species *Bacillus globisporus* C11 strain.
Figure 18:
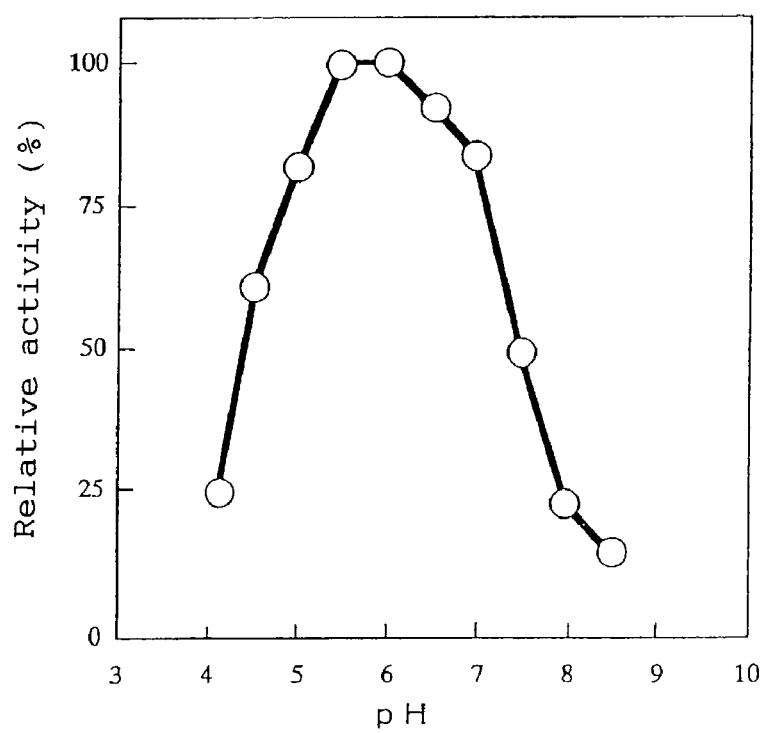
FIG. 18 shows the pH influence on the enzymatic activity of α-isomaltosyl-transferring enzyme from a microorganism of the species *Bacillus globisporus* C11 strain.
Figure 19:
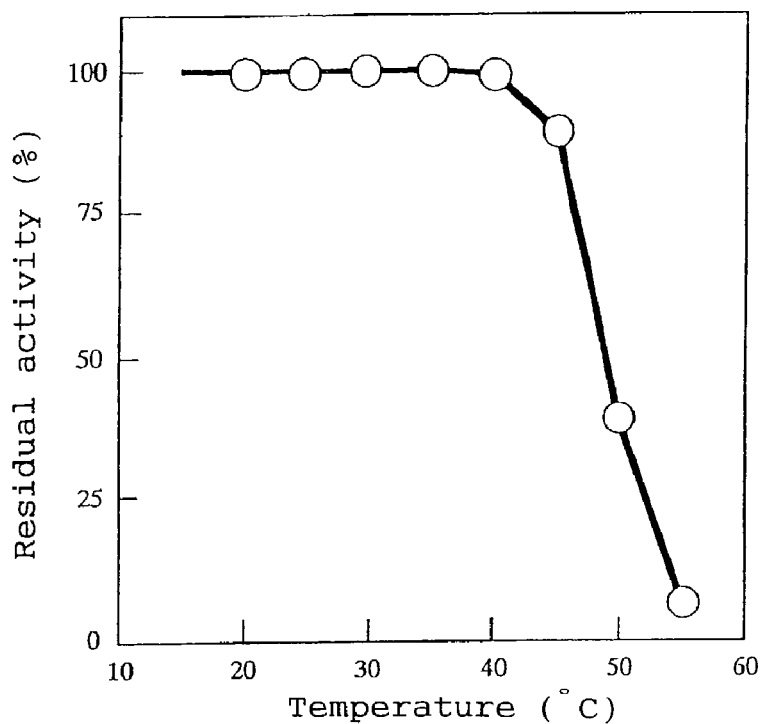
FIG. 19 shows the thermal stability of α-isomaltosyl-transferring enzyme from a microorganism of the species *Bacillus globisporus* C11 strain.
Figure 20:
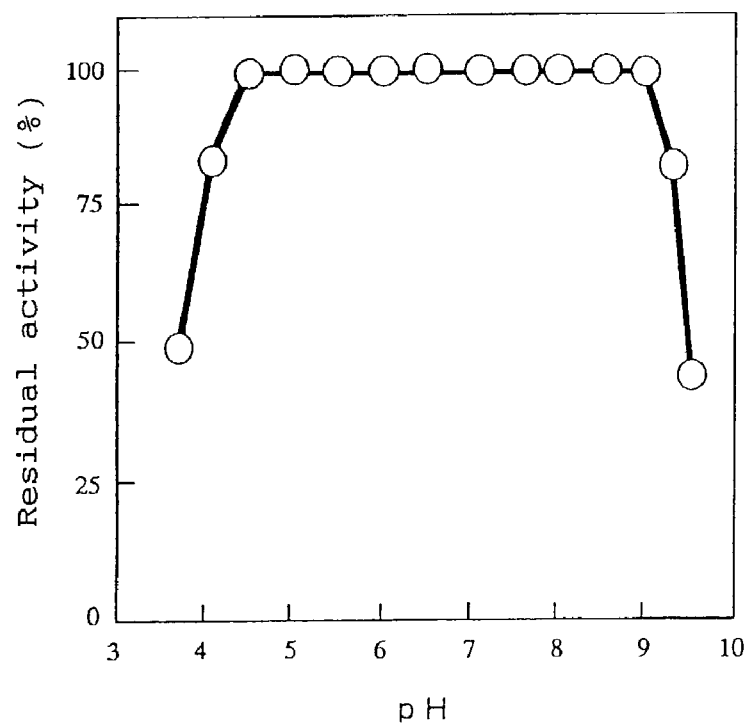
FIG. 20 shows the pH stability of α-isomaltosyl-transferring enzyme from a microorganism of the species *Bacillus globisporus* C11 strain.
Figure 21:
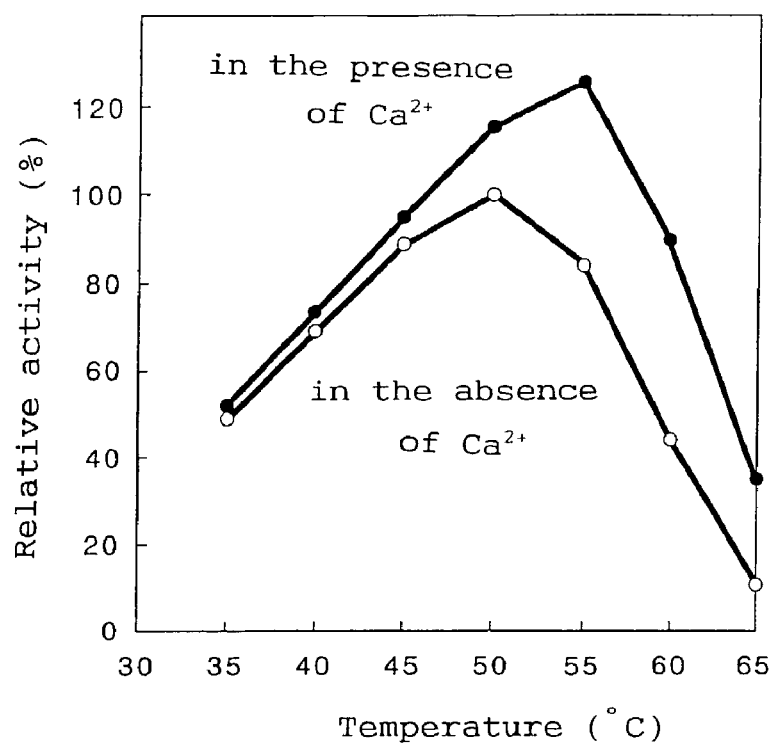
FIG. 21 shows the thermal influence on the enzymatic activity of α-isomaltosylglucosaccharide-forming enzyme from a microorganism of the species *Bacillus globisporus* N75 strain.

The influence of temperature and pH on the activity of α-isomaltosyl-transferring enzyme was examined in accordance with the assay for the enzyme activity. These results are in FIG. 17 (influence of temperature) and FIG. 18 (influence of pH). The optimum temperature of the enzyme was about 50° C. when incubated at pH 6.0 for 30 min. The optimum pH of the enzyme was about 5.5 to about 6.0 when incubated at 35° C. for 30 min. The thermal stability of the enzyme was determined by incubating the testing enzyme solutions in 20 mM acetate buffer (pH 6.0) at prescribed temperatures for 60 min, cooling with water the resulting enzyme solutions, and assaying the remaining enzyme activity of each solution. The pH stability of the enzyme was determined by keeping the testing enzyme solutions in 50 mM buffers having prescribed pHs at 4° C. for 24 hours, adjusting the pH of each solution to 6.0, and assaying the remaining enzyme activity of each solution. These results are respectively in FIG. 19 (thermal stability) and FIG. 20 (pH stability). As a result, the enzyme had thermal stability of up to about 40° C. and pH stability of about 4.5 to about 9.0.

The influence of metal ions on the activity of α-isomaltosyl-transferring enzyme was examined in the presence of 1 mM of each metal-ion according to the assay for the enzyme activity. The results are in Table 8.

TABLE 8

| Metal ion | Relative activity (%) | Metal ion | Relative activity (%) |
|---|---|---|---|
| None | 100 | $Hg^{2+}$ | 2 |
| $Zn^{2+}$ | 83 | $Ba^{2+}$ | 90 |
| $Mg^{2+}$ | 91 | $Sr^{2+}$ | 93 |
| $Ca^{2+}$ | 91 | $Pb^{2+}$ | 74 |
| $Co^{2+}$ | 89 | $Fe^{2+}$ | 104 |
| $Cu^{2+}$ | 56 | $Fe^{3+}$ | 88 |
| $Ni^{2+}$ | 89 | $Mn^{2+}$ | 93 |
| $Al^{3+}$ | 89 | EDTA | 98 |

As evident from the results in Table 8, the enzyme activity was greatly inhibited by $Hg^{2+}$ and was also inhibited by $Cu^{2+}$. It was also found that the enzyme was not activated by $Ca^{2+}$ and not inhibited by EDTA.

Amino acid analysis of the N-terminal amino acid sequence of the enzyme by "PROTEIN SEQUENCER MODEL 473A", an apparatus of Applied Biosystems, Inc., Foster City, USA, revealed that the enzyme had a partial amino acid sequence of SEQ ID NO:3, i.e., isoleucine-aspartic acid-glycine-valine -tyrosine-histidine-alanine-proline-tyrosine-glycine in the N-terminal region.

The comparison of the partial amino acid sequence in the N-terminal region with that derived from the α-isomaltosyl-transferring enzyme from *Bacillus globisporus* C9 in Experiment 5-2 revealed that they had a common amino acid sequence of isoleucine-aspartic acid-glycine-valine-tyrosine-histidine-alanine-proline, as shown in SEQ ID NO:4 at their N-terminal regions.

Experiment 9

Amino Acid Sequence of α-isomaltosylglucosaccharide-forming Enzyme and α-isomaltosyl-transferring Enzyme Experiment 9-1

Internal Amino Acid Sequence of α-isomaltosylglucosaccharide-forming Enzyme

A part of a purified specimen of α-isomaltosylglucosaccharide-forming enzyme, obtained by the method in Experiment 7-2, was dialyzed against 10 mM Tris-HCl buffer (pH 9.0), and the dialyzed solution was diluted with a fresh preparation of the same buffer to give a concentration of about one milligram per milliliter. One milliliter of the dilute as a test sample was admixed with 10 μg of trypsin commercialized by Wako Pure Chemical Industries, Ltd., Tokyo, Japan, and incubated at 30° C. for 22 hours to hydrolyze into peptides. To isolate the hydrolyzed peptides, the resulting hydrolyzates were subjected to reverse-phase HPLC using "μ-Bondapak C18 column" with a diameter of 2.1 mm and a length of 150 mm, a product of Waters Chromatography Div., MILLIPORE Corp., Milford, USA, at a flow rate of 0.9 ml/min and at ambient temperature, and using a liner gradient of acetonitrile increasing from 8% (v/v) to 40% (v/v) in 0.1% (v/v) trifluoroacetate over 120 min. The peptides eluted from the column were detected by monitoring the absorbency at a wavelength of 210 nm. Three peptide specimens named P64 with a retention time of about 64 min, P88 with a retention time of about 88 min, and P99 with a retention time of about 99 min, which had been well separated from other peptides, were separately collected and dried in vacuo and then dissolved in 200 μl of a solution of 0.1% (v/v) trifluoroacetate and 50% (v/v) acetonitrile. Each peptide specimen was subjected to a protein sequencer for analyzing amino acid sequence up to eight amino acid residues to obtain amino acid sequences of SEQ ID NOs:5 to 7. The analyzed internal partial amino acid sequences are in Table 9.

TABLE 9

| Peptide name | Internal partial amino acid sequence |
|---|---|
| P64 | aspartic acid-alanine-serine-alanine-asparagine-valine-threonine-threonine SEQ ID NO:5 |
| P88 | tryptophane-serine-leucine-glycine-phenylalanine-methionine-asparagine-phenylalanine SEQ ID NO:6 |
| P99 | asparagine-tyrosine-threonine-aspartic acid-alanine-tryptophane-methionine-phenylalanine SEQ ID NO:7 |

Experiment 9-2

Internal Amino Acid Sequence of α-isomaltosyl-transferring Enzyme

A part of a purified specimen of α-isomaltosyl-transferring enzyme, obtained by the method in Experiment 7-3, was dialyzed against 10 mM Tris-HCl buffer (pH 9.0), and the dialyzed solution was diluted with a fresh preparation of the same buffer to give a concentration of about one milligram per milliliter. One milliliter of the dilute as a test sample was admixed with 10 μg of "Lysyl Endopeptidase" commercialized by Wako Pure Chemical Industries, Ltd., Tokyo, Japan, and allowed to react at 30° C. for 22 hours to form peptides. The resultant mixtures were subjected to reverse-phase HPLC to separate the peptides using "μ-Bondapak C18 column" having a diameter of 2.1 mm and a length of 150 mm, a product of Waters Chromatography Div., MILLIPORE Corp., Milford, USA, at a flow rate of 0.9 ml/min and at ambient temperature, and using a liner gradient of acetonitrile increasing from 8% (v/v) to 40% (v/v) in 0.1% (v/v) trifluoroacetate over 120 min. The peptides eluted from the column were detected by monitoring the absorbency at a wavelength of 210 nm. Three peptide specimens named P22 with a retention time of about 22 min, P63 with a retention time of about 63 min, and P71 with a retention time of about 71 min, which had been well separated from other peptides, were separately collected and dried in vacuo and then dissolved in 200 μl of a solution of 0.1% (v/v) trifluoroacetate and 50% (v/v) acetonitrile. Each peptide specimen was subjected to a protein sequencer for analyzing amino acid sequence up to eight amino acid residues to obtain amino acid sequences of SEQ ID NOs:8 to 10. The analyzed internal partial amino acid sequences are in Table 10.

TABLE 10

| Peptide name | Internal partial amino acid sequence |
| --- | --- |
| P22 | glycine-asparagine-glutamic acid-methionine-arginine-asparagine-glutamine-tyrosine SEQ ID NO:8 |
| P63 | isoleucine-threonine-threonine-tryptophane-proline-isoleucine-glutamic acid-serine SEQ ID NO:9 |
| P71 | tryptophane-alanine-phenylalanine-glycine-leucine-tryptophane-methionine-serine SEQ ID NO:10 |

Experiment 10

Production of α-isomaltosylglucosaccharide-forming Enzyme from *Bacillus Globisporus* N75 (Strain N75)

A liquid nutrient culture medium, consisting of 4.0% (w/v) of "PINE-DEX #4", a partial starch hydrolysate, 1.8% (w/v) of "ASAHIMEAST", a yeast extract, 0.1% (w/v) of dipotassium phosphate, 0.06% (w/v) of sodium phosphate dodecahydrate, 0.05% (w/v) magnesium sulfate heptahydrate, and water was placed in 500-ml Erlenmeyer flasks in a volume of 100 ml each, autoclaved at 121° C. for 20 minutes to effect sterilization, cooled, inoculated with a stock culture of *Bacillus globisporus* N75, FERM BP-7591, and incubated at 27° C. for 48 hours under rotary shaking conditions of 230 rpm for use as a seed culture.

About 20L of a fresh preparation of the same nutrient culture medium as used in the above culture were placed in a 30-L fermentor, sterilized by heating, cooled to 27° C., inoculated with 1% (v/v) of the seed culture, and incubated for about 48 hours while stirring under aeration agitation conditions at 27° C. and pH 6.0–8.0. The resultant culture, having about 0.34 unit/ml of α-isomaltosylglucosaccharide-forming enzyme activity, about 1.1 units/ml of α-isomaltosyl-transferring enzyme activity, and about 0.69 unit/ml of cyclotetrasaccharide-forming enzyme activity, was centrifuged at 10,000 rpm for 30 min to obtain about 18L of a supernatant. Measurement of the supernatant revealed that it had about 0.33 unit/ml of α-isomaltosylglucosaccharide-forming enzyme activity, i.e., a total enzyme activity of about 5,940 units; about 1.1 units/ml of α-isomaltosyl-transferring enzyme activity, i.e., a total enzyme activity of about 19,800 units; and about 0.67 unit/ml of cyclotetrasaccharide-forming enzyme activity, i.e., a total enzyme activity of about 12,100 units.

Experiment 11

Preparation of Enzyme from *Bacillus Globisporus* N75

An 18L of the supernatant obtained in Experiment 10 was salted out with a 60% saturated ammonium sulfate solution and allowed to stand at 4° C. for 24 hours. Then, the salted out sediments were collected by centrifugation at 10,000 for 30 min, dissolved in 10 mM Tris-HCl buffer (pH 8.3), dialyzed against a fresh preparation of the same buffer to obtain about 450 ml of a crude enzyme solution. The crude enzyme solution was revealed to have 4,710 units of the α-isomaltosylglucosaccharide-forming enzyme, about 15,700 units of α-isomaltosyl-transferring enzyme, and about 9,590 units of cyclotetrasaccharide-forming enzyme, followed by subjecting it to ion-exchange chromatography using "SEPABEADS FP-DA13" gel, disclosed in Experiment 4-1. The enzyme was adsorbed on the gel, while α-isomaltosyl-transferring enzyme was eluted as a non-adsorbed fraction without adsorption on the gel. When eluted with a linear gradient increasing from 0M to 1M NaCl, the α-isomaltosylglucosaccharide-forming enzyme of the present invention was eluted at a concentration of about 0.25M NaCl. Under these conditions, fractions with the α-isomaltosylglucosaccharide-forming enzyme activity of the present invention and those with α-isomaltosyl-transferring enzyme were separately fractionated and collected. Similarly as in the case of *Bacillus globisporus* C9 in Experiment 4 and *Bacillus globisporus* C11 in Experiment 7, it was revealed that no cyclotetrasaccharide-forming activity was found in any fraction in this column chromatography, and an enzyme solution, obtained by mixing both fractions of α-isomaltosylglucosaccharide-forming enzyme and of α-isomaltosyl-transferring enzyme, showed cyclotetrasaccharide-forming activity, and these facts revealed that the activity of forming cyclotetrasaccharide from partial starch hydrolyzates is exerted by the coaction of the α-isomaltosylglucosaccharide-forming enzyme of the present invention and α-isomaltosyl-transferring enzyme.

The following experiments describe a method of separately purifying the α-isomaltosylglucosaccharide-forming enzyme of the present invention and α-isomaltosyl-transferring enzyme:

Experiment 11-2

Purification of α-isomaltosylglucosaccharide-forming Enzyme

The above fractions with the α-isomaltosylglucosaccharide-forming enzyme of the present invention were pooled and then dialyzed against 10 mM phosphate buffer (pH 7.0) containing 1M ammonium sulfate, and the dialyzed solution was centrifuged to remove impurities and fed to affinity chromatography using 500 ml of "SEPHACRYL HR S-200" gel. The enzyme was adsorbed on the gel and then eluted therefrom sequentially with a linear gradient decreasing from 1M to 0M ammonium sulfate and with a linear gradient increasing from 0 mM to 100 mM maltotetraose. As a result, the α-isomaltosylglucosaccharide-forming enzyme adsorbed on the gel was eluted therefrom at a concentration of about 30 mM maltotetraose, followed by collecting fractions with the enzyme activity. The fractions were pooled and dialyzed against 10 mM phosphate buffer (pH 7.0) containing 1M ammonium sulfate, and the dialyzed solution was centrifuged to remove impurities. The resulting supernatant was fed to hydrophobic chromatography using 350 ml of "BUTYL-TOYOPEARL 650M", a gel commercialized by Tosoh Corporation, Tokyo, Japan. The enzyme was adsorbed on the gel and then eluted with a linear gradient decreasing from 1M to 0M ammonium sulfate, resulting in an elution of the enzyme from the gel at a concentration of about 0.3M ammonium sulfate and collecting fractions with the enzyme activity. The fractions were pooled and dialyzed against 10 mM phosphate buffer (pH 7.0) containing 1M ammonium sulfate, and the dialyzed solution was centrifuged to remove impurities and purified on affinity chromatography using 350 ml of "SEPHACRYL HR S-200" gel. The amount of enzyme activity, specific activity, and yield of the α-isomaltosylglucosaccharide-forming enzyme in each purification step are in Table 11.

TABLE 11

| Purification step | Enzyme* activity (unit) | Specific activity of enzyme* (unit/mg protein) | Yield (%) |
| --- | --- | --- | --- |
| Culture supernatant | 5,940 | 0.10 | 100 |
| Dialyzed solution after salting out with ammonium sulfate | 4,710 | 0.19 | 79.3 |
| Eluate from ion-exchange column chromatography | 3,200 | 2.12 | 53.9 |
| Eluate from affinity column chromatography | 2,210 | 7.55 | 37.2 |
| Eluate from hydrophobic column chromatography | 1,720 | 10.1 | 29.0 |
| Eluate from affinity column chromatography | 1,320 | 12.5 | 22.2 |

Note:
The symbol "*" means α-isomaltosylglucosaccharide-forming enzyme.

The final purified α-isomaltosylglucosaccharide-forming enzyme specimen was assayed for purity on gel electrophoresis using a 7.5% (w/v) polyacrylamide gel and detected on the gel as a single protein band, meaning a high purity enzyme specimen.

Experiment 11-3

Purification of α-isomaltosyl-transferring Enzyme

Fractions of α-isomaltosyl-transferring enzyme, which had been separated from fractions of α-isomaltosylglucosaccharide-forming enzyme by ion-exchange chromatography in Experiment 11-1, were pooled and dialyzed against 10 mM phosphate buffer (pH 7.0) containing 1M ammonium sulfate, and the dialyzed solution was centrifuged to remove impurities. The resulting supernatant was fed affinity column chromatography using 500 ml of "SEPHACRYL HR S-200", a gel commercialized by Amersham Corp., Div. Amersham International, Arlington Heights, Ill., USA. The enzyme was adsorbed on the gel and then eluted with a linear gradient decreasing from 1M to 0M of ammonium sulfate, resulting in an elution of the enzyme from the gel at a concentration of about 0.3M ammonium sulfate and collecting fractions with the enzyme activity. The fractions were pooled and dialyzed against 10 mM phosphate buffer (pH 7.0) containing 1M ammonium sulfate, and the dialyzed solution was centrifuged to remove impurities and purified on hydrophobic chromatography using 380 ml of "BUTYL-TOYOPEARL 650M" gel. The enzyme was adsorbed on the gel and then eluted therefrom with a linear gradient decreasing from 1M to 0M ammonium sulfate, resulting in an elution of the enzyme at a concentration of about 0.3M ammonium sulfate. The fractions with the enzyme activity were pooled and dialyzed against 10 mM Tris-HCl buffer (pH 8.0), and the dialyzed solution was centrifuged to remove impurities. The resulting supernatant was fed to ion-exchange column chromatography using 380 ml of "SUPER Q-TOYOPEARL 650C" gel commercialized by Tosoh Corporation, Tokyo, Japan. The enzyme was not adsorbed on the gel and then eluted as non-adsorbed fractions which were then collected and pooled to obtain a final purified enzyme preparation. The amount of enzyme activity, specific activity, and yield of the α-isomaltosylglucosaccharide-forming enzyme in each purification step are in Table 12.

TABLE 12

| Purification step | Enzyme* activity (unit) | Specific activity of enzyme* (unit/mg protein) | Yield (%) |
| --- | --- | --- | --- |
| Culture supernatant | 19,000 | 0.33 | 100 |
| Dialyzed solution after salting out with ammonium sulfate | 15,700 | 0.64 | 82.6 |
| Eluate from ion-exchange column chromatography | 12,400 | 3.56 | 65.3 |
| Eluate from affinity column chromatography | 8,320 | 11.7 | 43.8 |
| Eluate from hydrophobic column chromatography | 4,830 | 15.2 | 25.4 |
| Eluate from ion-exchange column chromatography | 3,850 | 22.6 | 20.3 |

Note:
The symbol "*" means α-isomaltosyl-transferring enzyme.

The final purified α-isomaltosyl-transferring enzyme specimen was assayed for purity on gel electrophoresis using a 7.5% (w/v) polyacrylamide gel and detected on the gel as a single protein band, meaning a high purity enzyme specimen.

Experiment 12

Property of α-isomaltosylglucosaccharide-forming Enzyme and α-isomaltosyl-transferring Enzyme Experiment 12-1

Property of α-isomaltosylglucosaccharide-forminq enzyme

A purified specimen of α-isomaltosylglucosaccharide-forming enzyme, obtained by the method in Experiment 11-2, was subjected to SDS-PAGE using a 7.5% (w/v) of polyacrylamide gel and then determined for molecular weight by comparing with the dynamics of standard molecular markers electrophoresed in parallel, commercialized by Bio-Rad Laboratories Inc., Brussels, Belgium, revealing that the enzyme had a molecular weight of about 136,000±20,000 daltons.

A fresh preparation of the above purified specimen was subjected to isoelectrophoresis using a gel containing 2% (w/v) ampholine commercialized by Amersham Corp., Div. Amersham International, Arlington Heights, Ill., USA, and then measured for pHs of protein bands and gel to determine the isoelectric point of the enzyme, revealing that the enzyme had an isoelectric point of about 7.3±0.5.

The influence of temperature and pH on the activity of α-isomaltosylglucosaccharide-forming enzyme was examined in accordance with the assay for the enzyme activity, where the influence of temperature was conducted in the presence or absence of 1 mM $Ca^{2+}$. These results are in FIG.

Figure 22:
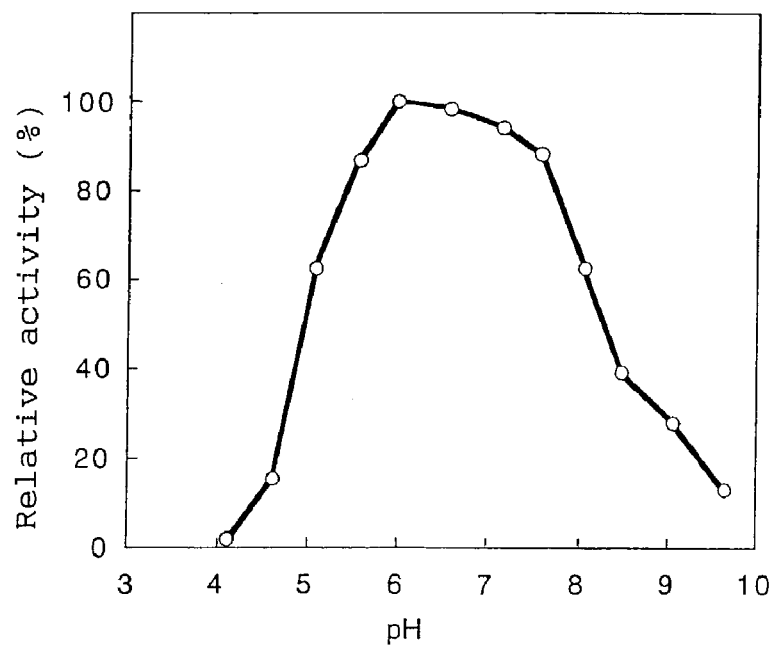
FIG. 22 shows the pH influence on the enzymatic activity of α-isomaltosylglucosaccharide-forming enzyme from a microorganism of the species *Bacillus globisporus* N75 strain.
Figure 23:
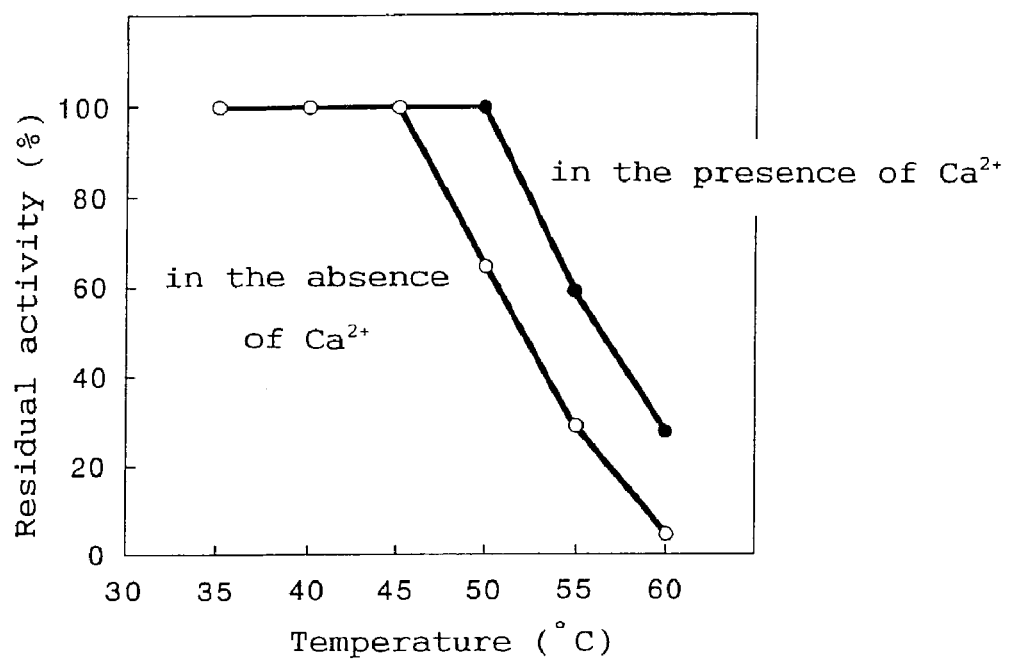
FIG. 23 shows the thermal stability of α-isomaltosylglucosaccharide-forming enzyme from a microorganism of the species *Bacillus globisporus* N75 strain.
Figure 24:
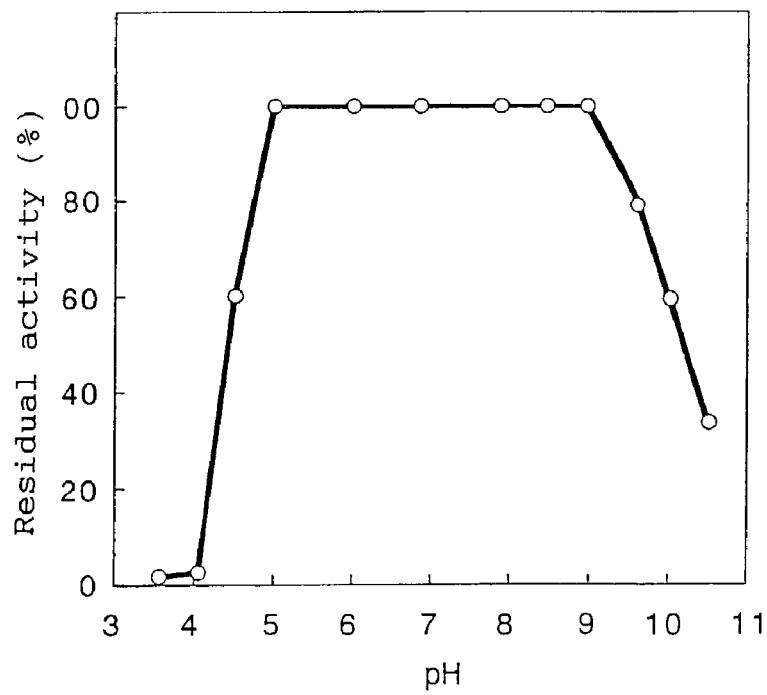
FIG. 24 shows the pH stability of α-isomaltosylglucosaccharide-forming enzyme from a microorganism of the species *Bacillus globisporus* N75 strain.

21 (influence of temperature) and FIG. 22 (influence of pH). The optimum temperature of the enzyme was about 50° C. and about 55° C. when incubated at pH 6.0 for 60 min in the absence of and in the presence of 1 mM $Ca^{2+}$, respectively. The optimum pH of the enzyme was about 6.0 when incubated at 35° C. for 60 min. The thermal stability of the enzyme was determined by incubating the testing enzyme solutions in 20 mM acetate buffer (pH 6.0) at prescribed temperatures for 60 min in the absence of and in the presence of 1 mM $Ca^{2+}$, cooling with water the resulting enzyme solutions, and assaying the remaining enzyme activity of each solution. The pH stability of the enzyme was determined by keeping the testing enzyme solutions in 50 mM buffers having prescribed pHs at 4° C. for 24 hours, adjusting the pH of each solution to 6.0, and assaying the remaining enzyme activity of each solution. These results are respectively in FIG. 23 (thermal stability) and FIG. 24 (pH stability). As a result, the enzyme had thermal stability of up to about 45° C. and about 50° C. in the absence of and in the presence of 1 mM $Ca^{2+}$, respectively, and had pH stability of about 5.0 to about 9.0.

The influence of metal ions on the activity of α-isomaltosylglucosaccharide-forming enzyme was examined in the presence of 1 mM of each metal-ion according to the assay for the enzyme activity. The results are in Table 13.

TABLE 13

| Metal ion | Relative activity (%) | Metal ion | Relative activity (%) |
|---|---|---|---|
| None | 100 | $Hg^{2+}$ | 1 |
| $Zn^{2+}$ | 82 | $Ba^{2+}$ | 84 |
| $Mg^{2+}$ | 96 | $Sr^{2+}$ | 85 |
| $Ca^{2+}$ | 108 | $Pb^{2+}$ | 86 |
| $Co^{2+}$ | 93 | $Fe^{2+}$ | 82 |
| $Cu^{2+}$ | 7 | $Fe^{3+}$ | 93 |
| $Ni^{2+}$ | 93 | $Mn^{2+}$ | 120 |
| $Al^{3+}$ | 98 | EDTA | 35 |

As evident from the results in Table 13, the enzyme activity was greatly inhibited by $Hg^{2+}$, $Cu^{2+}$, and EDTA. It was also found that the enzyme was activated by $Ca^{2+}$ and $Mn^{2+}$.

Amino acid analysis of the N-terminal amino acid sequence of the enzyme by "PROTEIN SEQUENCER MODEL 473A", an apparatus of Applied Biosystems, Inc., Foster City, USA, revealed that the enzyme had a partial amino acid sequence of SEQ ID NO:11, i.e., histidine-valine-serine-alanine-leucine -glycine-asparagine-leucine-leucine in the N-terminal region.

Comparison of the above partial amino acid sequence in the N-terminal region with that derived from the α-isomaltosylglucosaccharide-forming enzyme from *Bacillus globisporus* C11 in Experiment 8-1 revealed that they had a relatively high homology but differed in the amino acid residues 1, 4 and 9.

Experiment 12-2

Property of α-isomaltosylglucosaccharide-forming Enzyme and α-isomaltosyl-transferring Enzyme A purified specimen of α-isomaltosyl-transferring enzyme, obtained by the method in Experiment 11-3, was subjected to SDS-PAGE using a 7.5% (w/v) of polyacrylamide gel and then determined for molecular weight by comparing with the dynamics of standard molecular markers electrophoresed in parallel, commercialized by Bio-Rad Laboratories Inc., Brussels, Belgium, revealing that the enzyme had a molecular weight of about 112,000±20,000 daltons.

A fresh preparation of the above purified specimen was subjected to isoelectrophoresis using a gel containing 2% (w/v) ampholine commercialized by Amersham Corp., Div. Amersham International, Arlington Heights, Ill., USA, and then measured for pHs of protein bands and gel to determine the isoelectric point of the enzyme, revealing that the enzyme had an isoelectric point of about 7.8±0.5.

Figure 25:
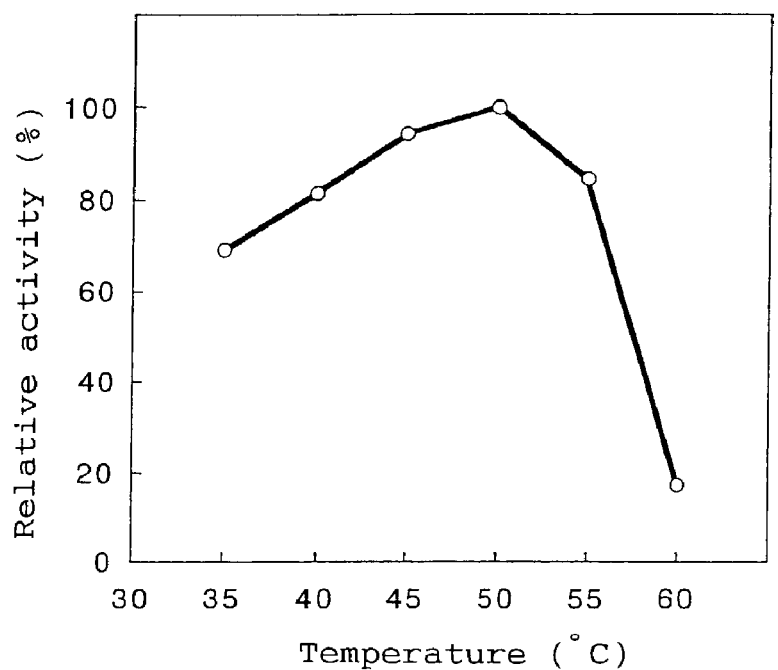
FIG. 25 shows the thermal influence on the enzymatic activity of α-isomaltosyl-transferring enzyme from a microorganism of the species *Bacillus globisporus* N75 strain.
Figure 26:
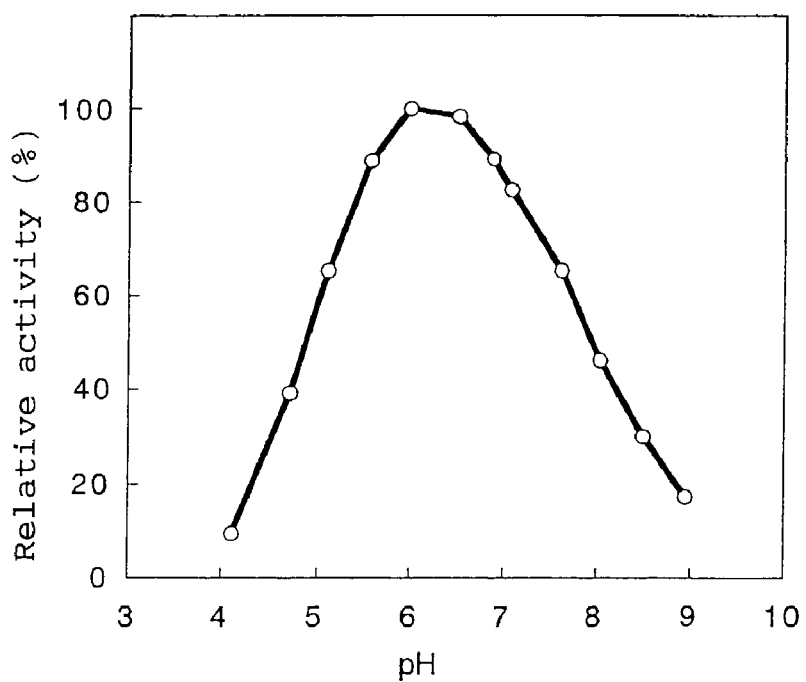
FIG. 26 shows the pH influence on the enzymatic activity of α-isomaltosyl-transferring enzyme from a microorganism of the species *Bacillus globisporus* N75 strain.
Figure 27:
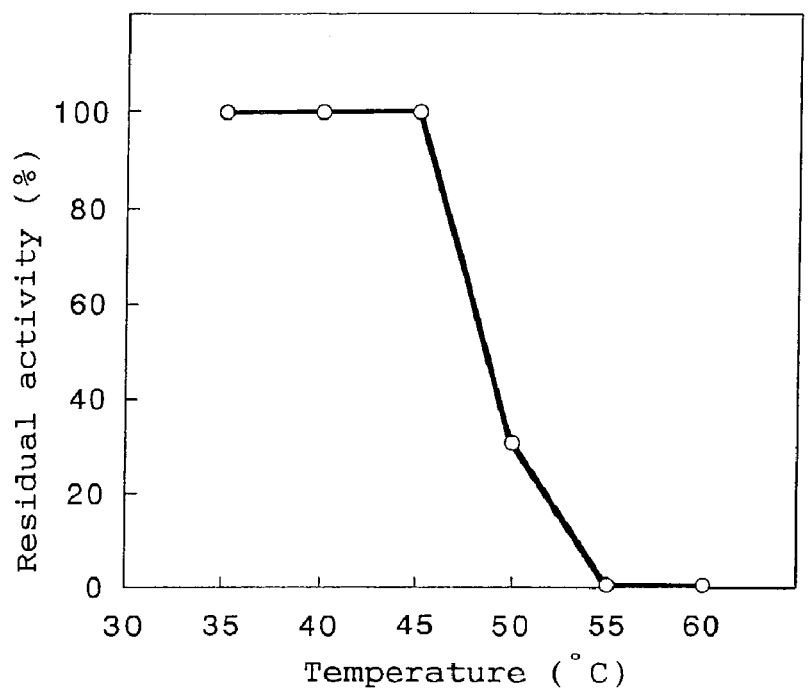
FIG. 27 shows the thermal stability of α-isomaltosyl-transferring enzyme from a microorganism of the species *Bacillus globisporus* N75 strain.
Figure 28:
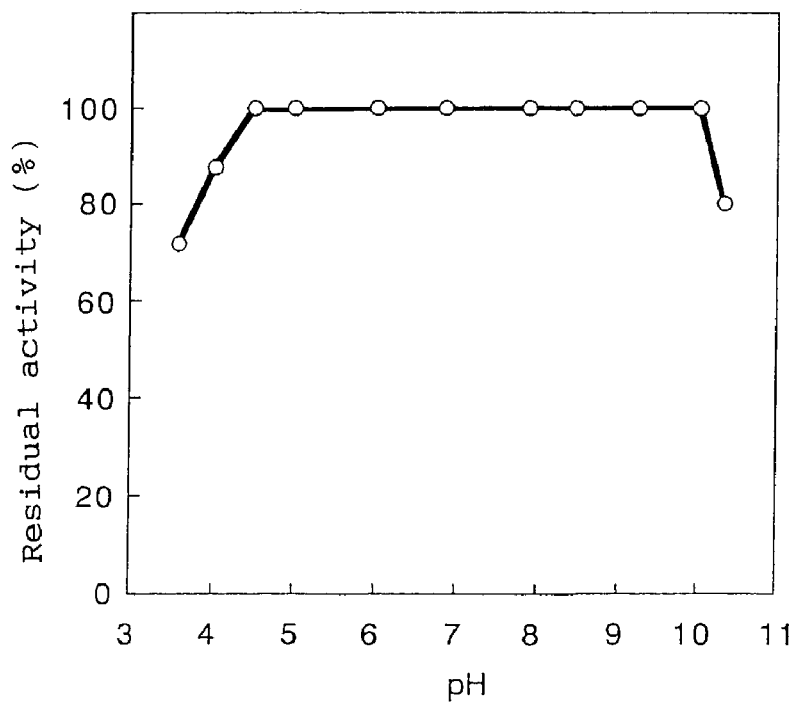
FIG. 28 shows the pH stability of α-isomaltosyl-transferring enzyme from a microorganism of the species *Bacillus globisporus* N75 strain.

The influence of temperature and pH on the activity of α-isomaltosyl-transferring enzyme was examined in accordance with the assay for the enzyme activity. These results are in FIG. 25 (influence of temperature) and FIG. 26 (influence of pH). The optimum temperature of the enzyme was about 50° C. The optimum pH of the enzyme was about 6.0 when incubated at 35° C. for 30 min. The thermal stability of the enzyme was determined by incubating the testing enzyme solutions in 20 mM acetate buffer (pH 6.0) at prescribed temperatures for 60 min, cooling with water the resulting enzyme solutions, and assaying the remaining enzyme activity of each solution. The pH stability of the enzyme was determined by keeping the testing enzyme solutions in 50 mM buffers having prescribed pHs at 4° C. for 24 hours, adjusting the pH of each solution to 6.0, and assaying the remaining enzyme activity of each solution. These results are respectively in FIG. 27 (thermal stability) and FIG. 28 (pH stability). As a result, the enzyme had thermal stability of up to about 45° C. and had pH stability of about 4.5 to about 10.0.

The influence of metal ions on the activity of α-isomaltosyl-transferring enzyme was examined in the presence of 1 mM of each metal-ion according to the assay for the enzyme activity. The results are in Table 14.

TABLE 14

| Metal ion | Relative activity (%) | Metal ion | Relative activity (%) |
|---|---|---|---|
| None | 100 | $Hg^{2+}$ | 0.5 |
| $Zn^{2+}$ | 75 | $Ba^{2+}$ | 102 |
| $Mg^{2+}$ | 95 | $Sr^{2+}$ | 91 |
| $Ca^{2+}$ | 100 | $Pb^{2+}$ | 69 |
| $Co^{2+}$ | 92 | $Fe^{2+}$ | 97 |
| $Cu^{2+}$ | 15 | $Fe^{3+}$ | 90 |
| $Ni^{2+}$ | 91 | $Mn^{2+}$ | 101 |
| $Al^{3+}$ | 94 | EDTA | 92 |

As evident from the results in Table 14, the enzyme activity was greatly inhibited by $Hg^{2+}$ and was also inhibited by $Cu^{2+}$. It was also found that the enzyme was not activated by $Ca^{2+}$ and not inhibited by EDTA.

Amino acid analysis of the N-terminal amino acid sequence of the enzyme by "PROTEIN SEQUENCER MODEL 473A", an apparatus of Applied Biosystems, Inc., Foster City, USA, revealed that the enzyme had a partial amino acid sequence of SEQ ID NO:3, i.e., isoleucine-aspartic acid-glycine-valine-tyrosine-histidine-alanine-proline-tyrosine-glycine at the N-terminal region.

Comparison of the above partial amino acid sequence at the N-terminal region with that derived from the α-isomaltosylglucosaccharide-forming enzyme from *Bacillus globisporus* C9 in Experiment 8-2 revealed that they had a common amino acid sequence of isoleucine-aspartic acid-glycine-valine-tyrosine-histidine-alanine-proline, as shown in SEQ ID NO:4 at their N-terminal regions.

Experiment 13

Internal Amino Acid Sequence of α-isomaltosylglucosaccharide-forming Enzyme and α-isomaltosyl-transferring Enzyme Experiment 13-1

Internal Amino Acid Sequence of α-isomaltosylglucosaccharide-forming Enzyme

A part of a purified specimen of α-isomaltosylglucosaccharide-forming enzyme, obtained by the method in Experiment 11-2, was dialyzed against 10 mM Tris-HCl buffer (pH 9.0), and the dialyzed solution was diluted with a fresh preparation of the same buffer to give a concentration of about one milligram per milliliter. One milliliter of the dilute as a test sample was admixed with 20 µg of "Lysyl Endopeptidase" commercialized by Wako Pure Chemical Industries, Ltd., Tokyo, Japan, and allowed to react at 30° C. for 24 hours to form peptides. The resultant mixtures were subjected to reverse-phase HPLC to separate the peptides using "µ-Bondasphere C18 column" having a diameter of 3.9 mm and a length of 150 mm, a product of Waters Chromatography Div., MILLIPORE Corp., Milford, USA, at a flow rate of 0.9 ml/min and at ambient temperature, and using a liner gradient of acetonitrile increasing from 8% (v/v) to 36% (v/v) in 0.1% (v/v) trifluoroacetate over 120 min. The peptides eluted from the column were detected by monitoring the absorbency at a wavelength of 210 nm. Three peptide specimens named PN59 with a retention time of about 59 min, PN67 with a retention time of about 67 min, and PN87 with a retention time of about 87 min, which had been well separated from other peptides, were separately collected and dried in vacuo and then dissolved in 200 µl of a solution of 0.1% (v/v) trifluoroacetate and 50% (v/v) acetonitrile. Each peptide specimen was subjected to a protein sequencer for analyzing amino acid sequence up to eight amino acid residues to obtain amino acid sequences of SEQ ID NOs:12 to 14. The analyzed internal partial amino acid sequences are in Table 15.

TABLE 15

| Peptide name | Internal partial amino acid sequence |
| --- | --- |
| PN59 | aspartic acid-phenylalanine-serine-asparagine-asparagine-proline-threonine-valine<br>SEQ ID NO:12 |
| PN67 | tyrosine-threonine-valine-asparagine-alanine-proline-alanine-alanine<br>SEQ ID NO:13 |
| PN87 | tyrosine-glutamic acid-alanine-glutamic acid-serine-alanine-glutamic acid-leucine<br>SEQ ID NO:14 |

Experiment 13-2

Internal Amino Acid Sequence of α-isomaltosyl-transferring Enzyme

A part of a purified specimen of α-isomaltosyl-transferring enzyme, obtained by the method in Experiment 11-3, was dialyzed against 10 mM Tris-HCl buffer (pH 9.0), and the dialyzed solution was diluted with a fresh preparation of the same buffer to give a concentration of about one milligram per milliliter. One milliliter of the dilute as a test sample was admixed with 20 µg of "Lysyl Endopeptidase" commercialized by Wako Pure Chemical Industries, Ltd., Tokyo, Japan, and allowed to react at 30° C. for 24 hours to form peptides. The resultant mixtures were subjected to reverse-phase HPLC to separate the peptides using "µ-Bondasphere C18 column" having a diameter of 3.9 mm and a length of 150 mm, a product of Waters Chromatography Div., MILLIPORE Corp., Milford, USA, at a flow rate of 0.9 ml/min and at ambient temperature, and using a liner gradient of acetonitrile increasing from 4% (v/v) to 42.4% (v/v) in 0.1% (v/v) trifluoroacetate over 90 min. The peptides eluted from the column were detected by monitoring the absorbency at a wavelength of 210 nm. Three peptide specimens named PN21 with a retention time of about 21 min, PN38 with a retention time of about 38 min, and PN69 with a retention time of about 69 min, which had been well separated from other peptides, were separately collected and dried in vacuo and then dissolved in 200 µl of a solution of 0.1% (v/v) trifluoroacetate and 50% (v/v) acetonitrile. Each peptide specimen was subjected to a protein sequencer for analyzing amino acid sequence up to eight amino acid residues, but up to six amino acids residues for PN21, to obtain amino acid sequences of SEQ ID NOs: 15 to 17. The analyzed internal partial amino acid sequences are in Table 16.

TABLE 16

| Peptide name | Internal partial amino acid sequence |
| --- | --- |
| PN21 | asparagine-tryptophane-tryptophane-methionine-serine-lysine<br>SEQ ID NO:15 |
| PN38 | threonine-aspartic acid-glycine-glycine-glutamic acid-methionine-valine-tryptophan<br>SEQ ID NO:16 |
| PN69 | asparagine-isoleucine-tyrosine-leucine-proline-glutamine-glycine-aspartic acid<br>SEQ ID NO:17 |

Experiment 14

Production of α-isomaltosylglucosaccharide-forminq Enzyme from *Arthrobacter Globiformis* A19 (Strain A19)

A liquid nutrient culture medium, consisting of 4.0% (w/v) of "PINE-DEX #4", a partial starch hydrolysate, 1.8% (w/v) of "ASAHIMEAST", a yeast extract, 0.1% (w/v) of dipotassium phosphate, 0.06% (w/v) of sodium phosphate dodecahydrate, 0.05% (w/v) magnesium sulfate heptahydrate, and water was placed in 500-ml Erlenmeyer flasks in a volume of 100 ml each, autoclaved at 121° C. for 20 minutes to effect sterilization, cooled, inoculated with a stock culture of *Arthrobacter globiformis* A19, FERM BP-7590, and incubated at 27° C. for 48 hours under rotary shaking conditions of 230 rpm for use as a seed culture.

About 20L of a fresh preparation of the same nutrient culture medium as used in the above culture were placed in a 30-L fermentor, sterilized by heating, cooled to 27° C., inoculated with 1% (v/v) of the seed culture, and incubated for about 48 hours while stirring under aeration agitation conditions at 27° C. and pH 6.0–9.0. The resultant culture, having about 1.1 units/ml of α-isomaltosylglucosaccharide-forming enzyme activity, about 1.7 units/ml of α-isomaltosyl-transferring enzyme activity, and about 0.35 unit/ml of cyclotetrasaccharide-forming enzyme activity, was centrifuged at 10,000 rpm for 30 min to obtain about 18L of a supernatant. Measurement of the supernatant revealed that it had about 1.06 units/ml of α-isomaltosylglucosaccharide-forming enzyme activity, i.e., a total enzyme activity of about 19,100 units; about 1.6 units/ml of α-isomaltosyl-transferring enzyme activity, i.e., a total enzyme activity of about 28,800 units; and about 0.27 unit/ml of cyclotetrasaccharide-forming enzyme activity, i.e., a total enzyme activity of about 4,860 units.

The activity of the α-isomaltosylglucosaccharide-forming enzyme from *Arthrobacter globiformis* A19 was similarly assayed as the method in Experiment 3 except for using 100 mM glycine-NaOH buffer (pH 8.4) was used as a buffer for substrate.

Experiment 15

Preparation of Enzyme from *Arthrobacter Globiformis* A19

About 18L of the supernatant, obtained in Experiment 14, was salted out with a 60% saturated ammonium sulfate solution and allowed to stand at 4° C. for 24 hours. Then, the salted out sediments were collected by centrifugation at 10,000 for 30 min, dissolved in 10 mM phosphate buffer (pH 7.0), dialyzed against a fresh preparation of the same buffer to obtain about 850 ml of a crude enzyme solution. The crude enzyme solution was revealed to have 8,210 units of the α-isomaltosylglucosaccharide-forming enzyme, about 15,700 units of α-isomaltosyl-transferring enzyme, and about 20,090 units of cyclotetrasaccharide-forming enzyme, followed by subjecting it to ion-exchange chromatography using 380 ml of "DEAE-TOYOPEARL 650S" gel. When eluted with a linear gradient increasing from 0M to 0.5M NaCl, the above enzyme and α-isomaltosyl-transferring enzyme were separately eluted from the gel, the former was eluted at a concentration of about 0.2M NaCl, while the latter was eluted at a concentration of about 0.3M NaCl. Under these conditions, fractions with the α-isomaltosylglucosaccharide-forming enzyme activity of the present invention and those with α-isomaltosyl-transferring enzyme were separately fractionated and collected. Since the facts that no cyclotetrasaccharide-forming activity was found in any fraction in this column chromatography, and an enzyme solution, obtained by mixing fractions of α-isomaltosylglucosaccharide-forming enzyme and of α-isomaltosyl-transferring enzyme, showed cyclotetrasaccharide-forming activity, it was revealed that the activity of forming cyclotetrasaccharide from partial starch hydrolyzates is exerted by the coaction of the α-isomaltosylglucosaccharide-forming enzyme of the present invention and α-isomaltosyl-transferring enzyme.

The following experiments describe a method of separately purifying the α-isomaltosylglucosaccharide-forming enzyme of the present invention and α-isomaltosyl-transferring enzyme:

Experiment 15-2

Purification of α-isomaltosylglucosaccharide-forming Enzyme

The above fractions with the α-isomaltosylglucosaccharide-forming enzyme of the present invention were pooled and then dialyzed against 10 mM phosphate buffer (pH 7.0) containing 1M ammonium sulfate, and the dialyzed solution was centrifuged to remove impurities and fed to affinity chromatography using 500 ml of "SEPHACRYL HR S-200" gel. The enzyme was adsorbed on the gel and then eluted therefrom with a linear gradient decreasing from 1M to 0M ammonium sulfate. As a result, the α-isomaltosylglucosaccharide-forming enzyme adsorbed on the gel was eluted therefrom at a concentration of about 0.2M ammonium sulfate, followed by collecting fractions with the enzyme activity and pooling them for use as a final purified specimen. The amount of enzyme activity, specific activity, and yield of the α-isomaltosylglucosaccharide-forming enzyme in each purification step are in Table 17.

TABLE 17

| Purification step | Enzyme* activity (unit) | Specific activity of enzyme* (unit/mg protein) | Yield (%) |
|---|---|---|---|
| Culture supernatant | 19,100 | 0.11 | 100 |
| Dialyzed solution after salting out with ammonium sulfate | 8,210 | 0.48 | 43.0 |
| Eluate from ion-exchange column chromatography | 6,890 | 4.18 | 36.1 |
| Eluate from affinity column chromatography | 5,220 | 35.1 | 27.3 |

Note:
The symbol "*" means α-isomaltosylglucosaccharide-forming enzyme.

The final purified α-isomaltosylglucosaccharide-forming enzyme specimen was assayed for purity on gel electrophoresis using a 7.5% (w/v) polyacrylamide gel and detected on the gel as a single protein band, i.e., a high purity enzyme specimen.

Experiment 15-3

Purification of α-isomaltosyl-transferring Enzyme

Fractions of α-isomaltosyl-transferring enzyme, which had been separated from fractions of α-isomaltosylglucosaccharide-forming enzyme by ion-exchange chromatography in Experiment 15-1, were pooled and dialyzed against 10 mM phosphate buffer (pH 7.0) containing 1M ammonium sulfate, and the dialyzed solution was centrifuged to remove impurities. The resulting supernatant was fed affinity column chromatography using 500 ml of "SEPHACRYL HR S-200" gel, a gel commercialized by Amersham Corp., Div. Amersham International, Arlington Heights, Ill., USA. The enzyme was adsorbed on the gel and then eluted with a linear gradient decreasing from 1M to 0M of ammonium sulfate, resulting in an elution of the enzyme from the gel at a concentration of about 0M ammonium sulfate and collecting fractions with the enzyme activity for a partially purified specimen. The amount of enzyme activity, specific activity, and yield of the α-isomaltosyl-transferring enzyme in each purification step are in Table 18.

TABLE 18

| Purification step | Enzyme* activity (unit) | Specific activity of enzyme* (unit/mg protein) | Yield (%) |
|---|---|---|---|
| Culture supernatant | 28,800 | 0.18 | 100 |
| Dialyzed solution after salting out with ammonium sulfate | 15,700 | 0.97 | 54.5 |
| Eluate from ion-exchange column chromatography | 7,130 | 4.01 | 24.8 |
| Eluate from affinity column chromatography | 1,800 | 11.9 | 6.3 |

Note:
The symbol "*" means α-isomaltosyl-transferring enzyme.

The partially-purified α-isomaltosyl-transferring enzyme specimen was assayed for purity on gel electrophoresis using a 7.5% (w/v) polyacrylamide gel and detected on the gel as a main protein band along with three minor protein bands.

Experiment 16

Property of α-isomaltosylglucosaccharide-forming Enzyme and α-isomaltosyl-transferring Enzyme Experiment 16-1

Property of α-isomaltosylglucosaccharide-forming Enzyme

A purified specimen of α-isomaltosylglucosaccharide-forming enzyme, obtained by the method in Experiment 15-2, was subjected to SDS-PAGE using a 7.5% (w/v) of polyacrylamide gel and then determined for molecular weight by comparing with the dynamics of standard molecular markers electrophoresed in parallel, commercialized by Bio-Rad Laboratories Inc., Brussels, Belgium, revealing that the enzyme had a molecular weight of about 94,000±20,000 daltons.

A fresh preparation of the above purified specimen was subjected to isoelectrophoresis using a gel containing 2% (w/v) ampholine commercialized by Amersham Corp., Div. Amersham International, Arlington Heights, Ill., USA, and then measured for pHs of protein bands and gel to determine the isoelectric point of the enzyme, revealing that the enzyme had an isoelectric point of about 4.3±0.5.

Figure 29:
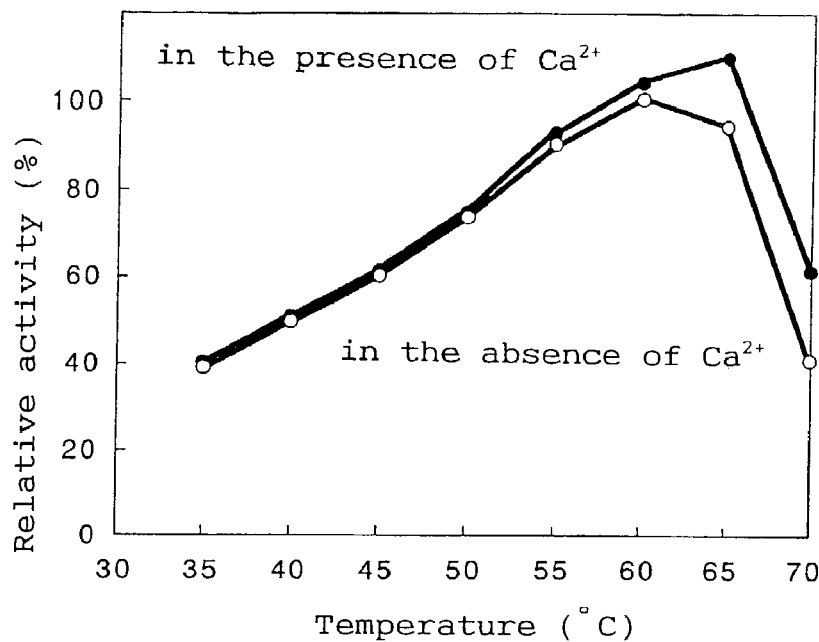
FIG. 29 shows the thermal influence on the enzymatic activity of α-isomaltosylglucosaccharide-forming enzyme from a microorganism of the species *Arthrobacter globiformis* A19 strain.
Figure 30:
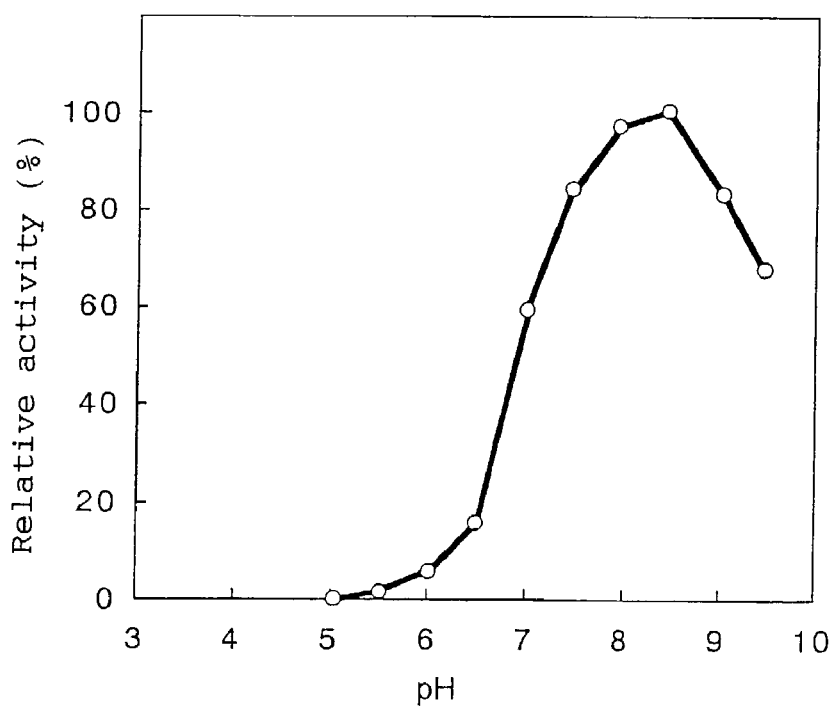
FIG. 30 shows the pH influence on the enzymatic activity of α-isomaltosylglucosaccharide-forming enzyme from a microorganism of the species *Arthrobacter globiformis* A19 strain.
Figure 31:
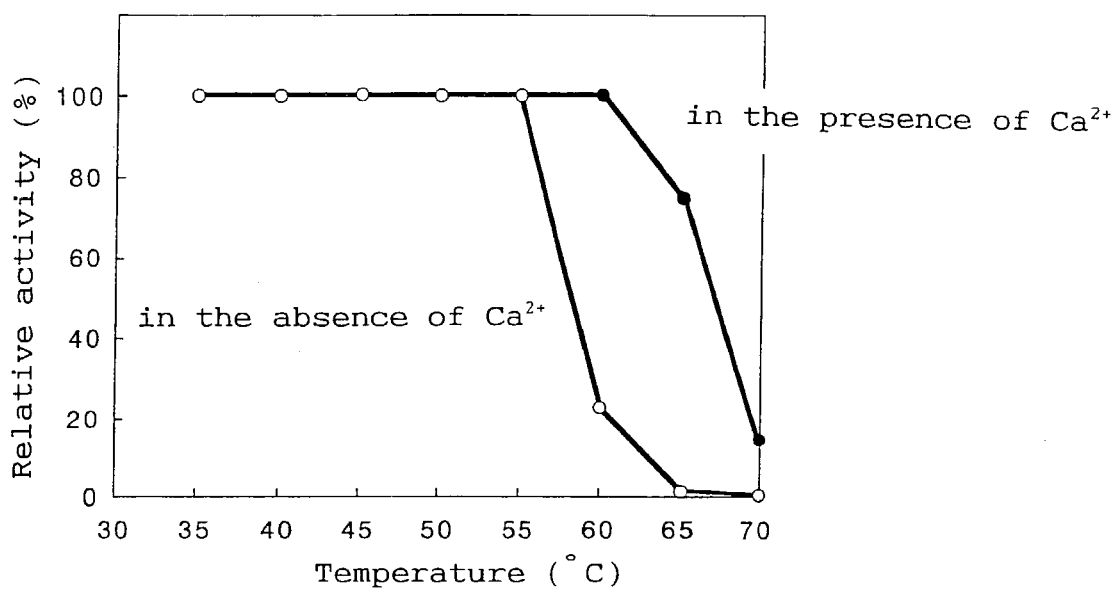
FIG. 31 shows the thermal stability of α-isomaltosylglucosaccharide-forming enzyme from a microorganism of the species *Arthrobacter globiformis* A19 strain.
Figure 32:
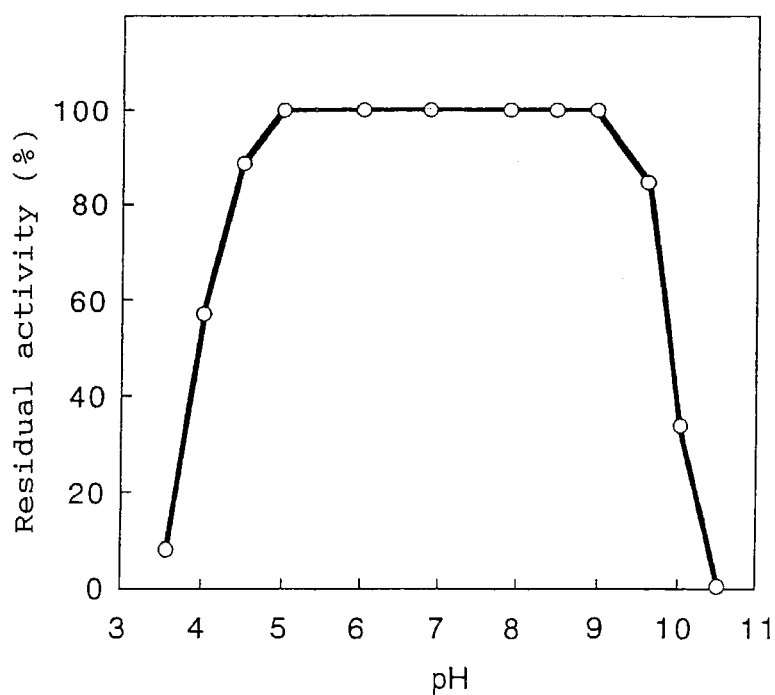
FIG. 32 shows the pH stability of α-isomaltosylglucosaccharide-forming enzyme from a microorganism of the species *Arthrobacter globiformis* A19 strain.

The influence of temperature and pH on the activity of α-isomaltosylglucosaccharide-forming enzyme was examined in accordance with the assay for the enzyme activity. The influence of temperature was determined in the presence of or in the absence of 1 mM $Ca^{2+}$. These results are in FIG. 29 (influence of temperature) and FIG. 30 (influence of pH). The optimum temperature of the enzyme was about 60° C. and about 65° C. in the absence of and in the presence of 1 mM $Ca^{2+}$, respectively. The optimum pH of the enzyme was about 8.4 when incubated at 35° C. for 60 min. The thermal stability of the enzyme was determined by incubating the testing enzyme solutions at prescribed temperatures for 60 min in 20 mM glycine-NaOH buffer (pH 8.0) and in the absence of or in the presence of 1 mM $Ca^2$, cooling with water the resulting enzyme solutions, and assaying the remaining enzyme activity of each solution. The pH stability of the enzyme was determined by keeping the testing enzyme solutions in 50 mM buffers having prescribed pHs at 4° C. for 24 hours, adjusting the pH of each solution to 8.0, and assaying the remaining enzyme activity of each solution. These results are respectively in FIG. 31 (thermal stability) and FIG. 32 (pH stability). As a result, the enzyme had thermal stability of up to about 55° C. and about 60° C. in the absence of and in the presence of 1 mM $Ca^{2+}$, respectively, and had pH stability of about 5.0 to about 9.0.

The influence of metal ions on the activity of α-isomaltosylglucosaccharide forming enzyme was examined in the presence of 1 mM of each metal-ion according to the assay for the enzyme activity. The results are in Table 19.

TABLE 19

| Metal ion | Relative activity (%) | Metal ion | Relative activity (%) |
|---|---|---|---|
| None | 100 | $Hg^{2+}$ | 0 |
| $Zn^{2+}$ | 56 | $Ba^{2+}$ | 99 |
| $Mg^{2+}$ | 97 | $Sr^{2+}$ | 102 |
| $Ca^{2+}$ | 106 | $Pb^{2+}$ | 43 |
| $Co^{2+}$ | 93 | $Fe^{2+}$ | 36 |
| $Cu^{2+}$ | 0 | $Fe^{3+}$ | 35 |
| $Ni^{2+}$ | 46 | $Mn^{2+}$ | 98 |
| $Al^{3+}$ | 37 | EDTA | 2 |

As evident from the results in Table 19, it was revealed that the enzyme activity was greatly inhibited by $Hg^{2+}$, $Cu^{2+}$ and EDTA.

Amino acid analysis of the N-terminal amino acid sequence of the enzyme by "PROTEIN SEQUENCER MODEL 473A", an apparatus of Applied Biosystems, Inc., Foster City, USA, revealed that the enzyme had a partial amino acid sequence of SEQ ID NO:18, i.e., alanine-proline-leucine-glycine-valine-glutamine-arginine-alanine-glutamine-phenylalanine-glutamine-serine-glycine at the N-terminal region.

Experiment 16-2

Property of α-isomaltosyl-transferring Enzyme

Figure 33:
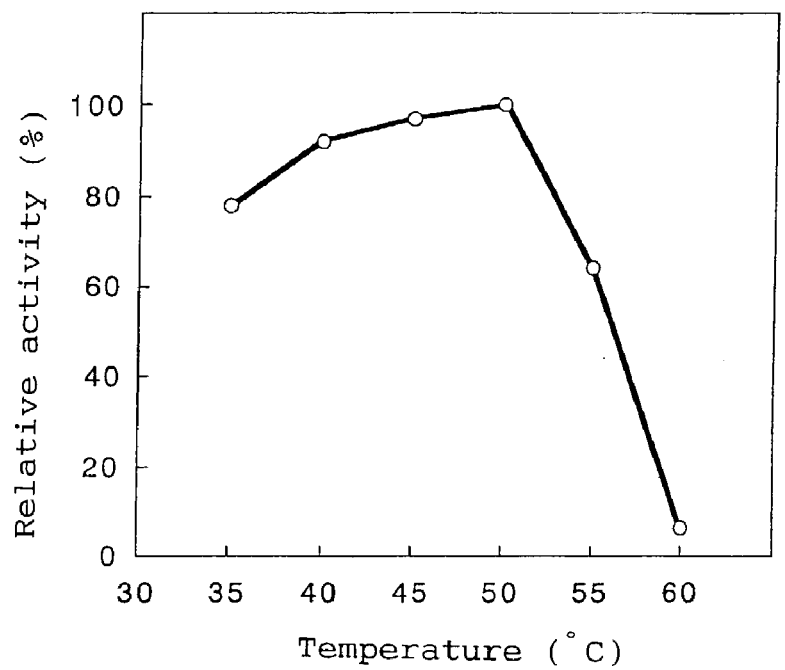
FIG. 33 shows the thermal influence on the enzymatic activity of α-isomaltosyl-transferring enzyme from a microorganism of the species *Arthrobacter globiformis* A19 strain.
Figure 34:
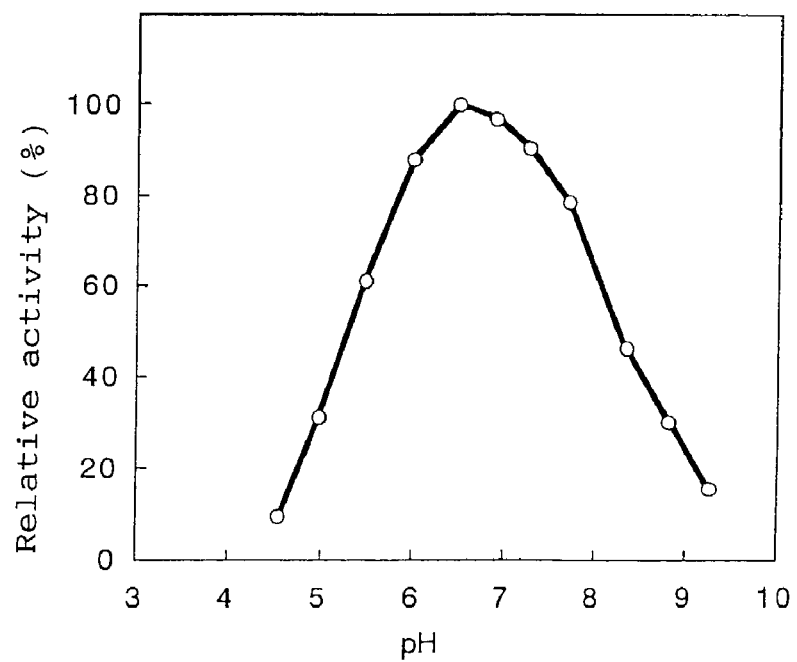
FIG. 34 shows the pH influence on the enzymatic activity of α-isomaltosyl-transferring enzyme from a microorganism of the species *Arthrobacter globiformis* A19 strain.
Figure 35:
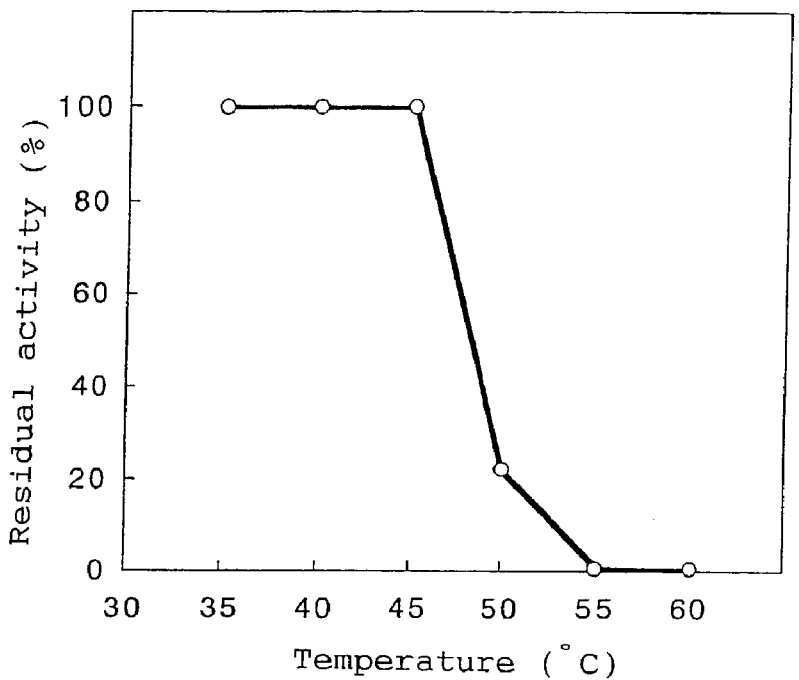
FIG. 35 shows the thermal stability of α-isomaltosyl-transferring enzyme from a microorganism of the species *Arthrobacter globiformis* A19 strain.
Figure 36:
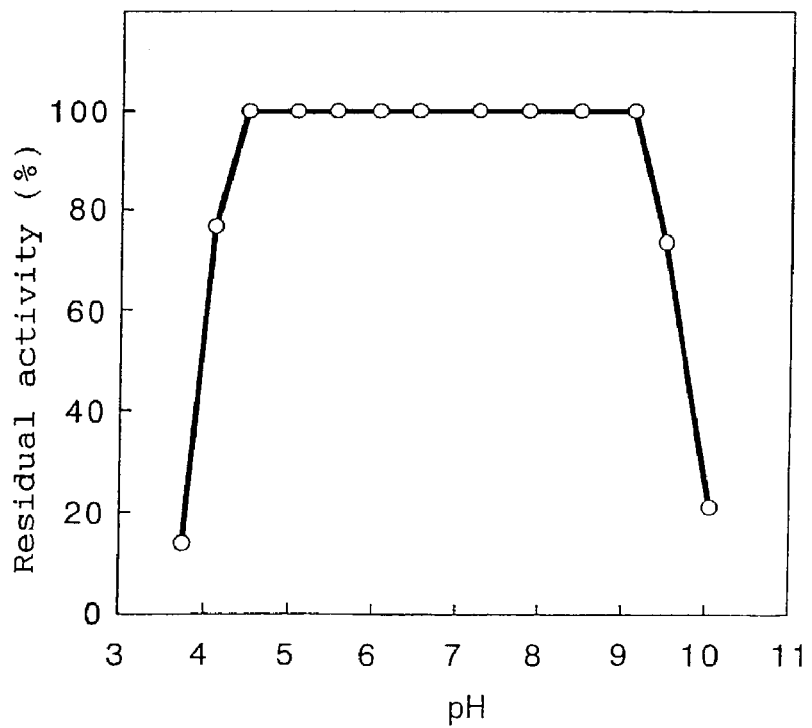
FIG. 36 shows the pH stability of α-isomaltosyl-transferring enzyme from a microorganism of the species *Arthrobacter globiformis* A19 strain.

Using a partially-purified specimen of α-isomaltosyl-transferring enzyme, obtained by the method in Experiment 15-3, the influence of temperature and pH on the enzyme was examined in accordance with the assay for the enzyme activity. These results are in FIG. 33 (influence of temperature) and FIG. 34 (influence of pH). The optimum temperature of the enzyme was about 50° C. when incubated at pH 6.0 for 30 min. The optimum pH of the enzyme was about 6.5 when incubated at 35° C. for 30 min. The thermal stability of the enzyme was determined by incubating the testing enzyme solutions in 20 mM acetate buffer (pH 6.0) at prescribed temperatures for 60 min, cooling with water the resulting enzyme solutions, and assaying the remaining enzyme activity of each solution. The pH stability of the enzyme was determined by keeping the testing enzyme solutions in 50 mM buffers having prescribed pHs at 4° C. for 24 hours, adjusting the pH of each solution to 6.0, and assaying the remaining enzyme activity of each solution. These results are respectively in FIG. 35 (thermal stability) and FIG. 36 (pH stability). As a result, the enzyme had thermal stability of up to about 45° C. and pH stability of about 4.5 to about 9.0.

Experiment 17

Production of α-isomaltosyl-transferring Enzyme from *Arthrobacter Ramosus* S1 (Strain S1)

A liquid nutrient culture medium, consisting of 4.0% (w/v) of "PINE-DEX #4", a partial starch hydrolysate, 1.8% (w/v) of "ASAHIMEAST", a yeast extract, 0.1% (w/v) of dipotassium phosphate, 0.06% (w/v) of sodium phosphate dodecahydrate, 0.05% (w/v) magnesium sulfate heptahydrate, and water was placed in 500-ml Erlenmeyer flasks in a volume of 100 ml each, autoclaved at 121° C. for 20 minutes to effect sterilization, cooled, inoculated with a stock culture of *Arthrobacter ramosus* S1, FERM BP-7592, and incubated at 27° C. for 48 hours under rotary shaking conditions of 230 rpm for use as a seed culture. About 20L of a fresh preparation of the same nutrient culture medium as used in the above culture were placed in a 30-L fermentor, sterilized by heating, cooled to 27° C., inoculated with 1% (v/v) of the seed culture, and incubated for about 48 hours while stirring under aeration agitation conditions at 27° C. and pH 6.0–8.0. The resultant culture, having about 0.45 unit/ml of α-isomaltosyl-transferring enzyme activity, was centrifuged at 10,000 rpm for 30 min to obtain about 18L of a supernatant having about 0.44 unit/ml of α-isomaltosyl-transferring enzyme activity and a total enzyme activity of about 7,920 units.

Experiment 18

Purification of α-isomaltosyl-transferring Enzyme from *Arthrobacter Ramosus* S1

Eighteen liters of a supernatant obtained in Experiment 17 were salted out with a 80% (w/v) ammonium sulfate at 4° C. for 24 hours, and the resulting sediments were collected by centrifugation at 10,000 rpm for 30 min and dialyzed against 10 mM phosphate buffer (pH 7.0) to obtain about 380 ml of a crude enzyme solution having 6,000 units of α-isomaltosyl-transferring enzyme. The crude enzyme solution was dialyzed against 10 mM phosphate buffer (pH 7.0) containing 1M ammonium sulfate, and the dialyzed solution was centrifuged to remove impurities. The resulting supernatant was fed affinity column chromatography using 500 ml of "SEPHACRYL HR S-200" gel. The enzyme was adsorbed on the gel and then eluted sequentially with a linear gradient decreasing from 1M to 0M of ammonium sulfate and with a linear gradient increasing from 0% (w/v) to 5% (w/v) maltotetraose, resulting in an elution of the enzyme from the gel at a concentration of about 2% (w/v) maltotetraose and collecting fractions with the enzyme activity. The fractions were pooled and dialyzed against 10 mM phosphate buffer (pH 7.0) containing 1M ammonium sulfate, and the dialyzed solution was centrifuged to remove impurities. The supernatant thus obtained was fed to hydrophobic column chromatography using 380 ml of "BUTYL-TOYOPEARL 650M" gel. When eluted with a linear gradient decreasing from 1M to 0M ammonium sulfate, the α-isomaltosyl-transferring enzyme adsorbed on the gel was eluted therefrom at about 0.3M ammonium sulfate, followed by collecting fractions with the enzyme activity for a purified enzyme specimen. The amount of enzyme activity, specific activity, and yield of the α-isomaltosylglucosaccharide-forming enzyme in each purification step are in Table 20.

TABLE 20

| Purification step | Enzyme* activity (unit) | Specific activity of enzyme* (unit/mg protein) | Yield (%) |
|---|---|---|---|
| Culture supernatant | 7,920 | 0.47 | 100 |
| Dialyzed solution after salting out with ammonium sulfate | 6,000 | 3.36 | 75.8 |
| Eluate from affinity column chromatography | 5,270 | 29.9 | 66.5 |
| Eluate from hydrophobic column chromatography | 4,430 | 31.1 | 55.9 |

Note:
The symbol "*" means α-isomaltosyl-transferring enzyme.

The purified α-isomaltosyl-transferring enzyme specimen in this experiment was assayed for purity on gel electrophoresis using a 7.5% (w/v) polyacrylamide gel and detected on the gel as a single protein band, i.e., a high purity enzyme specimen.

Experiment 19

Property of α-isomaltosyl-transferring Enzyme

A purified specimen of α-isomaltosyl-transferring enzyme, obtained by the method in Experiment 18, was subjected to SDS-PAGE using a 7.5% (w/v) of polyacrylamide gel and then determined for molecular weight by comparing with the dynamics of standard molecular markers electrophoresed in parallel, commercialized by Bio-Rad Laboratories Inc., Brussels, Belgium, revealing that the enzyme had a molecular weight of about 116,000±20,000 daltons.

A fresh preparation of the above purified specimen was subjected to isoelectrophoresis using a gel containing 2% (w/v) ampholine commercialized by Amersham Corp., Div. Amersham International, Arlington Heights, Ill., USA, and then measured for pHs of protein bands and gel to determine the isoelectric point of the enzyme, revealing that the enzyme had an isoelectric point of about 4.2±0.5.

Figure 37:
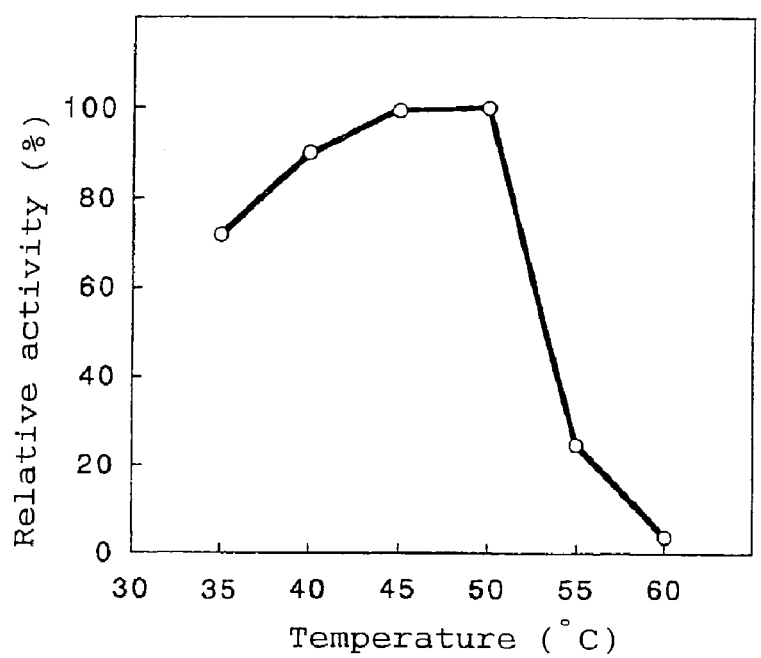
FIG. 37 shows the thermal influence on the enzymatic activity of α-isomaltosyl-transferring enzyme from a microorganism of the species *Arthrobacter ramosus* S1 strain.
Figure 38:
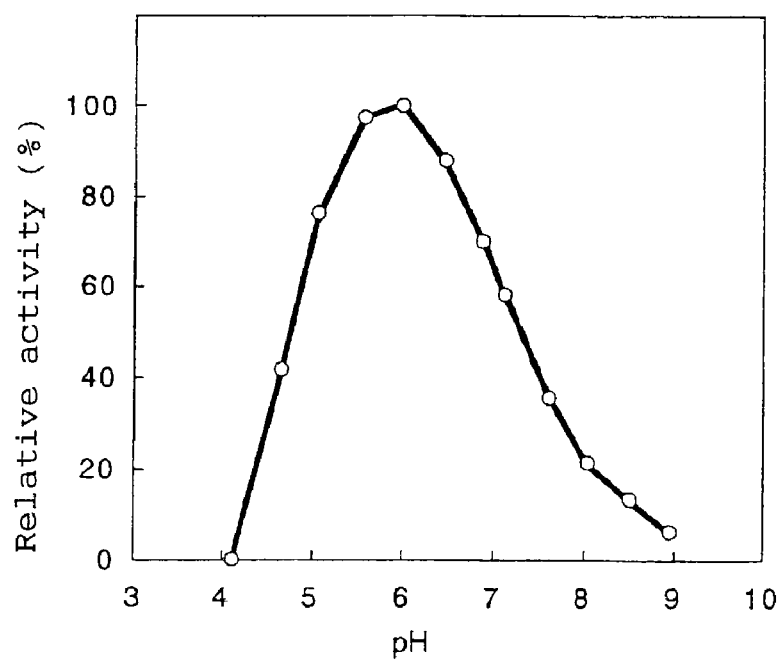
FIG. 38 shows the pH influence on the enzymatic activity of α-isomaltosyl-transferring enzyme from a microorganism of the species *Arthrobacter ramosus* S1 strain.
Figure 39:
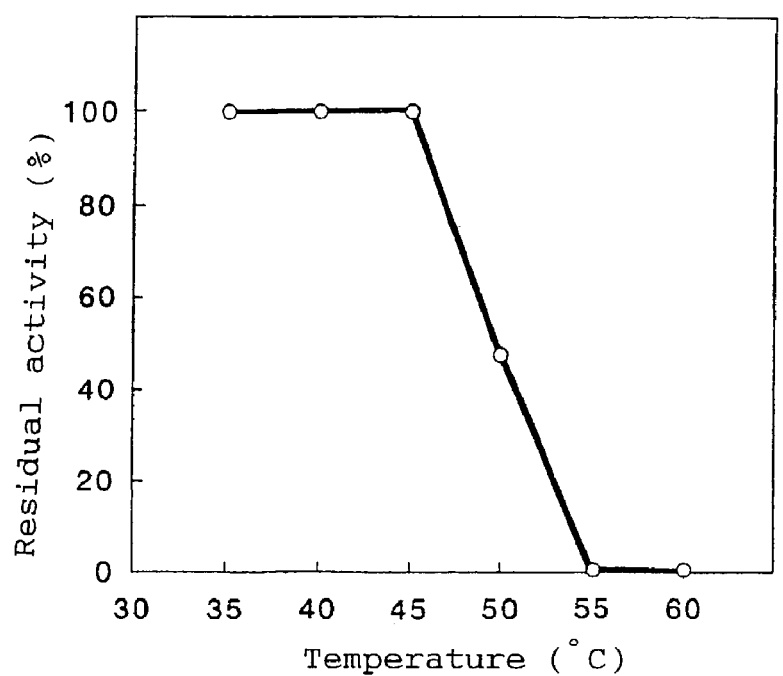
FIG. 39 shows the thermal stability of α-isomaltosyl-transferring enzyme from a microorganism of the species *Arthrobacter ramosus* S1 strain.
Figure 40:
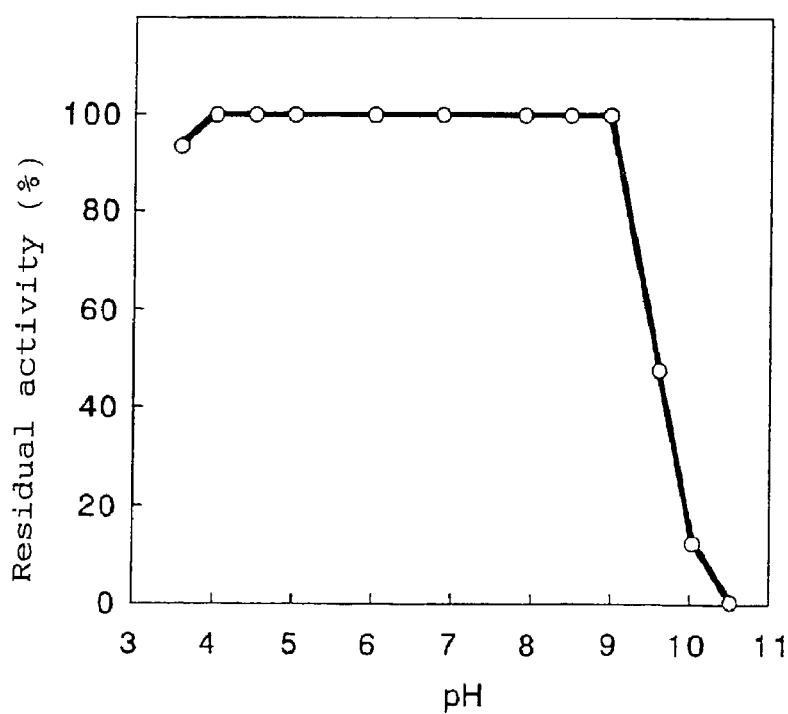
FIG. 40 shows the pH stability of α-isomaltosyl-transferring enzyme from a microorganism of the species *Arthrobacter ramosus* S1 strain.

The influence of temperature and pH on the activity of α-isomaltosyl-transferring enzyme was examined in accordance with the assay for the enzyme activity. These results are in FIG. 37 (influence of temperature) and FIG. 38 (influence of pH). The optimum temperature of the enzyme was about 50° C. when incubated at pH 6.0 for 30 min. The optimum pH of the enzyme was about 6.0 when incubated at 35° C. for 30 min. The thermal stability of the enzyme was determined by incubating the testing enzyme solutions at prescribed temperatures for 60 min in 20 mM acetate buffer (pH 6.0), cooling with water the resulting enzyme solutions, and assaying the remaining enzyme activity of each solution. The pH stability of the enzyme was determined by keeping the testing enzyme solutions in 50 mM buffers having prescribed pHs at 4° C. for 24 hours, adjusting the pH of each solution to 6.0, and assaying the remaining enzyme activity of each solution. These results are respectively in FIG. 39 (thermal stability) and FIG. 40 (pH stability). As a result, the enzyme had thermal stability of up to about 45° C. and had pH stability of about 3.6 to about 9.0.

The influence of metal ions on the activity of α-isomaltosyl-transferring enzyme was examined in the presence of 1 mM of each metal-ion according to the assay for the enzyme activity. The results are in Table 21.

TABLE 21

| Metal ion | Relative activity (%) | Metal ion | Relative activity (%) |
|---|---|---|---|
| None | 100 | $Hg^{2+}$ | 0.1 |
| $Zn^{2+}$ | 78 | $Ba^{2+}$ | 97 |
| $Mg^{2+}$ | 99 | $Sr^{2+}$ | 101 |
| $Ca^{2+}$ | 103 | $Pb^{2+}$ | 85 |
| $Co^{2+}$ | 91 | $Fe^{2+}$ | 105 |
| $Cu^{2+}$ | 2 | $Fe^{3+}$ | 75 |
| $Ni^{2+}$ | 87 | $Mn^{2+}$ | 98 |
| $Al^{3+}$ | 93 | EDTA | 91 |

As evident from the results in Table 21, it was revealed that the enzyme activity was greatly inhibited by $Hg^{2+}$ and was also inhibited by $Cu^{2+}$.

Amino acid analysis of the N-terminal amino acid sequence of the enzyme by "PROTEIN SEQUENCER MODEL 473A", an apparatus of Applied Biosystems, Inc., Foster City, USA, revealed that the enzyme had a partial amino acid sequence of SEQ ID NO:19, i.e., aspartic acid-threonine-leucine-serine -glycine-valine-phenylalanine-histidine-glycine-proline at the N-terminal region.

Experiment 20

Action on Saccharides

It was tested whether saccharides can be used as substrates for the α-isomaltosylglucosaccharide-forming enzyme. For the purpose, a solution of maltose, maltotriose, maltotetraose, maltopentaose, maltohexaose, maltoheptaose, isomaltose, isomaltotriose, panose, isopanose, trehalose, kojibiose, nigerose, neotrehalose, cellobiose, gentibiose, maltitol, maltotriitol, lactose, sucrose, erlose, selaginose, maltosyl glucoside, or isomaltosyl glucoside was prepared.

To each of the above solutions was added two units/g substrate of a purified specimen of α-isomaltosylglucosaccharide-forming enzyme from either *Bacillus globisporus* C9 obtained by the method in Experiment 4-2, *Bacillus globisporus* C11 obtained by the method in Experiment 7-2, *Bacillus globisporus* N75 obtained by the method in Experiment 11-2, or *Arthrobacter globiformis* A19 obtained by the method in Experiment 15-2, and the resulting each solution was adjusted to give a substrate concentration of 2% (w/v) and incubated at 30° C. and pH 6.0, except for using pH 8.4 for the enzyme from *Arthrobacter globiformis* A19, for 24 hours. The enzyme solutions before and after the enzymatic reactions were respectively analyzed on TLC disclosed in Experiment 1 to confirm whether the enzymes acted on these substrates. The results are in Table 22.

TABLE 22

| | Enzymatic action | | | |
|---|---|---|---|---|
| Substrate | Enzyme of Strain C9 | Enzyme of Strain C11 | Enzyme of Strain N75 | Enzyme of Strain A19 |
| Maltose | + | + | + | + |
| Maltotriose | ++ | ++ | ++ | ++ |
| Maltotetraose | +++ | +++ | +++ | +++ |
| Maltopentaose | +++ | +++ | +++ | +++ |
| Maltohexaose | +++ | +++ | +++ | +++ |
| Maltoheptaose | +++ | +++ | +++ | +++ |
| Isomaltose | − | − | − | − |
| Isomaltotriose | − | − | − | − |
| Panose | − | − | − | − |
| Isopanose | ++ | ++ | ++ | ++ |
| Trehalose | − | − | − | − |
| Kojibiose | + | + | + | + |
| Nigerose | + | + | + | + |
| Neotrehalose | + | + | + | + |
| Cellobiose | − | − | − | − |
| Gentiobiose | − | − | − | − |
| Maltitol | − | − | − | − |
| Maltotriitol | + | + | + | + |
| Lactose | − | − | − | − |
| Sucrose | − | − | − | − |
| Erlose | + | + | + | + |
| Selaginose | − | − | − | − |
| Maltosyl glucoside | ++ | ++ | ++ | ++ |
| Isomaltosyl glucoside | − | − | − | − |

Note:
Before and after the enzymatic reaction, the symbols "−", "+", "++", and "+++" mean that it showed no change, it showed a slight reduction of the color spot of the substrate and the formation of other reaction product, it showed a high reduction of the color spot of the substrate and the formation of other reaction product, and it showed a substantial disappearance of the substrate spot and the formation of other reaction product, respectively.

As evident from the Table 22, it was revealed that the α-isomaltosylglucosaccharide-forming enzyme of the present invention well acted on saccharides having a glucose polymerization degree of at least three and having a maltose structure at their non-reducing ends, among the saccharides tested. It was also found that the enzyme slightly acted on saccharides, having a glucose polymerization degree of two, such as maltose, kojibiose, nigerose, neotrehalose, maltotriitol, and erlose.

Experiment 21

Reaction product from Maltooliqosaccharide

Experiment 21-1

Preparation of Reaction Product

To an aqueous solution containing one percent (w/v) of maltose, maltotriose, maltotetraose, or maltopentaose as a substrate was added a purified specimen of α-isomaltosylglucosaccharide-forming enzyme obtained by the method in Experiment 7-2 in an amount of two units/g solid for the aqueous solutions of maltose and maltotriose, 0.2 unit/g solid for maltotetraose, and 0.1 unit/g solid for maltopentaose, followed by incubation at 35° C. and pH 6.0 for eight hours. After a 10-min incubation at 100° C., the enzymatic reaction was suspended. The resulting reaction solutions were respectively measured for saccharide composition on HPLC using "YMC PACK ODS-AQ303", a column commercialized by YMC Co., Ltd., Tokyo, Japan, at a column temperature of 40° C. and a flow rate of 0.5 ml/min of water, and using as a detector "RI-8012", a differential refractometer commercialized by Tosoh Corporation, Tokyo, Japan. The results are in Table 23.

TABLE 23

| | Substrate | | | |
|---|---|---|---|---|
| Saccharide as reaction product | Maltose | Maltotriose | Maltotetraose | Maltopentaose |
| Glucose | 8.5 | 0.1 | 0.0 | 0.0 |
| Maltose | 78.0 | 17.9 | 0.3 | 0.0 |
| Maltotriose | 0.8 | 45.3 | 22.7 | 1.9 |
| Maltotetraose | 0.0 | 1.8 | 35.1 | 19.2 |
| Maltopentaose | 0.0 | 0.0 | 3.5 | 34.4 |
| Maltohexaose | 0.0 | 0.0 | 0.0 | 4.6 |
| Isomaltose | 0.5 | 0.0 | 0.0 | 0.0 |
| Glucosylmaltose | 8.2 | 1.2 | 0.0 | 0.0 |
| Glucosylmaltotriose | 2.4 | 31.5 | 6.8 | 0.0 |
| X | 0.0 | 2.1 | 30.0 | 11.4 |
| Y | 0.0 | 0.0 | 1.4 | 26.8 |
| Z | 0.0 | 0.0 | 0.0 | 1.7 |
| Others | 0.6 | 0.1 | 0.2 | 0.0 |

Note:
In the table, glucosylmaltose means α-isomaltosylglucose alias $6^2$-O-α-glucosylmaltose or panose; glucosylmaltotriose means α-isomaltosylglucose alias $6^3$-O-α-glucosylmaltotriose; X means the α-isomaltosylmaltotriose in Experiment 11-2, alias $6^4$-O-α-glucomaltotetraose; Y means the α-isomaltosylmaltotetraose in Experiment 11-2, alias $6^5$-O-α-glucosylmaltopentaose; and Z means an unidentified saccharide.

As evident from the results in Table 23, it was revealed that, after the action of the enzyme of the present invention, glucose and α-isomaltosylglucose alias $6^2$-O-α-glucosylmaltose or panose were mainly formed from maltose as a substrate; and maltose and α-isomaltosylglucose alias $6^3$-O-α-glucosylmaltotriose were mainly formed along with small amounts of glucose, maltotetraose, α-isomaltosylglucose alias $6^2$-O-α-glucosylmaltose or panose, and the product X. Also, it was revealed that maltotriose and the product X were mainly formed from maltotetraose as a substrate along with small amounts of maltose, maltopentaose, α-isomaltosylglucose alias $6^3$-O-α-glucosylmaltotriose; and the product Y; and that maltotetraose and the product Y were mainly formed from maltopentaose as a substrate along with small amounts of maltotriose, maltohexaose, and the products X and Z.

The product X as a main product from maltotetraose as a substrate and the product Y as a main product from maltopentaose as a substrate were respectively isolated and purified as follows: The products X and Y were respectively purified on HPLC using "YMC PACK ODS-A R355-15S-15 12A", a separatory HPLC column commercialized by YMC Co., Ltd., Tokyo, Japan, to isolate a specimen of the product X having a purity of at least 99.9% from the reaction product from maltotetraose in a yield of about 8.3%, d.s.b., and a specimen of the product Y having a purity of at least 99.9% from the reaction product from maltotetraose in a yield of about 11.5%, d.s.b.

Experiment 21-2

Structural Analysis on Reaction Product

Figure 41:
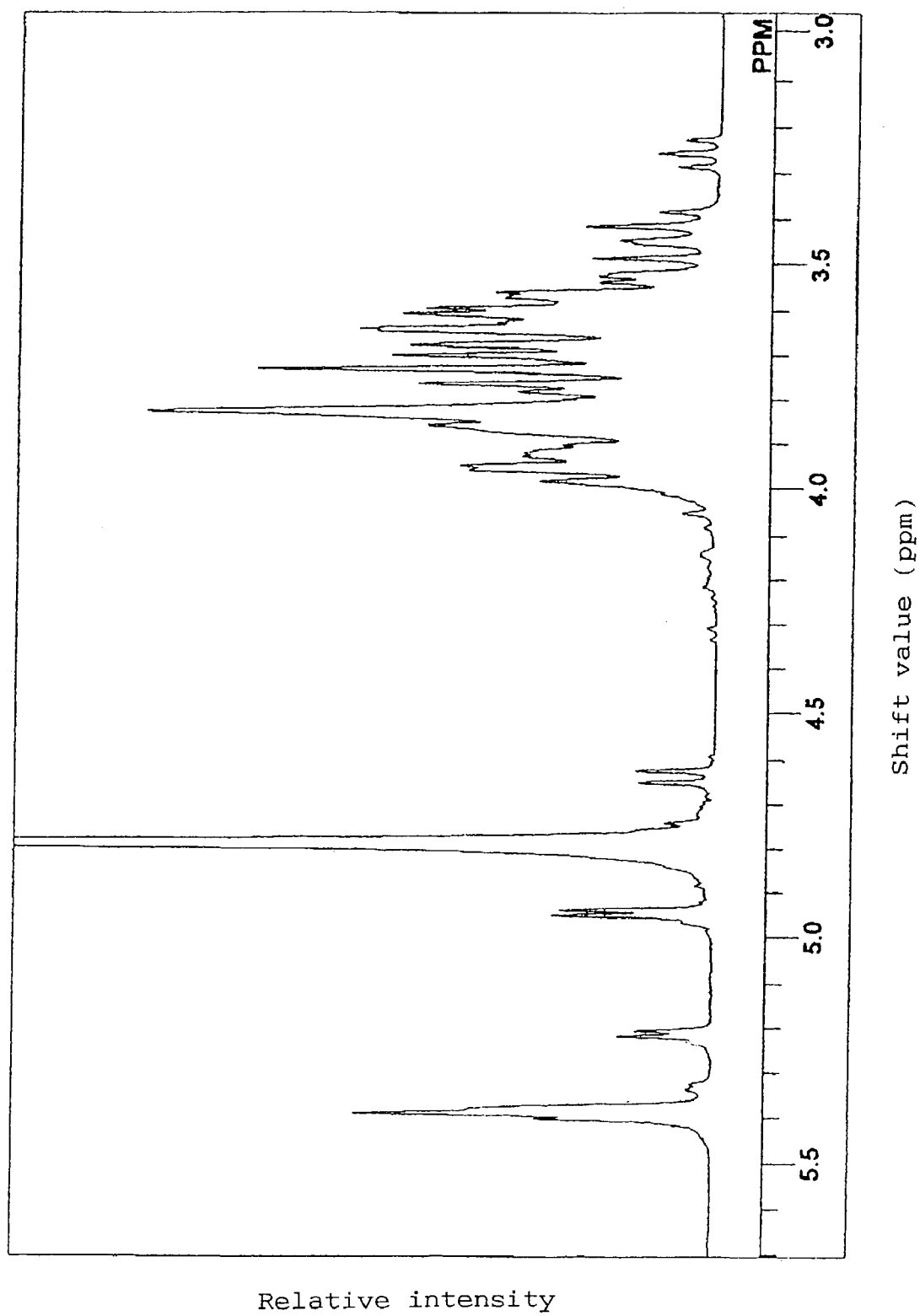
FIG. 41 is a nuclear resonance spectrum ($^1$H-NMR) of α-isomaltosylmaltotriose, obtained by the enzymatic reaction using α-isomaltosylglucosaccharide-forming enzyme of the present invention.
Figure 42:
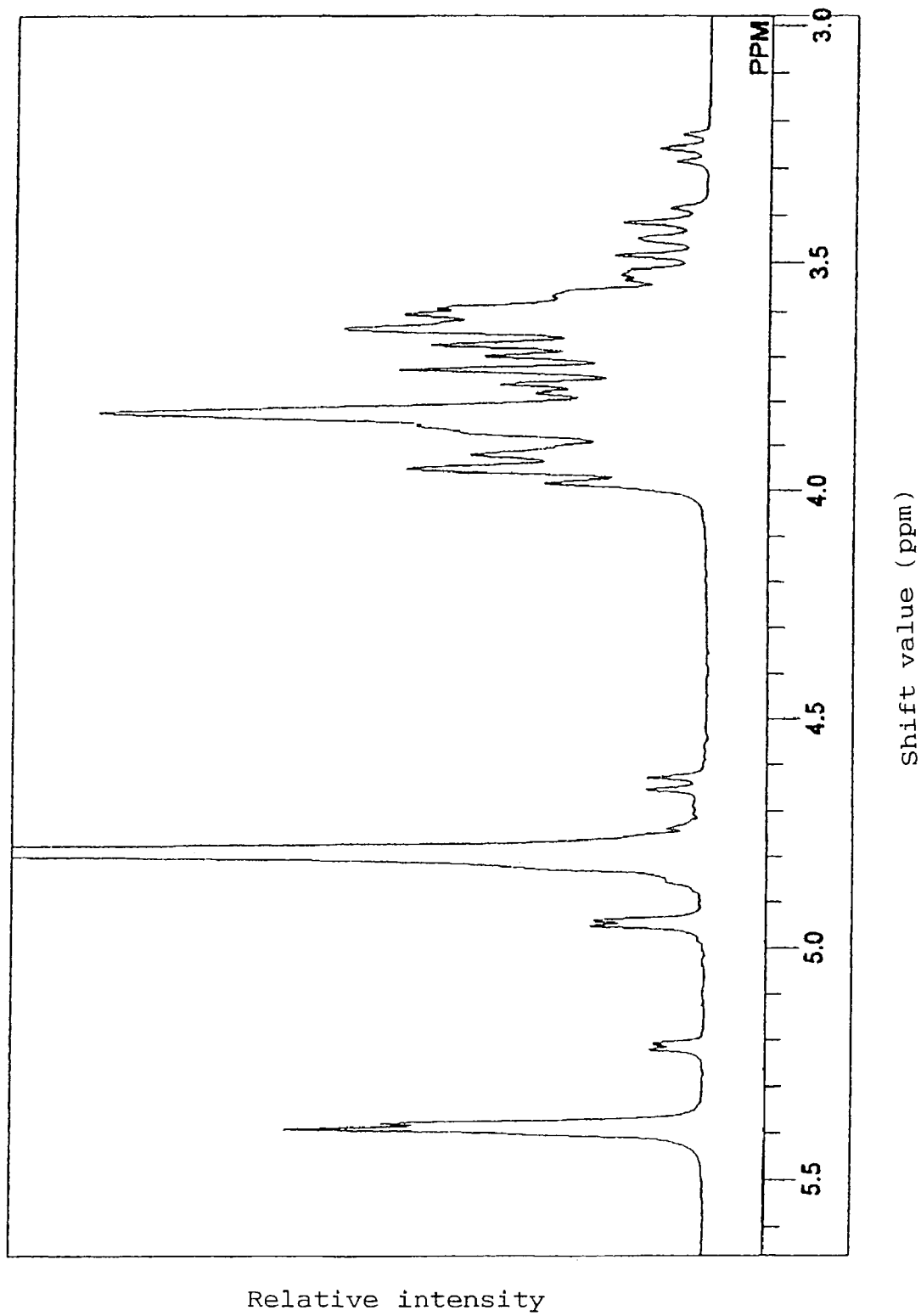
FIG. 42 is a nuclear resonance spectrum ($^1$H-NMR) of α-isomaltosylmaltotetraose, obtained by the enzymatic reaction using α-isomaltosylglucosaccharide-forming enzyme of the present invention.
Figure 43:
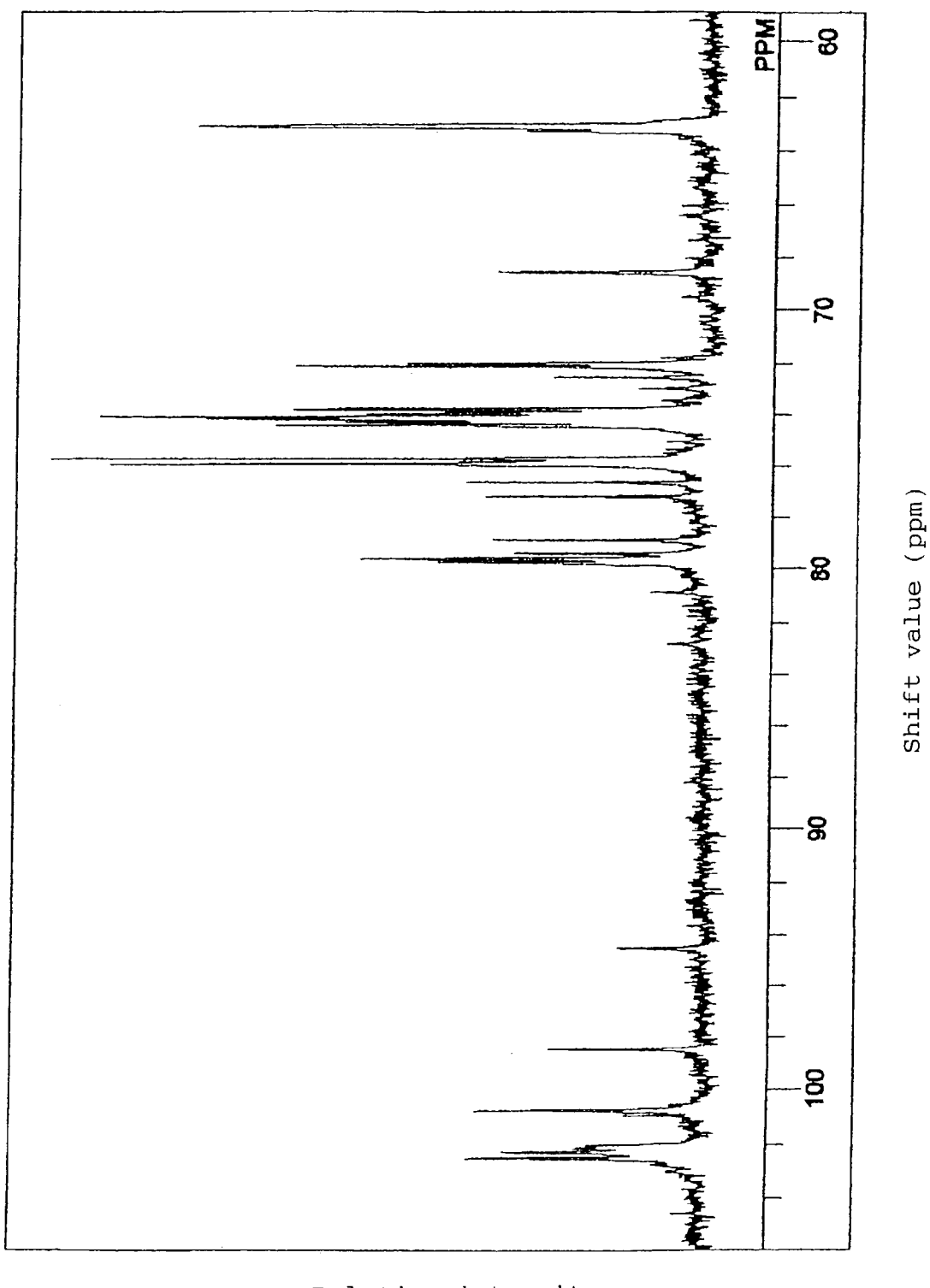
FIG. 43 is a nuclear resonance spectrum ($^{13}$C-NMR) of α-isomaltosylmaltotriose, obtained by the enzymatic reaction using α-isomaltosylglucosaccharide-forming enzyme of the present invention.
Figure 44:
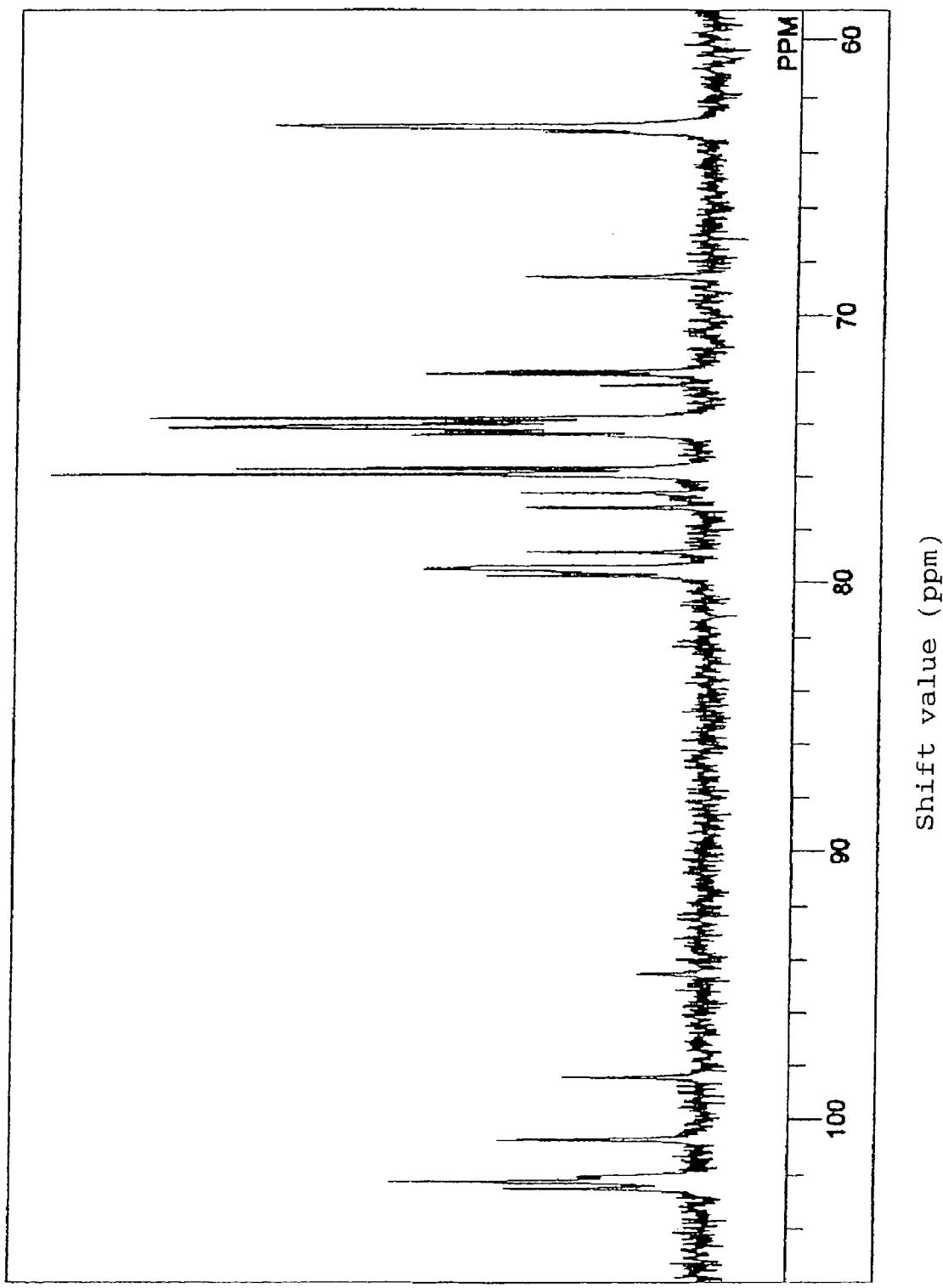
FIG. 44 is a nuclear resonance spectrum ($^{13}$C-NMR) of α-isomaltosylmaltotetraose, obtained by the enzymatic reaction using α-isomaltosylglucosaccharide-forming enzyme of the present invention.

Using the products X and Y obtained by the method in Experiment 21-1, they were subjected to methyl analysis and NMR analysis in a usual manner. The results on their methyl analyses are in Table 24. For the results on their NMR analyses, FIG. 41 is a $^1$H-NMR spectrum for the product X and FIG. 42 is for the product Y. The $^{13}$C-NMR spectra for the products X and Y are respectively FIGS. 43 and 44. The assignment of the products X and Y are tabulated in Table 25.

TABLE 24

| Analyzed methyl compound | Ratio | |
|---|---|---|
| | Product X | Product Y |
| 2,3,4-trimethyl compound | 1.00 | 1.00 |
| 2,3,6-trimethyl compound | 3.05 | 3.98 |
| 2,3,4,6-tetramethyl compound | 0.82 | 0.85 |

Based on these results, the product X formed from maltotetraose via the action of the α-isomaltosylglucosaccharide-forming enzyme of the present invention was revealed as a pentasaccharide, in which a glucose residue binds via the α-linkage to OH-6 of glucose at the non-reducing end of maltotetraose, i.e., α-isomaltosylmaltotriose alias $6^4$-O-α-glucosylmaltotetraose, represented by Formula 1.

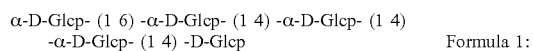

Formula 1:

The product Y formed from maltopentaose was revealed as a hexasaccharide, in which a glucosyl residue binds via the α-linkage to OH-6 of glucose at the non-reducing end of maltopentaose, i.e., α-isomaltosylmaltotetraose alias $6^5$-O-α-glucosylmaltopentaose, represented by Formula 2.

TABLE 25

| Glucose number | Carbon number | Chemical shift on NMR (ppm) | |
|---|---|---|---|
| | | Product X | Product Y |
| a | 1a | 100.8 | 100.8 |
| | 2a | 74.2 | 74.2 |
| | 3a | 75.8 | 75.7 |
| | 4a | 72.2 | 72.2 |
| | 5a | 74.5 | 74.5 |
| | 6a | 63.2 | 63.1 |
| b | 1b | 102.6 | 102.6 |
| | 2b | 74.2 | 74.2 |
| | 3b | 75.8 | 75.7 |
| | 4b | 72.1 | 72.1 |
| | 5b | 74.0 | 74.0 |
| | 6b | 68.6 | 68.6 |
| c | 1c | 102.3 | 102.3 |
| | 2c | 74.2 | 74.2 |
| | 3c | 76.0 | 76.0 |
| | 4c | 79.6 | 79.5 |
| | 5c | 73.9 | 73.9 |
| | 6c | 63.2 | 63.1 |
| d | 1d | 102.2 | 102.3 |
| | 2d | 74.0 (α), 74.4 (β) | 74.2 |
| | 3d | 76.0 | 76.0 |
| | 4d | 79.8 | 79.5 |
| | 5d | 73.9 | 73.9 |
| | 6d | 63.2 | 63.1 |
| e | 1e | 94.6 (α), 98.5 (β) | 102.1 |
| | 2e | 74.2 (α), 76.7 (β) | 74.0 (α), 74.4 (β) |
| | 3e | 75.9 (α), 78.9 (β) | 76.0 |
| | 4e | 79.6 (α), 79.4 (β) | 79.8 |
| | 5e | 72.6 (α), 77.2 (β) | 73.9 |
| | 6e | 63.4 (α), 63.4 (β) | 63.1 |
| f | 1f | | 94.6 (α), 98.5 (β) |
| | 2f | | 74.2 (α), 76.7 (β) |
| | 3f | | 76.0 (α), 78.9 (β) |
| | 4f | | 79.6 (α), 79.5 (β) |
| | 5f | | 72.6 (α), 77.2 (β) |
| | 6f | | 63.3 (α), 63.3 (β) |

Based on these results, it was concluded that the α-isomaltosylglucosaccharide-forming enzyme of the present invention acts on maltooligosaccharides as shown below:

(1) The enzyme acts on as a substrate maltooligosaccharides having a glucose polymerization degree of at least two linked via the α-1,4 linkage, and catalyzes the intermolecular 6-glucosyl-transferring reaction in such a manner of transferring a glucosyl residue at the non-reducing end of a maltooligosaccharide molecule to C-6 of the non-reducing end of other maltooligosaccharide molecule to form both an α-isomaltosylglucosaccharide alias 6-O-α-glucosylmaltooligosaccharide, having a 6-O-α-glucosyl residue and a higher glucose polymerization degree by one as compared with the intact substrate, and a maltooligosaccharide with a reduced glucose polymerization by one as compared with the intact substrate; and (2) The enzyme slightly catalyzes the 4-glucosyl-transferring reaction and forms both a maltooligosaccharide, having an increased glucose polymerization by one as compared with the intact substrate, and a maltooligosaccharide having a reduced glucose polymerization degree by one as compared with the intact substrate.

Experiment 22

Test on Reducing-Power Formation

The following test was carried out to study whether the α-isomaltosylglucosaccharide-formation enzyme of the present invention had the reducing power. To a 1% (w/v) aqueous solution of maltotetraose as a substrate was added 0.25 unit/g substrate, d.s.b., of either of purified specimens of α-isomaltosylglucosaccharide-forming enzyme from *Bacillus globisporus* C9 obtained by the method in Experiment 4-2, *Bacillus globisporus* C11 obtained by the method in Experiment 7-2, *Bacillus globisporus* N75 obtained by the method in Experiment 11-2, or Arthrobacter globiforrnis A19 obtained by the method in Experiment 15-2, and incubated at 35° C. and pH 6.0, except that pH 8.4 was used for the enzyme from *Arthrobacter globiformis* A19. During enzymatic reaction, a portion of each reaction solution was sampled at prescribed time intervals and measured for reducing power after keeping the sampled solutions at 100° C. for 10 min to suspend the enzymatic reaction. Before and after the enzymatic reaction, the reducing saccharide content and the total sugar content were respectively quantified by the Somogyi-Nelson's method and the anthrone-sulfuric acid reaction method.

The percentage of forming reducing power was calculated by the following equation:

Equation:

$$\text{Percentage of forming reducing power (\%)} = \left(\frac{AR}{AT} - \frac{BR}{BT}\right) \times 100$$

AR: Reducing sugar content after enzymatic reaction.
AT: Total sugar content after enzymatic reaction.
BR: Reducing sugar content before enzymatic reaction.
BT: Total sugar content before enzymatic reaction.

The results are in Table 26.

TABLE 26

| Reaction time (hour) | Percentage of forming reducing power (%) | | | |
| --- | --- | --- | --- | --- |
| | Enzyme of Strain C9 | Enzyme of Strain C11 | Enzyme of Strain N75 | Enzyme of Strain A19 |
| 0 | 0.0 | 0.0 | 0.0 | 0.0 |
| 1 | 0.0 | 0.1 | 0.1 | 0.0 |
| 2 | 0.1 | 0.0 | 0.0 | 0.1 |
| 4 | 0.1 | 0.1 | 0.0 | 0.0 |
| 8 | 0.0 | 0.0 | 0.1 | 0.1 |

As evident from the results in Table 26, it was revealed that the α-isomaltosylglucosaccharide-forming enzyme of the present invention did not substantially increase the reducing power of the reaction product when acted on maltotetraose as a substrate; the enzyme did not have hydrolyzing activity or had only an undetectable level of such activity.

Experiment 23

Test on Dextran Formation

To study whether the α-isomaltosylglucosaccharide-formation enzyme of the present invention has the ability to form dextran, it was tested in accordance with the method in *Bioscience Biotechnology and Biochemistry*, Vol. 56, pp. 169–173. . . (1992). To a 1% (w/v) aqueous solution of maltotetraose as a substrate was added 0.25 unit/g substrate, d.s.b., of either of purified specimens of α-isomaltosylglucosaccharide-forming enzyme from *Bacillus globisporus* C9 obtained by the method in Experiment 4-2, *Bacillus globisporus* C11 obtained by the method in Experiment 7-2, *Bacillus globisporus* N75 obtained by the method in Experiment 11-2, or *Arthrobacter globiformis* A19 obtained by the method in Experiment 15-2, and incubated at 35° C. and pH 6.0, except that pH 8.4 was used for the enzyme from *Arthrobacter globiformis* A19, for four or eight hours. After completion of the enzymatic reaction, the reaction was suspended by heating at 100° C. for 15 min. Fifty microliters of each of the reaction mixtures were placed in a centrifugation tube and then admixed and sufficiently stirred with 3-fold volumes of ethanol, followed by standing at 4° C. for 30 mm. Thereafter, each mixture solution was centrifuged at 15,000 rpm for five minutes and, after removing supernatant, the resulting sediment was admixed with one milliliter of 75% (w/w) ethanol solution and stirred for washing. Each resulting solution was centrifuged to remove supernatant, dried in vacuo, and then admixed and sufficiently stirred with one milliliter of deionized water. The total sugar content, in terms of glucose, of each resulting solution was quantified by the phenol-sulfuric acid method. As a control, the total sugar content was determined similarly as in the above except for using either of purified specimens of α-isomaltosylglucosaccharide-forming enzyme from *Bacillus globisporus* C9, *Bacillus globisporus* C11, *Bacillus globisporus* N75, and *Arthrobacter globiforinis* A19, which had been inactivated at 100° C. for 10 min. . . The content of dextran formed was calculated by the following equation:

Equation:

Content of dextran formed(*mg/ml*)=[(Total sugar content for test sample)]−[(Total sugar content for control sample)]×20

The results are in Table 27.

TABLE 27

| Reaction time (hour) | Content of dextran formed (mg/ml) | | | |
| --- | --- | --- | --- | --- |
| | Enzyme of Strain C9 | Enzyme of Strain C11 | Enzyme of Strain N75 | Enzyme of Strain A19 |
| 4 | 0.0 | 0.0 | 0.0 | 0.0 |
| 8 | 0.0 | 0.0 | 0.0 | 0.0 |

As evident from the results in Table 27, it was revealed that the α-isomaltosylglucosaccharide-forming enzyme of the present invention did not substantially have the action of forming dextran or had only an undetectable level of such activity because it did not form dextran when it acted on maltotetraose.

Experiment 24

Transfer-Acceptor Specificity

Using different saccharides, it was tested whether the saccharides were used as transferring-acceptors for the α-isomaltosylglucosaccharide-forming enzyme of the present invention. A solution of D-glucose, D-xylose, L-xylose, D-galactose, D-fructose, D-mannose, D-arabinose, D-fucose, D-psicose, L-sorbose, L-rhamnose, methyl-α-glucopyranoside, methyl-β-glucopyranoside, N-acetyl-glucosamine, sorbitol, trehalose, isomaltose, isomaltotriose, cellobiose, gentibiose, glycerol, maltitol, lactose, sucrose, α-cyclodextrin, β-cyclodextrin, γ-cyclodextrin, or L-ascorbic acid was prepared.

To each solution with a saccharide concentration of 1.6% was added "PINE-DEX #100", a partial starch hydrolysate, as a saccharide donor, to give a concentration of 4%, and admixed with one unit/g saccharide donor, d.s.b., of either of purified specimens of α-isomaltosylglucosaccharide-forming enzyme from *Bacillus globisporus* C9 obtained by the method in Experiment 4-2, *Bacillus globisporus* C11 obtained by the method in Experiment 7-2, *Bacillus globisporus* N75 obtained by the method in Experiment 11-2, or *Arthrobacter globiformis* A19 obtained by the method in Experiment 15-2, and incubated at 30° C. and pH 6.0, except that pH 8.4 was used for the enzyme from *Arthrobacter globiformis* A19, for 24 hours. The reaction mixtures of the post-enzymatic reactions were analyzed on gas chromatography (abbreviated as "GLC" hereinafter) for monosaccharides and disaccharides as acceptors, and on HPLC for trisaccharides as acceptors to confirm whether these saccharides could be used as their transfer acceptors. In the case of performing GLC, the following apparatuses and conditions are used: GLC apparatus, "GC-16A" commercialized by Shimadzu Corporation, Tokyo, Japan; column, a stainless-steel column, 3 mm in diameter and 2 m in length, packed with 2% "SILICONE OV-17/CHROMOSOLV W", commercialized by GL Sciences Inc., Tokyo, Japan; carrier gas, nitrogen gas at a flow rate of 40 ml/min under temperature conditions of increasing from 160° C. to 320° C. at an increasing temperature rate of 7.5° C./min; and detection, a hydrogen flame ionization detector. In the case of HPLC analysis, the apparatuses and conditions used are: HPLC apparatus, "CCPD" commercialized by Tosoh Corporation, Tokyo, Japan; column, "ODS-AQ-303" commercialized by YMC Co., Ltd., Tokyo, Japan; eluent, water at a flow rate of 0.5 ml/min; and detection, a differential refractometer. The results are in Table 28.

TABLE 28

| Saccharide | Product of transferring reaction | | | |
|---|---|---|---|---|
| | Enzyme of Strain C9 | Enzyme of Strain C11 | Enzyme of Strain N75 | Enzyme of Stain A19 |
| D-Glucose | + | + | + | + |
| D-Xylose | ++ | ++ | ++ | + |
| L-Xylose | ++ | ++ | ++ | + |
| D-Galactose | + | + | + | ± |
| D-Fructose | + | + | + | + |
| D-Mannose | − | − | − | ± |
| D-Arabinose | ± | ± | ± | ± |
| D-Fucose | + | + | + | ± |
| D-Psicose | + | + | + | + |
| L-Sorbose | + | + | + | + |
| L-Rhamnose | − | − | − | − |
| Methyl-α-glucopyranoside | ++ | ++ | ++ | ++ |
| Methyl-β-glucopyranoside | ++ | ++ | ++ | ++ |
| N-Acetyl-glucosamine | + | + | + | − |
| Sorbitol | − | − | − | − |
| Trehalose | ++ | ++ | ++ | ++ |
| Isomaltose | ++ | ++ | ++ | + |

TABLE 28-continued

| Saccharide | Product of transferring reaction | | | |
|---|---|---|---|---|
| | Enzyme of Strain C9 | Enzyme of Strain C11 | Enzyme of Strain N75 | Enzyme of Stain A19 |
| Isomaltotriose | ++ | ++ | ++ | ± |
| Cellobiose | ++ | ++ | ++ | ++ |
| Gentibiose | ++ | ++ | ++ | + |
| Glycerol | + | + | + | + |
| Maltitol | ++ | ++ | ++ | ++ |
| Lactose | ++ | ++ | ++ | ++ |
| Sucrose | ++ | ++ | ++ | ++ |
| α-Cyclodextrin | − | − | − | − |
| β-Cyclodextrin | − | − | − | − |
| γ-Cyclodextrin | − | − | − | − |
| L-Ascorbic acid | + | + | + | + |

Note:
In the table, the symbols "−", "±", "+", and "++" mean that no saccharide-transferred product was detected through transfer reaction to acceptor; a saccharide-transferred productwas detected in an amount less than one percent through transfer reaction to acceptor; a saccharide-transferred product was detected in an amount over one percent but less than ten percent through transfer reaction to acceptor;and a saccharide-transferred product was detected in an amount over ten percent through transfer reaction to acceptor.

As evident from the results in Table 28, it was revealed that the α-isomaltosylglucosaccharide of the present invention utilizes different types of saccharides as transfer acceptors; the α-isomaltosylglucosaccharide-forming enzyme from Stains C9, C11 and N75 advantageously transfer, particularly, to D-/L-xylose, methyl-α-glucopyranoside, methyl-β-glucopyranoside, trehalose, isomaltose, isomaltotriose, cellobiose, gentibiose, maltitol, lactose, and sucrose; then transfer to D-glucose, D-fructose, D-fucose, D-psicose, L-sorbose, N-acetylglucosamine, glycerol, and L-ascorbic acid; and further to D-arabinose. The α-isomaltosylglucosaccharide-forming enzyme from Strain A19 well transfers, particularly, to methyl-α-glucopyranoside, methyl-β-glucopyranoside, trehalose, cellobiose, maltitol, lactose, and sucrose; then transfers to D-glucose, D-/L-xylose, D-fructose, D-psicose, L-sorbose, isomaltose, gentibiose, glycerol, and L-ascorbic acid; and further to D-galactose, D-mannose, D-arabinose, D-fucose, and isomaltotriose.

The properties of the α-isomaltosylglucosaccharide of the present invention described above were compared with those of a previously reported enzyme having 6-glucosyl-transferring action; a dextrin dextranase disclosed in "*Bioscience Biotechnology and Biochemistry*", Vol. 56, pp. 169–173 (1992); and a transglucosidase disclosed in "*Nippon Nogeikagaku Kaishi*", Vol. 37, pp. 668–672 (1963). The results are in Table 29.

TABLE 29

| Property | α-Isomaltosyl-glucosaccharide-forming enzyme of the present invention | | | | Dextrin dextranase Control | Transglucosidase Control |
|---|---|---|---|---|---|---|
| | Strain C9 | Strain C11 | Strain N75 | Strain A19 | | |
| Hydrolysis activity | Negative | Negative | Negative | Negative | Negative | Mainly positive |
| Optimum pH | 6.0–6.5 | 6.0 | 6.0 | 8.4 | 4.0–4.2 | 3.5 |
| Inhibition by EDTA | Positive | Positive | Positive | Positive | Negative | Negative |

As evident from Table 29, the α-isomaltosylglucosaccharide-forming enzyme of the present invention had outstandingly novel physicochemical properties completely different from those of known dextrin dextranase and transglucosidase.

Experiment 25

Formation of Cyclotetrasaccharide

The test on the formation of cyclotetrasaccharide by the α-isomaltosylglucosaccharide-forming enzyme and α-isomaltosyl-transferring enzyme was conducted using saccharides. For the test, prepared a solution of maltose, maltotriose, maltotetraose, maltopentaose, amylose, soluble starch, "PINE-DEX #100" (a partial starch hydrolyzate commercialized by Matsutani Chemical Ind., Tokyo, Japan), or glycogen from oyster commercialized by Wako Pure Chemical Industries Ltd., Tokyo, Japan was prepared.

To each of these solutions with a respective concentration of 0.5%, one unit/g solid of a purified specimen of α-isomaltosylglucosaccharide-forming enzyme from Strain C11 obtained by the method in Experiment 7-2 and 10 units/g solid of a purified specimen of α-isomaltosyl-transferring enzyme from Strain C11 obtained by the method in Experiment 7-3, and the resulting mixture was subjected to an enzymatic reaction at 30° C. and pH 6.0. The enzymatic conditions were the following four systems:

(1) After the α-isomaltosylglucosaccharide-forming enzyme was allowed to act on a saccharide solution for 24 hours, the enzyme was inactivated by heating, and then the α-isomaltosyl-transferring enzyme was allowed to act on the resulting mixture for 24 hours and inactivated by heating;

(2) After the α-isomaltosylglucosaccharide-forming enzyme and the α-isomaltosyl-transferring enzyme were allowed in combination to act on a saccharide solution for 24 hours, then the saccharides were inactivated by heating;

(3) After only the α-isomaltosylglucosaccharide-forming enzyme was allowed to act on a saccharide solution for 24 hours, then the enzyme was inactivated by heating; and (4) After only the α-isomaltosyl-transferring enzyme was allowed to act on a saccharide solution for 24 hours, then the enzyme was inactivated by heating.

To determine the formation level of cyclotetrasaccharide in each reaction mixture after the heating, the reaction mixture was treated with a similar α-glucosidase and glucoamylase as in Experiment 1 to hydrolyze the remaining reducing oligosaccharides, followed by the quantitation of cyclotetrasaccharide on HPLC. The results are in Table 30.

TABLE 30

| Substrate | Formation yield of cyclotetrasaccharide (%) | | | |
| --- | --- | --- | --- | --- |
|  | A | B | C | D |
| Maltose | 4.0 | 4.2 | 0.0 | 0.0 |
| Maltotriose | 10.2 | 12.4 | 0.0 | 0.0 |
| Maltotetraose | 11.3 | 21.5 | 0.0 | 0.0 |
| Maltopentaose | 10.5 | 37.8 | 0.0 | 0.0 |
| Amylose | 3.5 | 31.6 | 0.0 | 0.0 |

TABLE 30-continued

| Substrate | Formation yield of cyclotetrasaccharide (%) | | | |
| --- | --- | --- | --- | --- |
|  | A | B | C | D |
| Soluble starch | 5.1 | 38.2 | 0.0 | 0.0 |
| Partial starch hydrolyzate | 6.8 | 63.7 | 0.0 | 0.0 |
| Glycogen | 10.2 | 86.9 | 0.0 | 0.0 |

Note:
The symbols "A", "B", "C" and "D" mean that α-isomaltosylglucosaccharide-forming enzyme was first allowed to act on a substrate and then α-isomaltosyl-transferring enzyme was allowed actedon the substrate, the α-isomaltosylglucosaccharide-forming enzyme and α-isomaltosyl-transferring enzyme were allowed to coact on a substrate, only α-isomaltosylglucosaccharide-forming enzyme was allowed to act on a substrate,and only α-isomaltosyl-transferring enzyme was allowed to act on a substrate.

As evident from the results in Table 30, no cyclotetrasaccharide was formed from any of the saccharides tested by the action of only α-isomaltosylglucosaccharide-forming enzyme or α-isomaltosyl-transferring enzyme, but cyclotetrasaccharide was formed by the coaction of these enzymes. It was revealed that the formation level was relatively low as below about 11% when α-isomaltosyl-transferring enzyme was allowed to act on the saccharides after the action of α-isomaltosylglucosaccharide-forming enzyme, while the level was increased by simultaneously allowing the enzymes to act on every saccharide tested, particularly, increased to about 87% and about 64% when allowed to act on glycogen and partial starch hydrolyzate, respectively.

Based on the reaction properties of α-isomaltosylglucosaccharide-forming enzyme and α-isomaltosyl-transferring enzyme, the formation mechanism of cyclotetrasaccharide by the coaction of these enzymes is estimated as follows:

(1) The α-isomaltosylglucosaccharide-forming enzyme of the present invention acts on a glucose residue at the non-reducing end of an α-1,4 glucan chain of glycogen and partial starch hydrolyzates, etc., and intermolecularly transfers the glucose residue to OH-6 of a glucose residue at the non-reducing end of another α-1,4 glucan chain of glycogen to form an α-1,4 glucan chain having an α-isomaltosyl residue at the non-reducing end;

(2) α-Isomaltosyl-transferring enzyme acts on the α-1,4 glucan chain having an α-isomaltosyl residue at the non-reducing end and intermolecularly transfers the isomaltosyl residue to C-3 of glucose residue at the non-reducing end of other α-1,4 glucan chain having isomaltosyl residue at the non-reducing end to form an α-1,4 glucan chain having an isomaltosyl-1,3-isomaltosyl residue at the non-reducing end;

(3) Then, α-isomaltosyl-transferring enzyme acts on the α-1,4 glucan chain having an isomaltosyl-1,3-isomaltosyl residue at the non-reducing end and releases the isomaltosyl-1,3-isomaltosyl residue from the α-1,4 glucan chain via the intramolecular transferring reaction to cyclize the released isomaltosyl-1,3-isomaltosyl residue into cyclotetrasaccharide;

(4) From the released α-1,4 glucan chain, cyclotetrasaccharide is formed through the sequential steps (1) to (3). Thus, it is estimated that the coaction of α-isomaltosylglucosaccharide-forming enzyme and α-isomaltosyl-transferring enzyme in such a cyclic manner as indicated above increases the formation of cyclotetrasaccharide.

Experiment 26

Influence of Liquefaction Degree of Starch

A 15% corn starch suspension was prepared, admixed with 0.1% calcium carbonate, adjusted to pH 6.0, and then mixed with 0.2–2.0% per gram starch of "TERMANYL 60 L", an α-amylase specimen commercialized by Novo Indutri A/S, Copenhagen, Denmark, followed by the enzymatic reaction at 95° C. for 10 min. Thereafter, the reaction mixture was autoclaved at 120° C. for 20 mm, promptly cooled to about 35° C. to obtain a liquefied starch with a DE (dextrose equivalent) of 3.2–20.5. To the liquefied starch were added two units/g solid of a purified specimen of α-isomaltosylglucosaccharide-forming enzyme from Strain C11 obtained by the method in Experiment 7-2, and 20 units/g solid of a purified specimen of α-isomaltosyl-transferring enzyme from Strain C11 obtained by the method in Experiment 7-3, followed by the incubation at 35° C. for 24 hours. After completion of the reaction, the reaction mixture was heated at 100° C. for 15 min to inactivate the remaining enzymes. Then, the reaction mixture thus obtained was treated with α-glucosidase and glucoamylase similarly as in Experiment 1 to hydrolyze the remaining reducing oligosaccharides, followed by quantifying the formed cyclotetrasaccharide on HPLIC. The results are in Table 31.

TABLE 31

| Amount of α-amylase per starch (%) | DE | Yield of cyclotetrasaccharide (%) |
| --- | --- | --- |
| 0.2 | 3.2 | 54.5 |
| 0.4 | 4.8 | 50.5 |
| 0.6 | 7.8 | 44.1 |
| 1.0 | 12.5 | 39.8 |
| 1.5 | 17.3 | 34.4 |
| 2.0 | 20.5 | 30.8 |

As evident from the results in Table 31, it was revealed that the formation of cyclotetrasaccharide by the coaction of α-isomaltosylglucosaccharide-forming enzyme and α-isomaltosyl-transferring enzyme is influenced by the liquefaction degree of starch, i.e., the lower the liquefaction degree or the lower the DE the more the yield of cyclotetrasaccharide from starch becomes. On the contrary, the higher the liquefaction degree or the high the DE the lower the yield of cyclotetrasaccharide from starch becomes. It was revealed that a suitable liquefaction degree is a DE of about 20 or lower, preferably, DE of about 12 or lower, more preferably, DE of about 5 or lower.

Experiment 27

Influence of Concentration of Partial Starch Hydrolyzate

Aqueous solutions of "PINE-DEX #100", a partial starch hydrolyzate with a DE of about 2 to about 5, having a final concentration of 0.5–40%, were prepared and respectively admixed with one unit/g solid of a purified specimen of α-isomaltosylglucosaccharide-forming enzyme from Strain C11 obtained by the method in Experiment 7-2 and 10 units/g solid of a purified specimen of α-isomaltosyl-transferring enzyme from Strain C11 obtained by the method in Experiment 7-3, followed by the coaction of these enzymes at 30° C. and pH 6.0 for 48 hours. After completion of the reaction, the reaction mixture was heated at 100° C. for 15 min to inactivate the remaining enzymes, and then treated with α-glucosidase and glucoamylase similarly as in Experiment 1 to hydrolyze the remaining reducing oligosaccharides, followed by quantifying the formed cyclotetrasaccharide on HPLC. The results are in Table 32.

TABLE 32

| Concentration of PINE-DEX (%) | Formation yield of cyclotetrasaccharide (%) |
| --- | --- |
| 0.5 | 63.6 |
| 2.5 | 62.0 |
| 5 | 60.4 |
| 10 | 57.3 |
| 15 | 54.6 |
| 20 | 51.3 |
| 30 | 45.9 |
| 40 | 35.9 |

As is evident from the results in Table 32, the formation yield of cyclotetrasaccharide was about 64% at a low concentration of 0.5%, while it was about 40% at a high concentration of 40%. The fact indicated that the formation yield of cyclotetrasaccharide increased depending on the concentration of partial starch hydrolyzate as a substrate. The result revealed that the formation yield of cyclotetrasaccharide increased as the decrease of partial starch hydrolyzate.

Experiment 28

Influence of the Addition of Cyclodextrin Glucanotransferase

A 15% aqueous solution of "PINE-DEX #100", a partial starch hydrolyzate was prepared and admixed with one unit/g solid of a purified specimen of α-isomaltosylglucosaccharide-forming enzyme from Strain C11 obtained by the method in Experiment 7-2, 10 units/g solid of a purified specimen of α-isomaltosyl-transferring enzyme from Strain C11 obtained by the method in Experiment 7-3, and 0–0.5 unit/g solid of cyclodextrin glucanotransferase (CGTase) from a microorganism of the species *Bacillus stearothermophilus*, followed by the coaction of these enzymes at 30° C. and pH 6.0 for 48 hours. After completion of the reaction, the reaction mixture was heated at 100° C. for 15 min to inactivate the remaining enzymes, and then treated with α-glucosidase and glucoamylase similarly as in Experiment 1 to hydrolyze the remaining reducing oligosaccharides, followed by quantifying the formed cyclotetrasaccharide on HPLC. The results are in Table 33.

TABLE 33

| Amount of CGTase added (unit) | Formation yield of cyclotetrasaccharide (%) |
| --- | --- |
| 0 | 54.6 |
| 2.5 | 60.1 |
| 5 | 63.1 |
| 10 | 65.2 |

As evident from the Table 33, it was revealed that the addition of CGTase increased the formation yield of cyclotetrasaccharide.

Experiment 29

Preparation of Cyclotetrasaccharide

About 100L of a 4% (w/v) aqueous solution of corn phytoglycogen, commercialized by Q. P. Corporation, Tokyo, Japan, was prepared, adjusted to pH 6.0 and 30° C., and then admixed with one unit/g solid of a purified specimen of α-isomaltosylglucosaccharide-forming enzyme from Strain C11 obtained by the method in Experiment 7-2, 10 units/g solid of a purified specimen of α-isomaltosyl-transferring enzyme from Strain C11 obtained by the method in Experiment 7-3, followed by the incubation for 48 hours.

After completion of the reaction, the reaction mixture was heated at 100° C. for 10 min to inactivate the remaining enzymes, and a portion of the reaction mixture was sampled and then quantified on HPLC for the formation yield of cyclotetrasaccharide, revealing that it contained about 84% cyclotetrasaccharide, on a saccharide composition basis. The reaction mixture was adjusted to pH 5.0 and 45° C., and then treated with α-glucosidase and glucoamylase similarly as in Experiment 1 to hydrolyze the remaining reducing oligosaccharides, etc. The resulting mixture was adjusted to pH 5.8 by the addition of sodium hydroxide and then incubated at 90° C. for one hour to inactivate the remaining enzymes and filtered to remove insoluble substances. The filtrate was concentrated using a reverse osmosis membrane to give a concentration of about 16%, d.s.b., and the concentrate was in a usual manner decolored, desalted, filtered, and concentrated to obtain about 6.2 kg of a saccharide solution with a solid content of about 3,700 g.

The saccharide solution was fed to a column packed with about 225L of "AMBERLITE CR-1310 (Na-form)", an ion-exchange resin commercialized by Japan Organo Co., Ltd., Tokyo, Japan, and chromatographed at a column temperature of 60° C. and a flow rate of about 45L/h. While the saccharide composition of eluate from the column was monitored by HPLC as described in Experiment 1, fractions of cyclotetrasaccharide with a purity of at least 98% were collected, and in a usual manner desalted, decolored, filtered, and concentrated to obtain about 7.5 kg of a saccharide solution with a solid content of about 2,500 g solids. HPLC measurement for saccharide composition of the saccharide solution revealed that it contained cyclotetrasaccharide with a purity of about 99.5%.

Experiment 30

Crystallization of Cyclotetrasaccharide in Aqueous Solution

Figure 45:
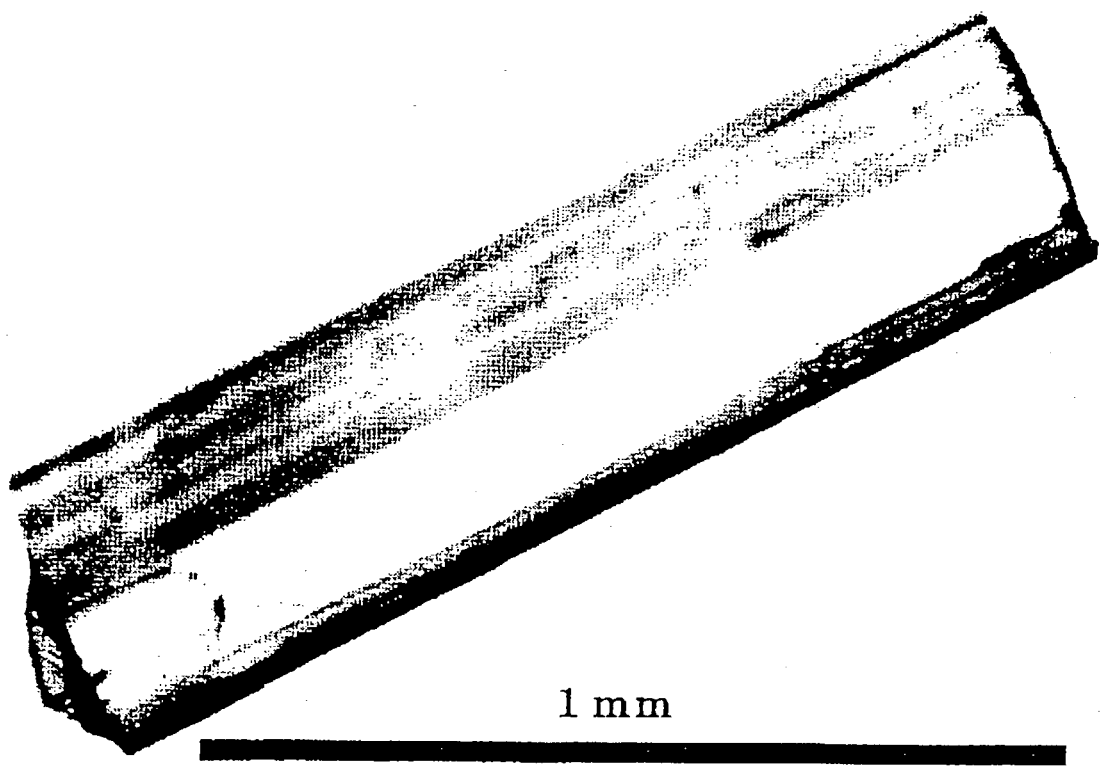
FIG. 45 is a visualized intermediate picture, displayed on a screen, of a microscopic photo for the cyclotetrasaccharide crystal, penta- to hexa-hydrate, of the present invention.

A fraction of cyclotetrasaccharide with a purity of at least 98%, obtained by the method in Experiment 29, was concentrated by evaporation to give a concentration of about 50%, d.s.b. About five kilograms of the concentrate was placed in a cylindrical plastic vessel and then crystallized to obtain a white crystalline powder by lowering the temperature of the concentrate from 65° C. to 20° C. over about 20 hours under gentle rotatory conditions. FIG. 45 is a microscopic photograph of such cyclotetrasaccharide. The above crystallized concentrate was separated by a centrifugal filter to obtain 1,360 g of a crystalline product by wet weight, which was then further dried at 60° C. for three hours to obtain 1,170 g of a crystalline powder of cyclotetrasaccharide. HPLC measurement of the crystalline powder revealed that it contained cyclotetrasaccharide with a quite high purity of at least 99.9%.

Figure 46:
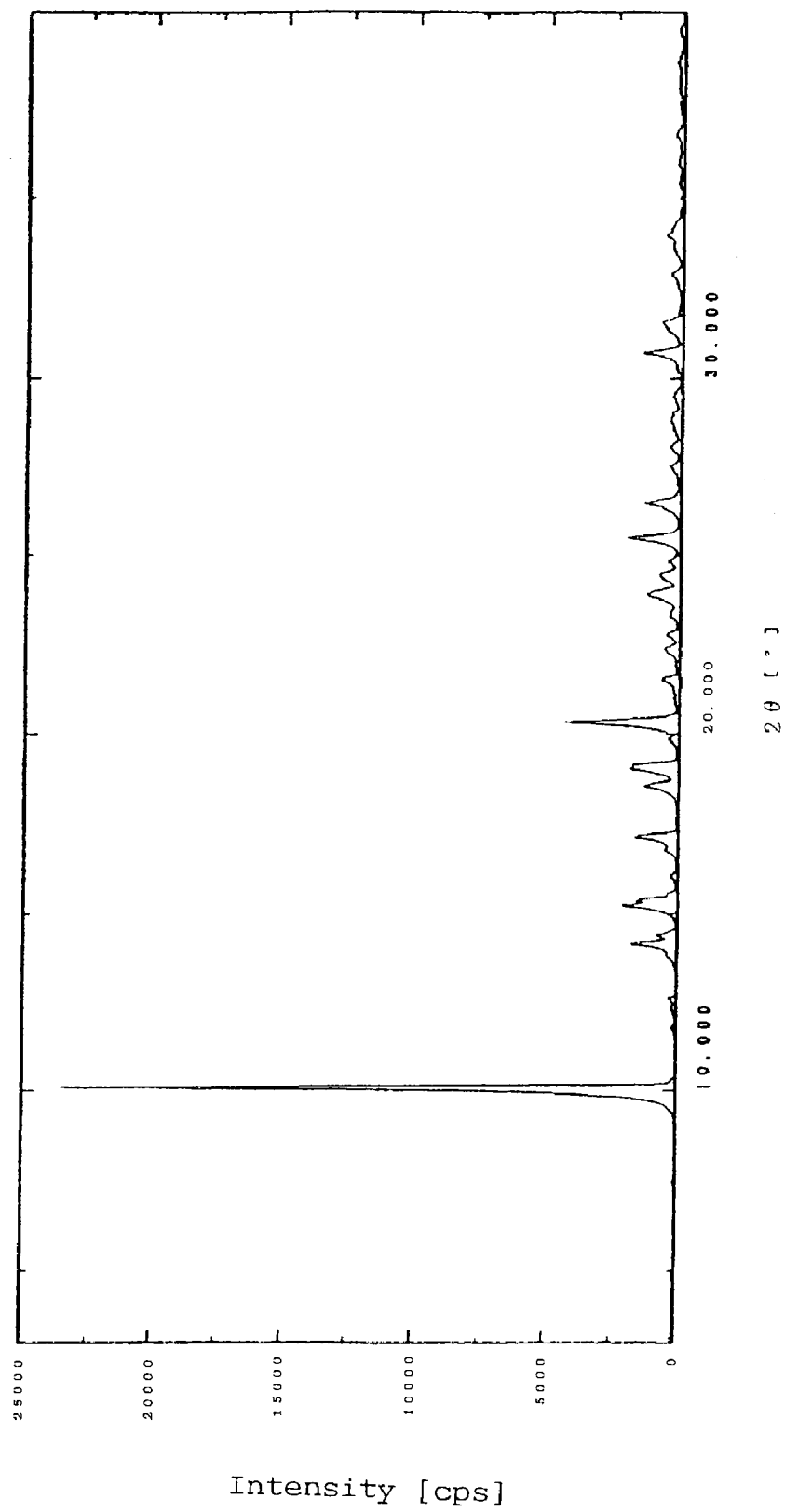
FIG. 46 is an x-ray diffraction spectrum for the cyclotetrasaccharide, penta- to hexa-hydrate, in a crystalline form, of the present invention, when determined on x-ray powder diffraction analysis.

When analyzed on powder x-ray diffraction analysis, the cyclotetrasaccharide in a crystalline powder form had a diffraction spectrum having characteristic main diffraction angles (2θ) of 10.1°, 15.2°, 20.3°, and 25.5° in FIG. 46. The Karl Fischer method of the crystalline powder revealed that it had a moisture content of 13.0%, resulting in a finding that it was a crystal of cyclotetrasaccharide having five or six moles of water per one mole of the crystal.

Figure 47:
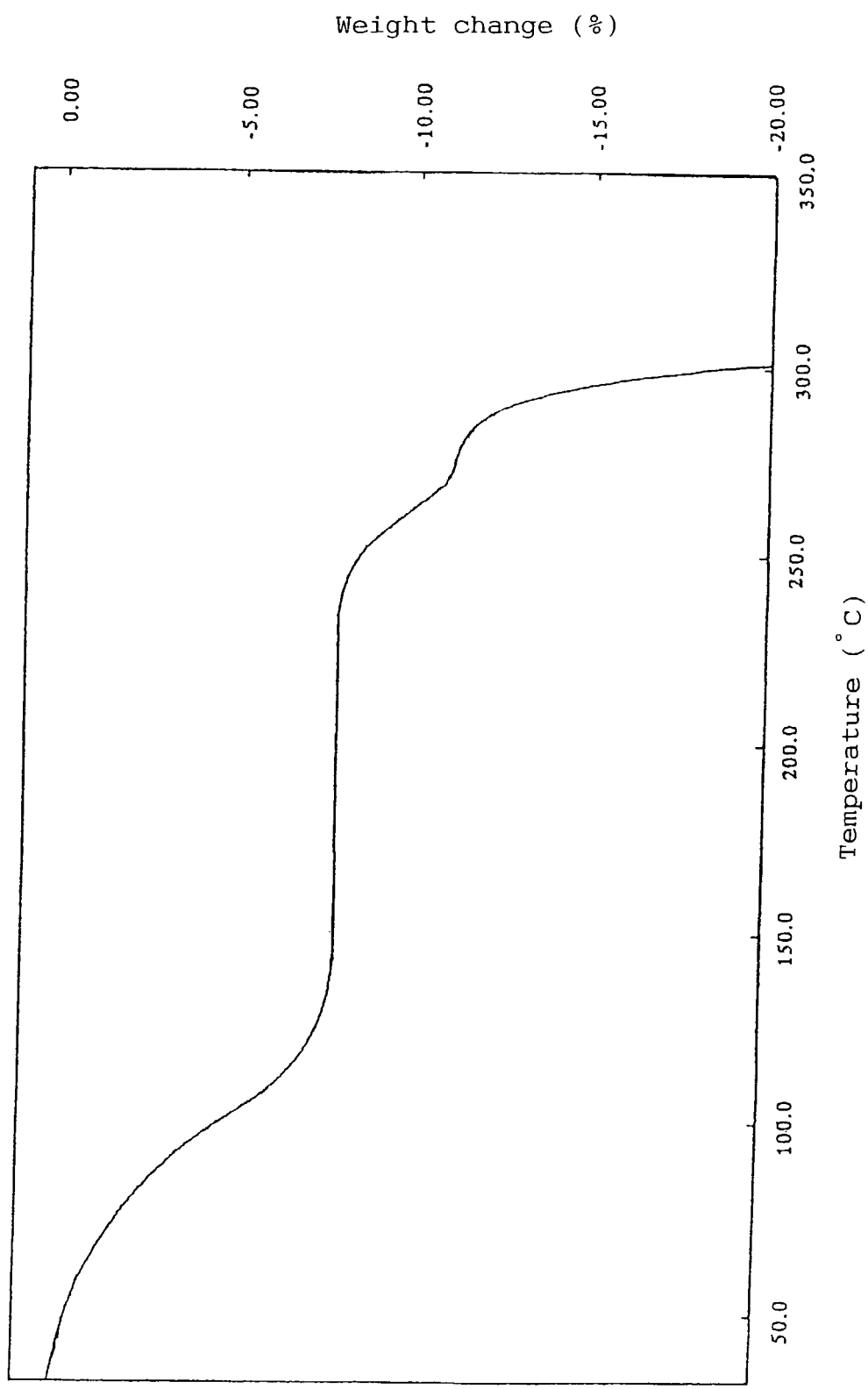
FIG. 47 is a thermogravimetric curve for the cyclotetrasaccharide, penta- to hexa-hydrate, in a crystalline form, of the present invention, when determined on thermogravimetric analysis.

The thermogravimetric analysis of the cyclotetrasaccharide in a crystalline form gave a thermogravimetric curve in FIG. 47. Based on the relationship between the weight change and the temperature, it was successively found that the weight reduction corresponding to four or five moles of water was observed up to a temperature of 150° C., the weight reduction corresponding to one mole of water at around 250° C., and the weight reduction corresponding to the decomposition of cyclotetrasaccharide at a temperature of about 280° C. or higher. These results confirmed that the cyclotetrasaccharide crystal, penta- or hexa-hydrate, of the present invention releases four or five moles of water to changes into a monohydrate crystal when heated up to 150° C. at normal pressure, and further releases one mole of water to change into an anhydrous crystal after being heated up to 250° C.

Experiment 31

Conversion into Cyclotetrasaccharide, Monohydrate

Figure 48:
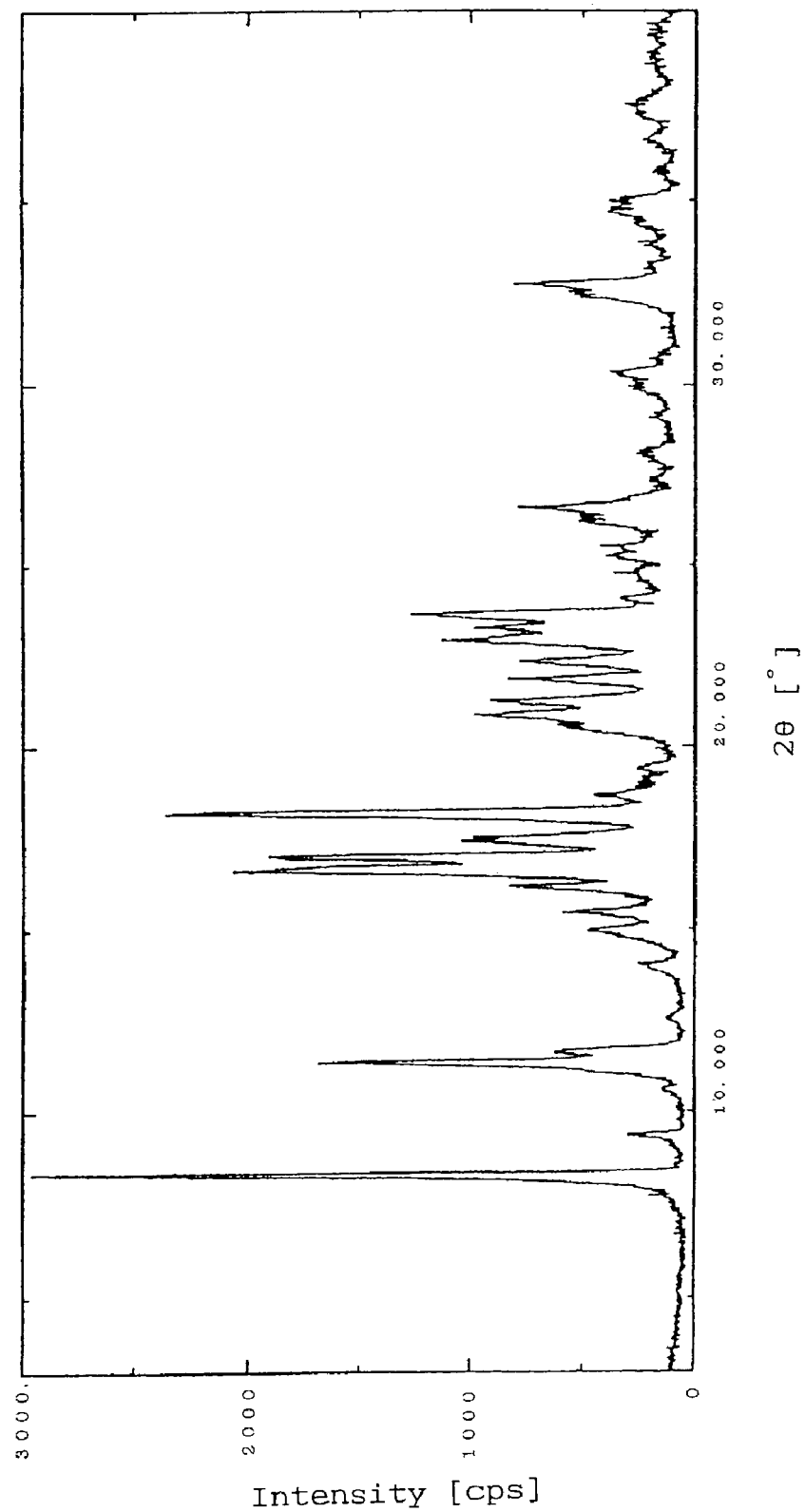
FIG. 48 is an x-ray diffraction spectrum for the cyclotetrasaccharide, monohydrate, in a crystalline form, of the present invention, when determined on x-ray powder diffraction analysis.
Figure 49:
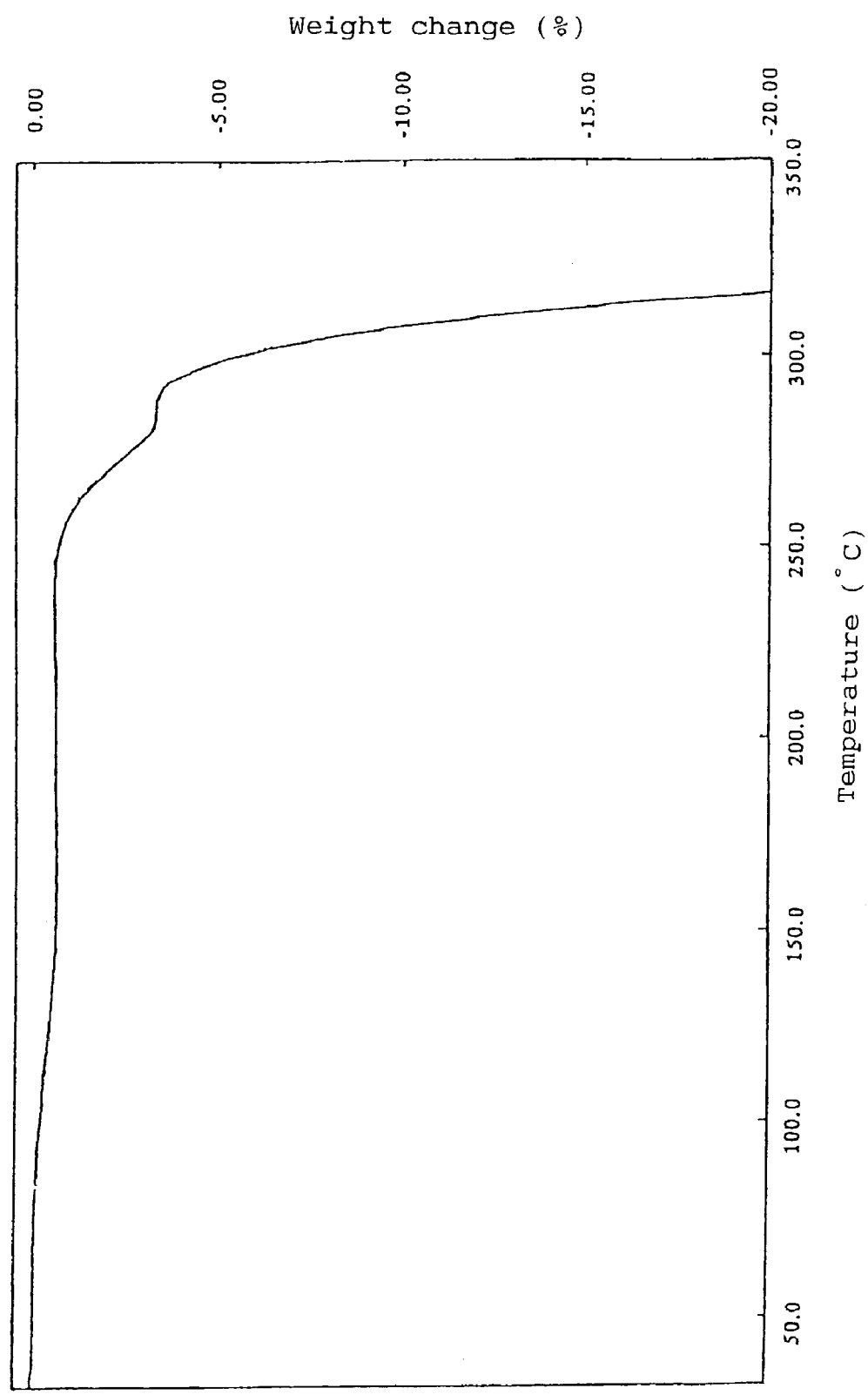
FIG. 49 is a thermogravimetric curve for the cyclotetrasaccharide, monohydrate, in a crystalline form, of the present invention, when determined on thermogravimetric analysis.

Cyclotetrasaccharide, penta- or hexa-hydrate, in a crystalline powder form, obtained by the method in Experiment 30, was placed in a glass vessel, and kept in an oil bath, which had been preheated at 140° C., for 30 min. Unlike quite different from the result from the powder x-ray diffraction analysis of the intact cyclotetrasaccharide, penta- or hexa-hydrate, the powder x-ray analysis of the cyclotetrasaccharide powder thus obtained gave a characteristic diffraction spectrum having main diffraction angles (2θ) of 8.3°, 16.6°, 17.0°, and 18.2° in FIG. 48. The Karl Fischer method of the crystalline powder revealed that it had a moisture content of about 2.7%, resulting in a finding that it was a crystal of cyclotetrasaccharide having one mole of water per one mole of the crystal. The thermogravimetric analysis of the cyclotetrasaccharide in a crystalline powder gave a thermogravimetric curve in FIG. 49. Based on the relationship between the weight change and the temperature, it was found that the weight reduction corresponding to one mole of water was observed at a temperature of about 270° C. and further observed the weight reduction corresponding to the decomposition of cyclotetrasaccharide per se at a temperature of about 290° C. or higher. These results confirmed that the cyclotetrasaccharide crystal in this experiment was cyclotetrasaccharide, monohydrate.

Experiment 32

Conversion into Anhydrous Crystal

Figure 50:
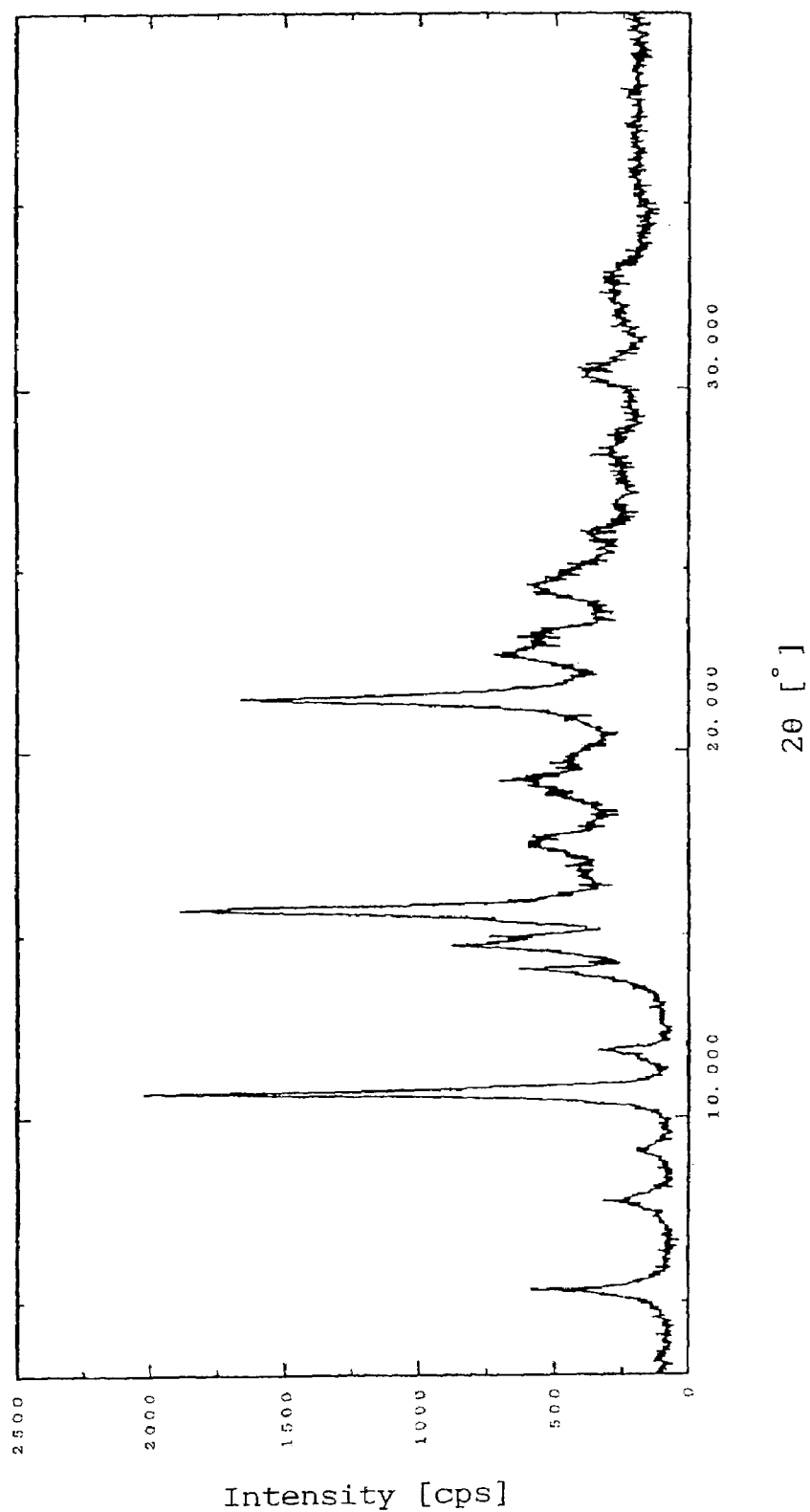
FIG. 50 is an x-ray diffraction spectrum for an anhydrous crystalline powder of the cyclotetrasaccharide, of the present invention, obtained by drying in vacuo at 40° C., when determined on x-ray powder diffraction analysis.
Figure 51:
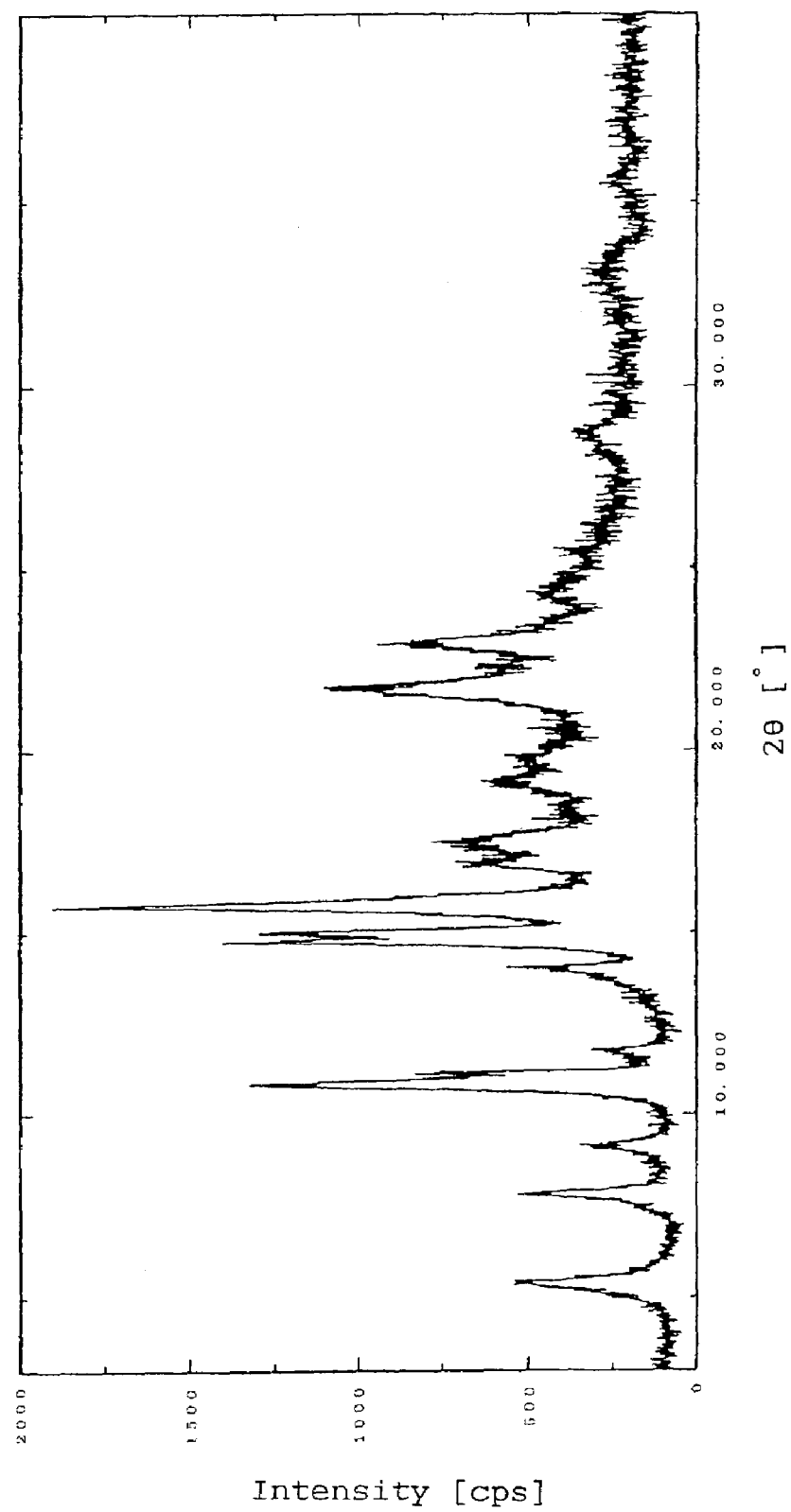
FIG. 51 is an x-ray diffraction spectrum for an anhydrous crystalline powder of the cyclotetrasaccharide, penta- to hexa-hydrate, of the present invention, obtained by drying in vacuo at 120° C., when determined on x-ray powder diffraction analysis.
Figure 52:
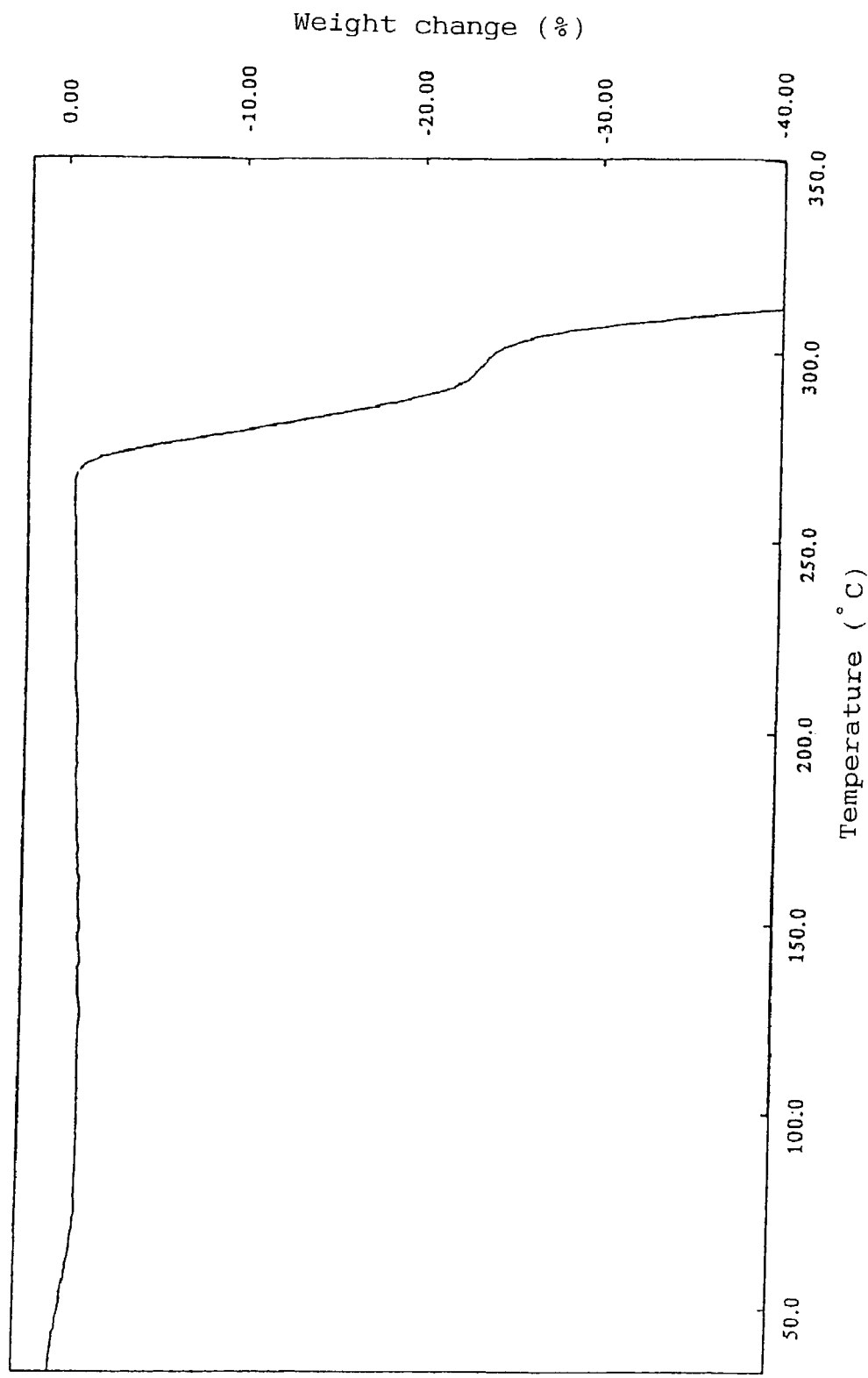
FIG. 52 is a thermogravimetric curve for the anhydrous cyclotetrasaccharide powder of the present invention, when determined on thermogravimetric analysis.

Cyclotetrasaccharide, penta- or hexa-hydrate, in a crystalline powder form, obtained by the method in Experiment 30, was dried in vacuo at 40° C. or 120° C. for 16 hours. The Karl Fischer method of the resulting crystalline powders revealed that the one dried at 40° C. had a moisture content of about 4.2%, while the other dried at 120° C. had a moisture content of about 0.2%, meaning that it was substantially anhydrous. Unlike quite different from the results from powder x-ray diffraction analyses of the cyclotetrasaccharide, penta- or hexa-hydrate, and the cyclotetrasaccharide, monohydrate, before drying in vacua, the powder x-ray analysis of the above cyclotetrasaccharide dried in vacua at 40° and 120° C. gave characteristic diffraction spectra having main diffraction angles (2θ) of 10.8°, 14.7°, 15.0°, 15.7°, and 21.5° in FIG. 50 for 40° C. and FIG. 51 for 120° C. Although there found difference in peak levels between the two diffraction spectra, they had substantially the same peak diffraction angles and they were crystallographically judged to be substantially the same crystalline monohydrate. The fact that the base lines of the diffraction spectra exhibited a mountain-like pattern and the crystallinity of the crystalline monohydrate was lower than those of cyclotetrasaccharide, penta- or hexa-hydrate, and cyclotetrasaccharide, monohydrate, before drying in vacua revealed that there existed an amorphous cyclotetrasaccharide. Based on this, the cyclotetrasaccharide powder with a moisture content of about 4.2%, obtained by drying in vacua at 40° C. was estimated to be a mixture powder of an amorphous cyclotetrasaccharide with such a moisture content and anhydrous crystalline cyclotetrasaccharide. These data revealed that cyclotetrasaccharide, penta- or hexa-hydrate, was converted into amorphous and anhydrous forms when dried in vacua. The thermogravimetric analysis of anhydrous cyclotetrasaccharide with a moisture content of 0.2%, which was conducted similarly as in Experiment 31, observed only a weight reduction as shown in FIG. 52, deemed to be induced by the heat decomposition at a temperature of about 270° C. or higher as shown in FIG. 52.

Experiment 33

Saturation of Cyclotetrasaccharide in Water

To study the saturation concentration of cyclotetrasaccharide in water at 10–90° C., 10 ml of water was placed in a glass vessel with a seal cap, and then mixed with cyclotetrasaccharide, penta- or hexa-hydrate, obtained by the method in Experiment 30, in an excessive amount over a level dissolving completely at respective temperatures, cap-sealed, and stirred for two days while keeping at respective temperatures of 10–90° C. until being saturated. Each resulting saturated solution of cyclotetrasaccharide was membrane filtered to remove undissolved cyclotetrasaccharide, and each filtrate was then examined for moisture content by the drying loss method to determine a saturation concentration of cyclotetrasaccharide at respective temperatures. The results are in Table 34.

TABLE 34

| Temperature (° C.) | Saturation concentration (%) |
|---|---|
| 10 | 30.3 |
| 30 | 34.2 |
| 50 | 42.6 |
| 70 | 53.0 |
| 90 | 70.5 |

Experiment 34

Thermostability

A crystalline cyclotetrasaccharide, penta- or hexa-hydrate, obtained by the method in Experiment 30, was dissolved in water into a 10% (w/v) aqueous solution of cyclotetrasaccharide, and eight milliliters of which was placed in a glass test tube, followed by sealing the test tube and heating the aqueous solution at 120° C. for 30–90 min. After the heating, the aqueous solution was cooled under atmospheric conditions and measured for coloration degree and determined for purity on HPLC. The coloration degree was evaluated based on the absorbance in a cell with a 1-cm light pass at a wavelength of 480 nm. The results are in Table 35.

TABLE 35

| Heating time (min) | Coloration degree ($A_{480\ nm}$) | Purity (%) |
|---|---|---|
| 0 | 0.00 | 100 |
| 30 | 0.00 | 100 |
| 60 | 0.00 | 100 |
| 90 | 0.00 | 100 |

As evident from the results in Table 35, it was revealed that cyclotetrasaccharide is a thermostable saccharide because an aqueous solution of cyclotetrasaccharide was not colored and the purity of the saccharide composition was not lowered even when heated at a high temperature of 120° C.

Experiment 35 pH Stability

A crystalline cyclotetrasaccharide, penta- or hexa-hydrate, obtained by the method in Experiment 30, was dissolved in 20 mM buffers with different pHs into a 4% (w/v) cyclotetrasaccharide solution with a pH of 2–10. Eight milliliters of each solution was placed in a glass test tube, followed by sealing the test tube and heating the solution at 100° C. for 24 hours. After cooling, each solution was measured for coloration degree and determined for purity on HPLC. The coloration degree was evaluated based on the absorbance in a cell with a 1-cm light pass at a wavelength of 480 nm. The results are in Table 36.

TABLE 36

| pH (type of buffer) | Coloration degree ($A_{480\ nm}$) | Purity (%) |
|---|---|---|
| 2.0 (Acetate buffer) | 0.00 | 93 |
| 3.0 (Acetate buffer) | 0.00 | 100 |
| 4.0 (Acetate buffer) | 0.00 | 100 |
| 5.0 (Acetate buffer) | 0.00 | 100 |
| 6.0 (Tris-HCl buffer) | 0.00 | 100 |
| 7.0 (Tris-HCl buffer) | 0.00 | 100 |
| 8.0 (Tris-HCl buffer) | 0.00 | 100 |
| 9.0 (Ammonium buffer) | 0.00 | 100 |
| 10.0 (Ammonium buffer) | 0.00 | 100 |

As evident from the results in Table 36, an aqueous solution of cyclotetrasaccharide was not colored even when heated at 100° C. for 24 hours in a wide pH range from 2 to 10, and the purity of the saccharide composition was not lowered at all in a pH range from 3 to 10, even though the purity was slightly lowered at pH 2, and these facts revealed that cyclotetrasaccharide was highly stable in a relatively wide pH range, i.e., an acid pH range from 3 to 5, a neutral pH range from 6 to 8, and an alkaline pH range from 9 to 10.

Experiment 36

Amino Carbonyl Reaction

A crystalline cyclotetrasaccharide, penta- or hexa-hydrate, obtained by the method in Experiment 30, was dissolved in water, and then admixed with commercialized special grade glycine and phosphate buffer, and the resulting mixture was then adjusted to pH 7.0 with 50 mM phosphate buffer to obtain a 10% (w/v) cyclotetrasaccharide solution containing 1% (w/v) glycine. Four milliliters of the resulting solution were placed in a glass test tube, sealed, and heated at 100° C. for 30 to 90 min. After allowing to stand for cooling at ambient temperature, each of the resulting solutions was measured for coloration degree to examine on their amino carbonyl reactivity. The coloration degree was evaluated based on the absorbance in a cell with 1-cm light pass at a wavelength of 480 nm. The results are in Table 37.

TABLE 37

| Heating time (min) | Coloration degree ($A_{480\ nm}$) |
|---|---|
| 0 | 0.00 |
| 30 | 0.00 |
| 60 | 0.00 |
| 90 | 0.00 |

As evident from the results in Table 37, cyclotetrasaccharide was not colored even when heated in the presence of glycine, meaning that the saccharide does not induce browning with glycine, i.e., cyclotetrasaccharide is a stable saccharide which does not induce the amino carbonyl reaction, alias the Millard reaction.

Experiment 37

Amino Carbonyl Reaction

A crystalline cyclotetrasaccharide, penta- or hexa-hydrate, obtained by the method in Experiment 30, and a commercialized polypeptone, Nihonseiyaku K.K., Tokyo, Japan, were dissolved in deionized water to obtain a 10% (w/v) cyclotetrasaccharide solution containing 5% (w/v) polypeptone. Four milliliters of the resulting solution were placed in a glass test tube, sealed, and heated at 100° C. for 30 to 90 min. After allowing to stand for cooling at ambient temperature, each of the resulting solution was measured for coloration degree to examine on their amino carbonyl reactivity. In parallel, as a control, a solution with only polypeptone was provided and similarly treated as above. The coloration degree was evaluated based on the level of the absorbance, measured in a cell with 1-cm light pass at a wavelength of 480 nm, minus the one of the control. The results are in Table 38.

TABLE 38

| Heating time (min) | Coloration degree ($A_{480\ nm}$) |
|---|---|
| 0 | 0.00 |
| 30 | 0.00 |
| 60 | 0.00 |
| 90 | 0.00 |

As evident from the results in Table 38, it was revealed that cyclotetrasaccharide did not induce browning with polypeptone when heated in the presence of polypeptone, i.e., the saccharide is a stable saccharide which substantially does not induce the amino carbonyl reaction.

Experiment 38

Inclusion Action

A crystalline cyclotetrasaccharide, penta- or hexa-hydrate, obtained by the method in Experiment 30, and a commercialized polypeptone, Nihonseiyaku K. K., Tokyo, Japan, were dissolved in deionized water to obtain a 10% (w/v) cyclotetrasaccharide solution containing 5% (w/v) polypeptone. Four milliliters of the resulting solution were placed in a glass test tube, sealed, and heated at 100° C. for 30 to 90 mm. After allowing to stand for cooling at ambient temperature, each of the resulting solutions was measured for coloration degree to examine on their amino carbonyl reactivity. In parallel, as a control, a solution with only polypeptone was provided and similarly treated as above. The coloration degree was evaluated based on the level of the absorbance, measured in a cell with 1-cm light pass at a wavelength of 480 nm, minus the control. The results are in Table 38.

To measure the amount of the inclusion products in the resulting lyophilized powders, one gram of each powder was dissolved in five milliliters water and extracted after admixing with five milliliters of diethylether. The extraction was repeated, and the resulting extracts were quantified on gas chromatography. The results are in Table 39.

TABLE 39

| Inclusion product | Inclusion amount (mg/g lyophilized powder) | |
|---|---|---|
| | Cyclotetrasaccharide | ISOELITE P (control) |
| Methanol | 6.71 | 2.92 |
| Ethanol | 17.26 | 8.92 |
| Acetic acid | 67.74 | 30.57 |

As evident from the results in Table 39, it was revealed that cyclotetrasaccharide has inclusion ability about 2-folds higher than that of the branched cyclodextrin by weight.

Experiment 39

Sweetening Power

A crystalline cyclotetrasaccharide, penta- or hexa-hydrate, obtained by the method in Experiment 30, was dissolved in deionized water to obtain 10–30% (w/v) aqueous solutions of cyclotetrasaccharide for test solutions on sweetening power. Using a 6% (w/v) aqueous solution of a commercialized granulated sugar as a standard, a sensory test with eight panelists was conducted. As a result, the sweetening power of cyclotetrasaccharide was about 27% of that of sucrose.

Experiment 40

Digestion Test

Using a crystalline cyclotetrasaccharide, penta- or hexahydrate, obtained by the method in Experiment 30, the digestibility of cyclotetrasaccharide in vitro by salivary amylase, synthetic gastric juice, amylopsin, and intestinal mucosal enzyme was carried out in accordance with the method as reported by K. Okada et al. in *JOURNAL OF JAPANESE SOCIETY OF NUTRITION AND FOOD SCIENCE*, Vol. 43, No. 1, pp. 23–29 (1990). As a control, maltitol known as a substantially non-digestive saccharide was used. The results are in Table 40.

TABLE 40

| | Decomposition percentage (%) by digestive enzyme | |
|---|---|---|
| Digestive enzyme | Cyclotetrasaccharide | Maltitol (Control) |
| Salivary amylase | 0.0 | 0.0 |
| Synthetic gastric juice | 0.0 | 0.0 |
| Amylopsin | 0.0 | 0.0 |
| Small intestinal mucosal enzyme | 0.74 | 4.0 |

As evident from the results in Table 40, cyclotetrasaccharide was not completely digested by salivary amylase, synthetic gastric juice, and amylopsin, but slightly digested by intestinal mucosal enzyme at a digestibility as low as 0.74% corresponding to ⅕ of that of maltitol as a control. These results confirmed that cyclotetrasaccharide is a highly undigestible saccharide.

Experiment 41

Fermentation Test

Using a crystalline cyclotetrasaccharide, penta- or hexahydrate, obtained by the method in Experiment 30, the fermentability of cyclotetrasaccharide by an internal content of rat cecum was tested in accordance with the method by T. Oku in "*Journal of Nutritional Science and Vitaminology*", Vol. 37, pp. 529–544 (1991). The internal content of rat cecum was collected by anesthetizing a Wister male rat with ether, allowing the rat to die, collecting the internal content under anaerobic conditions, and suspending the resultant with 4-fold volumes of a 0.1 M aqueous solution of sodium bicarbonate. Cyclotetrasaccharide was added in an amount of about 7% by weight to the internal content of rat cecum, and the contents of cyclotetrasaccharide still remained just after and 12 hours after the addition of the internal content was quantified on gas chromatography. As a result, the contents of cyclotetrasaccharide of the former and latter were respectively 68.0 mg and 63.0 mg per one gram of the internal content of rat cecum. These data confirmed that cyclotetrasaccharide is a substantially non-fermentable saccharide.

Experiment 42

Assimilation Test

Using a crystalline cyclotetrasaccharide, penta- or hexa-hydrate, obtained by the method in Experiment 30, the assimilability of cyclotetrasaccharide by an internal content of rat cecum was studied in accordance with the method disclosed in "A Color Atlas of Anaerobic Bacteria", edited by Tomotari MITSUOKA, published by Kabushiki Kaisha Sobunsha, Tokyo, Japan, (1984). About $10^7$ CFU (colony forming units) of pre-cultured fresh microorganisms were inoculated into five milliliters of PYF medium admixed with 0.5% cyclotetrasaccharide, and cultured at 37° C. for four days under anaerobic conditions. As a control, glucose was used as an easily assimilable saccharide. The assimilability was judged negative (−) when the post culture had a pH of 6.0 or higher and judged positive (+) when the post culture had a pH below 6.0. The judgement of assimilability was confirmed by measuring the content of saccharide, remained in the culture, using the anthrone method to determine the lowered saccharide level. The results are in Table 41.

TABLE 41

| Strain of intestinal microorganism | Assimilability | |
|---|---|---|
| | Cyclotetrasaccharide | Glucose (control) |
| *Bacteroides vulgatus* JCM 5826 | − | + |
| *Bifidobacterium adolescentis* JCM 1275 | − | + |
| *Clostridium perfringens* JCM 3816 | − | + |
| *Escherichia coli* IFO 3301 | − | + |
| *Eubacterium aerofaciens* ATCC 25986 | − | + |
| *Lactobacillus acidophilus* JCM 1132 | − | + |

As evident from the results in Table 41, it was confirmed that cyclotetrasaccharide was not assimilated by all the strains tested, but glucose as a control was assimilated by all the strains tested. Thus, cyclotetrasaccharide was confirmed to be a highly non-assimilable saccharide by intestinal microorganisms.

Experiment 43

Acute Toxicity Test

The acute toxicity of a crystalline cyclotetrasaccharide, penta- or hexa-hydrate, obtained by the method in Experiment 30, was tested by orally administering it to mice. As a result, it was revealed that cyclotetrasaccharide had relatively low toxicity and did not induce death of mice even when administered at a highest possible dose. Based on this, the $LD_{50}$ of cyclotetrasaccharide was at least 50 g/kg mouse body weight, though the data were not so accurate.

Based on the results in Experiments 40 to 43, cyclotetrasaccharide is not substantially assimilated or absorbed by living bodies when orally taken and can be expected to be used as a non- or low-caloric edible material in diet sweeteners, fillers for sweeteners with a relatively high sweetening power, and viscosity agents, fillers and bodies for diet food products, and further can be used as an edible fiber and food material for substituting fats.

The following Example A describes the cyclotetrasaccharide and the process for producing saccharide composition comprising the same, and Example B describes the composition comprising the cyclotetrasaccharide or the saccharide composition:

EXAMPLE A-1

A microorganism of the species *Bacillus globisporus* C9, FERM BP-7143, was cultured by a fermentor for 48 hours in accordance with the method in Experiment 3. After completion of the culture, the resulting culture was filtered with an SF membrane to remove cells and to collect about 18L of a culture supernatant. Then the culture supernatant was concentrated with a UF membrane to collect about one liter of a concentrated enzyme solution containing 8.8 units/ml of the α-isomaltosylglucosaccharide-forming enzyme of the present invention and 26.7 units/ml of α-isomaltosyl-transferring enzyme.

A potato starch was prepared into an about 2% starch suspension, admixed with calcium chloride to give a final concentration of 1 mM, adjusted to pH 6.0, and heated at 95° C. for about 20 min to gelatinize the starch. The resulting mixture was then cooled to about 35° C. and admixed with 0.25 ml of the above concentrated enzyme solution to one gram of the starch, d.s.b., followed by the enzymatic reaction at pH 6.0 and 35° C. for 48 hours. The reaction mixture was heated to and kept at 95° C. for 10 min, and then cooled and filtered. The filtrate was in a conventional manner decolored with an activated charcoal, desalted and purified with ion exchangers in H- and OH-forms, and further concentrated and spray-dried to obtain a powder containing cyclotetrasaccharide in a yield of about 90% to the material starch, d.s.b.

Since the product contains, on a dry solid basis, 0.7% glucose, 1.4% isomaltose, 11.1% maltose, 62.1% cyclotetrasaccharide, and 24.7% of other saccharides and has a mild sweetness and an adequate viscosity, moisture-retaining ability, and inclusion ability, it can be advantageously used in a variety of compositions such as food products, cosmetics, and pharmaceuticals as a sweetener, taste-improving agent, quality-improving agent, syneresis-preventing agent, stabilizer, discoloration-preventing agent, filler, inclusion agent, and base for pulverization.

EXAMPLE A-2

A potato starch was prepared into an about 6% starch suspension, admixed with calcium carbonate to give a final concentration of 0.1%, adjusted to pH 6.0, further admixed with 0.2% per gram starch, d.s.b., of "TERMAMYL 60L", an α-amylase commercialized by Novo Industri A/S, Copenhagen, Denmark, and then heated at 95° C. for about 10 min. Thereafter, the mixture was autoclaved at 120° C. for 20 min and then promptly cooled to about 35° C. to obtain a liquefied solution with a DE (dextrose equivalent) of about four. To the liquefied solution was added 0.25 ml per gram starch, d.s.b., of the concentrated enzyme solution in Example A-1 containing α-isomaltosylglucosaccharide-forming enzyme and α-isomaltosyl-transferring enzyme, followed by the enzymatic reaction at pH 6.0 and 35° C. for 48 hours. The reaction mixture was heated to and kept at 95° C. for 10 min and then cooled and filtered. The filtrate was in a conventional manner decolored with an activated charcoal, desalted and purified with ion exchangers in H- and OH-forms, and then concentrated into a 60% cyclotetrasaccharide syrup in a yield of about 90% to the material starch, d.s.b.

Since the product contains, on a dry solid basis, 0.9% glucose, 1.5% isomaltose, 11.3% maltose, 60.1% cyclotetrasaccharide, and 26.2% of other saccharides and has a mild sweetness and an adequate viscosity, moisture-retaining ability, and inclusion ability, it can be advantageously used in a variety of compositions such as food products, cosmetics, and pharmaceuticals as a sweetener, taste-improving agent, quality-improving agent, syneresis-preventing agent, stabilizer, discoloration-preventing agent, filler, and inclusion agent.

EXAMPLE A-3

A microorganism of the species *Bacillus globisporus* C11, FERM BP-7144, was cultured by a fermentor for 48 hours in accordance with the method in Experiment 6. After completion of the culture, the resulting culture was filtered with an SF membrane to remove cells and to collect about 18L of a culture supernatant. Then the culture supernatant was concentrated with a UF membrane to collect about one liter of a concentrated enzyme solution containing 9.0 units/ml of the α-isomaltosylglucosaccharide-forming enzyme of the present invention and 30.2 units/ml of α-isomaltosyl-transferring enzyme. A tapioca starch was prepared into an about 25% starch suspension which was then admixed with 0.2% per gram starch, d.s.b., of "NEO-SPITASE", an α-amylase commercialized by Nagase Biochemicals, Ltd., Kyoto, Japan. Thereafter, the reaction mixture was autoclaved at 120° C. for 20 min and then promptly cooled to about 35° C. to obtain a liquefied solution with a DE of about four. To the liquefied solution was added 0.25 ml per gram starch, d.s.b., of the above concentrated enzyme solution, containing α-isomaltosylglucosaccharide-forming enzyme and α-isomaltosyl-transferring enzyme, and further added 10 units/g starch, d.s.b., of CGTase commercialized by Hayashibara Biochemical Laboratories, Inc., Okayama, Japan, followed by the enzymatic reaction at pH 6.0 and 35° C. for 48 hours. The reaction mixture was heated to and kept at 95° C. for 30 min and then cooled and filtered, and then adjusted to pH 5.0 and 50° C. and admixed with 300 units/g starch, d.s.b., of "TRANSGLUCOSIDASE L AMANO™", an α-glucosidase commercialized by Amano Pharmaceutical Co., Ltd., Aichi, Japan, followed by the enzymatic reaction for 24 hours. Further the reaction mixture was mixed with 30 units/g starch, d.s.b., "GLUCOZYME", a glucoamylase preparation commercialized by Nagase Biochemicals, Ltd., Kyoto, Japan, and then enzymatically reacted for 17 hours. The reaction mixture thus obtained was heated to and kept at 95° C. for 30 min, and then cooled and filtered to obtain a filtrate. The resulting filtrate was in a conventional manner decolored with an activated charcoal, desalted and purified with ion exchangers in H- and OH-forms, and then concentrated into a 60% cyclotetrasaccharide syrup in a yield of about 90% to the material starch, d.s.b.

Since the product contains, on a dry solid basis, 38.4% glucose, 58.1% cyclotetrasaccharide, and 3.5% of other saccharides and has a mild sweetness and an adequate viscosity, moisture-retaining ability, and inclusion ability, it can be advantageously used in a variety of compositions such as food products, cosmetics, and pharmaceuticals as a sweetener, taste-improving agent, quality-improving agent, syneresis-preventing agent, stabilizer, discoloration-preventing agent, filler, and inclusion agent.

EXAMPLE A-4

A potato starch was prepared into an about 20% starch suspension, admixed with calcium carbonate to give a final concentration of 0.1%, adjusted to pH 6.5, further admixed with 0.3% per gram starch, d.s.b., of "TERMAMYL 60L", an α-amylase commercialized by Novo Industri A/S, Copenhagen, Denmark, and then enzymatically reacted at 95° C. for about 15 min. Thereafter, the mixture was autoclaved at 120° C. for 20 min and then promptly cooled to about 35° C. to obtain a liquefied solution with a DE of about four. To the liquefied solution was added 0.25 ml per gram starch, d.s.b., of the concentrated enzyme solution in Example A-3 containing α-isomaltosylglucosaccharide-forming enzyme and α-isomaltosyl-transferring enzyme, followed by the enzymatic reaction at pH 6.0 and 35° C. for 48 hours. The reaction mixture was heated to and kept at 95° C. for 30 min and then adjusted to pH 5.0 and 50° C., followed by the enzymatic reaction for 24 hours after the addition of 300 units/g solid of "TRANSGLUCOSIDASE L AMANO™", an α-glucosidase commercialized by Amano Pharmaceutical Co., Ltd., Aichi, Japan, and then the enzymatic reaction for 17 hours after the addition of 30 units/g solid of "GLUCOZYME", a glucoamylase preparation commercialized by Nagase Biochemicals, Ltd., Kyoto, Japan. The resulting reaction mixture was heated to and kept at 95° C. for 30 min, and then cooled and filtered. The filtrate thus obtained was in a conventional manner decolored with an activated charcoal, desalted and purified with ion exchangers in H- and OH-forms, and then concentrated into a 60% cyclotetrasaccharide syrup in a yield of about 90% to the material starch, d.s.b.

Since the product contains, on a dry solid basis, 34.2% glucose, 62.7% cyclotetrasaccharide, and 3.1% of other saccharides and has a mild sweetness and an adequate viscosity, moisture-retaining ability, and inclusion ability, it can be advantageously used in a variety of compositions such as food products, cosmetics, and pharmaceuticals as a sweetener, taste-improving agent, quality-improving agent, syneresis-preventing agent, stabilizer, discoloration-preventing agent, filler, and inclusion agent.

EXAMPLE A-5

Cyclotetrasaccharide syrup obtained by the method in Example A-3 was column chromatographed using "AMBERLITE CR-1310 (Na-form)", a strong acid cation-exchange resin commercialized by Japan Organo Co., Ltd., Tokyo, Japan. The resin was packed into four jacketed stainless steel columns having a diameter of 5.4 cm, which were then cascaded in series to give a total gel bed depth of 20 m. Under the conditions of keeping the inner column temperature at 60° C., the saccharide syrup was fed to the columns in a volume of 5% (v/v) and fractionated by feeding to the columns hot water heated to 60° C. at an SV (space velocity) of 0.13 to obtain high cyclotetrasaccharide content fractions while monitoring the saccharide composition of eluate on HPLC, and then purifying the fractions to obtain a high cyclotetrasaccharide content solution in a yield of about 21% to the material starch, d.s.b. The solution contained about 98%, d.s.b., of cyclotetrasaccharide.

The solution was concentrated to give a concentration of about 70% and then placed in a crystallizer, admixed with about 2% of crystalline cyclotetrasaccharide, penta- or hexa-hydrate, and gradually cooled to obtain a massecuite with a crystallinity of about 45%. The massecuite was sprayed from a nozzle equipped on top of a drying tower at a high pressure of 150 kg/cm$^2$. Simultaneously, hot air heated to 85° C. was being blown down from the upper part of the drying tower, and the resulting crystalline powder was collected on a transporting wire conveyor provided on the basement of the tower and gradually moved out of the tower while blowing thereunto a hot air heated to 45° C. The resulting crystalline powder was injected to an ageing tower and aged for 10 hours while a hot air was being blown to the contents to complete the crystallization and drying to obtain a crystalline powder of cyclotetrasaccharide, penta- or hexa-hydrate.

Since the product has a relatively low reducibility, does substantially neither cause the amino carbonyl reaction nor exhibit hygroscopicity, and has a satisfactory handleability, mild low sweetness, adequate viscosity, moisture-retaining ability, inclusion ability, and substantially non-digestibility, it can be advantageously used in a variety of compositions such as food products, cosmetics, and pharmaceuticals as a sweetener, materials for relatively low caloric foods, taste-improving agent, flavor and taste-improving agent, quality-improving agent, syneresis-preventing agent, stabilizer, discoloration-preventing agent, filler, inclusion agent, and base for pulverization.

EXAMPLE A-6

To increase the content of cyclotetrasaccharide of cyclotetrasaccharide syrup obtained by the method in Example A-4, the syrup as a material saccharide solution was column chromatographed using a strong acid cation-exchange resin in accordance with the method in Example A-5, followed by collecting and purifying high cyclotetrasaccharide content fractions to obtain a high cyclotetrasaccharide content solution in a yield of about 90% to the material starch, d.s.b.

The solution was concentrated to give a concentration of about 85% and then gradually cooled while stirring to proceed crystallization. The resultant was transferred to a plastic vessel and allowed to stand at ambient temperature for crystallizing and ageing the contents. The resulting block was pulverized by a cutter to obtain a crystalline powder of cyclotetrasaccharide, penta- or hexa-hydrate.

Since the product does not substantially have hygroscopicity, has a satisfactory handleability, mild low sweetness, adequate viscosity, moisture-retaining ability, inclusion ability, and substantially non-digestibility, it can be advantageously used in a variety of compositions such as food products, cosmetics, and pharmaceuticals as a sweetener, materials for relatively low caloric foods, taste-improving agent, flavor and taste-improving agent, quality-improving agent, syneresis-preventing agent, stabilizer, discoloration-preventing agent, filler, inclusion agent, and base for pulverization.

EXAMPLE A-7

A high cyclotetrasaccharide content solution, obtained by the method in Example A-6, was continuously crystallized while concentrating. The resulting massecuite was separated by a basket-type centrifuge to obtain crystals which were then sprayed with a small amount of water to obtain a high purity cyclotetrasaccharide, penta- or hexa-hydrate, in a yield of about 55%, d.s.b., to the material contents.

Since the product contains at least 98%, d.s.b., of a high purity crystalline cyclotetrasaccharide, penta- or hexa-hydrate, has a relatively low reducibility, does substantially neither cause the amino carbonyl reaction nor exhibit hygroscopicity, and has a satisfactory handleability, mild low sweetness, adequate viscosity, moisture-retaining ability, inclusion ability, and substantially non-digestibility, it can be advantageously used in a variety of compositions such as food products, cosmetics, pharmaceuticals, industrial reagents, and chemical materials as a sweetener, materials for relatively low caloric foods, taste-improving agent, flavor and taste-improving agent, quality-improving agent, syneresis-preventing agent, stabilizer, discoloration-preventing agent, filler, inclusion agent, and base for pulverization.

EXAMPLE A-8

A liquid nutrient culture medium, consisting of 5.0% (w/v) corn phytoglycogen, 1.0% (w/v) of "ASAHIMEAST", a yeast extract, 0.1% (w/v) of dipotassium phosphate, 0.06% (w/v) of sodium phosphate dodecahydrate, 0.05% (w/v) magnesium sulfate heptahydrate, and water, was placed in a 30-L fermentor in a volume of about 20L, autoclaved at 121° C. for 20 minutes to effect sterilization, cooled to 27° C., inoculated with 1% (v/v) of a seed culture of *Bacillus globisporus* C11, FERM BP-7144, prepared in accordance with the method in Experiment 6, and incubated at 27° C. and pH 6.0–7.0 for 72 hours under aeration and agitation conditions. The resultant culture was sterilized by heating at 121° C. for 20 min, cooled, and centrifuged. The supernatant was collected and membrane filtered with a UF membrane. The resulting filtrate was in a usual manner decolored with an activated charcoal and desalted and purified with ion exchangers in H- and OH-forms to obtain a solution containing cyclotetrasaccharide in a yield of about 40%, d.s.b., to the material phytoglycogen. The solution thus obtained contained about 87%, d.s.b., of cyclotetrasaccharide.

The above solution was continuously crystallized while concentrating, and the resulting massecuite was separated by a basket-type centrifuge to obtain crystals which were then sprayed with a small amount of water to obtain cyclotetrasaccharide, penta- or hexa-hydrate, with a purity of at least 98% in a yield of about 25%, d.s.b., to the material phytoglycogen.

Since the product, a high purity cyclotetrasaccharide, penta- or hexa-hydrate, has a relatively low reducibility, does substantially neither cause the amino carbonyl reaction nor exhibit hygroscopicity, and has a satisfactory handleability, mild low sweetness, adequate viscosity, moisture-retaining ability, inclusion ability, and substantially non-digestibility, it can be advantageously used in a variety of compositions such as food products, cosmetics, pharmaceuticals, industrial reagents, and chemical materials as a sweetener, materials for relatively low caloric foods, taste-improving agent, flavor and taste-improving agent, quality-improving agent, syneresis-preventing agent, stabilizer, discoloration-preventing agent, filler, inclusion agent, and base for pulverization.

EXAMPLE A-9

A microorganism of the species *Bacillus globisporus* N75, FERM BP-7591, was cultured by a fermentor for 48 hours in accordance with the method in Experiment 10. After completion of the culture, the resulting culture was filtered with an SF membrane to remove cells and to collect about 18L of a culture supernatant. Then the culture supernatant was concentrated with a UF membrane to collect about 800 ml of a concentrated enzyme solution containing 6.0 units/ml of the α-isomaltosylglucosaccharide-forming enzyme of the present invention and 20.0 units/ml of α-isomaltosyl-transferring enzyme. A corn starch was prepared into an about 30% starch suspension which was then admixed with calcium carbonate to give a concentration of 0.1%, adjusted to pH 6.5, admixed with 0.3% per gram starch, d.s.b., of "TERMAMYL 60L", an α-amylase commercialized by Novo Industri A/S, Copenhagen, Denmark,", an α-amylase commercialized by Nagase Biochemicals, Ltd., Kyoto, Japan, and enzymatically reacted at 95° C. for 15 min. Thereafter, the reaction mixture was autoclaved at 120° C. for 20 min and then promptly cooled to about 51° C. to obtain a liquefied solution with a DE of four. To the liquefied solution were added 0.4 ml per gram of the starch, d.s.b., of the above concentrated enzyme solution containing α-isomaltosylglucosaccharide-forming enzyme and α-isomaltosyl-transferring enzyme, and three units/g starch, d.s.b., of CGTase commercialized by Hayashibara Biochemical Laboratories, Inc., Okayama, Japan, followed by the enzymatic reaction at pH 5.5 and 51° C. for 48 hours. Thereafter, the reaction mixture was heated to and kept at 95° C. for 30 min, then adjusted to pH 5.0 and 50° C., followed by the 24-hour enzymatic reaction after the addition of 300 units/g solid of "TRANSGLUCOSIDASE L AMANO™", an α-glucosidase commercialized by Amano Pharmaceutical Co., Ltd., Aichi, Japan, and then the 17-hour enzymatic reaction after the addition of 20 units/g solid of "GLUCOZYME", a glucoamylase preparation commercialized by Nagase Biochemicals, Ltd., Kyoto, Japan. The resulting reaction mixture was heated to and kept at 95° C. for 30 min, cooled, and filtered. The resulting filtrate was in a usual manner decolored with an activated charcoal, desalted and purified with ion-exchangers in H- and OH-forms, and concentrated to obtain a syrup containing 44.0%, d.s.b., of cyclotetrasaccharide. To increase the content of cyclotetrasaccharide, the syrup as a material saccharide solution was column chromatographed using a strong acid cation-exchange resin in accordance with the method in Example A-5, followed by collecting and purifying high cyclotetrasaccharide content fractions and then concentrating and spray drying the resultant to obtain a powder containing cyclotetrasaccharide in a yield of about 45%, d.s.b., to the material starch.

Since the product contains 3.7% glucose, 80.5% cyclotetrasaccharide, and 15.8% other saccharides, has a mild low sweetness, adequate viscosity, moisture-retaining ability, and inclusion ability, it can be advantageously used in a variety of compositions such as food products, cosmetics, pharmaceuticals as a sweetener, taste-improving agent, quality-improving agent, syneresis-preventing agent, stabilizer, discoloration-preventing agent, filler, inclusion agent, and base for pulverization.

EXAMPLE A-10

A microorganism of the species *Bacillus globiformis* A19, FERM BP-7590, was cultured by a fermentor for 48 hours in accordance with the method in Experiment 14. After completion of the culture, the resulting culture was filtered with an SF membrane to remove cells and to collect about 18L of a culture supernatant. Then the culture supernatant was concentrated with a UF membrane to collect about one liter of a concentrated enzyme solution containing 15.2 units/ml of the α-isomaltosylglucosaccharide-forming enzyme of the present invention and 23.0 units/ml of α-isomaltosyl-transferring enzyme.

A potato starch was prepared into an about 5% starch suspension which was then admixed with calcium carbonate to give a concentration of 0.1%, adjusted to pH 6.0, admixed with 0.2% per gram starch, d.s.b., of "TERMAMYL 60L", an α-amylase commercialized by Novo Industri A/S, Copenhagen, Denmark, and enzymatically reacted at 95° C. for 10 min. Thereafter, the reaction mixture was autoclaved at 120° C. for 20 min and then promptly cooled to about 40° C. to obtain a liquefied solution with a DE of four. To the liquefied solution were added 0.5 ml per gram of the starch, d.s.b., of the concentrated enzyme solution containing α-isomaltosylglucosaccharide-forming enzyme and α-isomaltosyl-transferring enzyme obtained by the above method, and then enzymatically reacted at pH 6.0 and 40° C. for 48 hours. The reaction mixture was heated to and kept at 95° C. for 10 min, then cooled and filtered. The filtrate was in a usual manner decolored with an activated charcoal, desalted and purified with ion-exchangers in H- and OH-forms, and concentrated to obtain a syrup containing 70% (w/v) cyclotetrasaccharide in a yield of about 90%, d.s.b., to the material starch.

Since the product contains 2.5% glucose, 6.3% isomaltose, and 30.1% cyclotetrasaccharide, has a mild sweetness, adequate viscosity, moisture-retaining ability, and inclusion ability, it can be advantageously used in a variety of compositions such as food products, cosmetics, pharmaceuticals as a sweetener, taste-improving agent, quality-improving agent, syneresis-preventing agent, stabilizer, discoloration-preventing agent, filler, and inclusion agent.

EXAMPLE B-1

Sweetener

To 0.8 part by weight of a crystalline tetrasaccharide, penta- or hexa-hydrate, obtained by the method in Example A-7, were homogeneously added 0.2 part by weight of "TREHA", a crystalline trehalose hydrate commercialized by Hayashibara Shoji Inc., Okayama, Japan, 0.01 part by weight of "αG SWEET™" (α-glycosylstevioside commercialized by Toyo Sugar Refining Co., Tokyo, Japan), and 0.01 part by weight of "ASPARTAME" (L-aspartyl-L-phenylalanine methyl ester), and the resulting mixture was fed to a granulator to obtain a sweetener in a granule form. The product has a satisfactory sweetness and a 2-fold higher sweetening power of sucrose. Since crystalline cyclotetrasaccharide, penta- or hexa-hydrate, is scarcely digested and fermented and is substantially free of calorie, the calorie of the product is about 1/10 of that of sucrose with respect to sweetening power. In addition, the product is substantially free from deterioration and stable when stored at ambient temperature. Thus, the product can be suitably used as a high quality low-caloric and less cariogenic sweetener.

EXAMPLE B-2

Hard Candy

One hundred parts by weight of a 55% (w/v) sucrose solution was admixed while heating with 50 parts by weight of a syrup containing cyclotetrasaccharide obtained by the method in Example A-2. The mixture was then concentrated by heating under reduced pressure to give a moisture content of less than 2%, and the concentrate was mixed with 0.6 part by weight of citric acid and an adequate amount of a lemon flavor, followed by forming in a usual manner the resultant into the desired product. The product is a stable, high quality hard candy which has a satisfactory mouth feel, taste, and flavor, less adsorb moisture, and does neither induce crystallization of sucrose nor cause melting.

EXAMPLE B-3

Chewing Gum

Three parts by weight of a gum base were melted by heating to an extent to be softened and then admixed with two parts by weight of anhydrous crystalline maltitol, two parts by weight of xylitol, two parts by weight of a crystalline cyclotetrasaccharide, penta- or hexa-hydrate, obtained by the method in Example A-7, and one part by weight of trehalose, and further mixed with adequate amounts of a flavor and a color. The mixture was in a usual manner kneaded by a roll and then shaped and packed to obtain the desired product. The product thus obtained is a relatively low cariogenic and caloric chewing gum having a satisfactory texture, taste, and flavor.

EXAMPLE B-4

Sweetened Milk

In 100 parts by weight of a fresh milk was dissolved two parts by weight of a crystalline powder of cyclotetrasaccharide, penta- or hexa-hydrate, obtained by the method in Example A-5, and two parts by weight of sucrose, and the solution was sterilized by heating using a plate heater and then concentrated to give a concentration of 70%. The concentrate was aseptically canned to obtain the desired product. Since the product has a mild sweetness and a satisfactory flavor and taste, it can be arbitrarily used for seasoning fruit, coffee, cocoa, and tea.

EXAMPLE B-5

Lactic Acid Beverage

One hundred and seventy-five parts by weight of a skim milk powder, 130 parts by weight of a syrup containing cyclotetrasaccharide, obtained by the method in Example A-4, and 50 parts by weight of "NYUKAOLIGO®", a high lactosucrose content powder commercialized by Hayashibara Shoji Inc., Okayama, Japan, were dissolved in 1,150 parts by weight of water. The resulting solution was sterilized at 65° C. for 30 min, then cooled to 40° C., inoculated in a usual manner with 30 parts by weight of lactic acid bacteria as a starter, and incubated at 37° C. for eight hours to obtain a beverage with lactic acid bacteria. The product can be suitably used as a lactic acid beverage which has a satisfactory flavor and taste, contains oligosaccharides and cyclotetrasaccharide, stably retains the lactic acid bacteria, and has actions of promoting the growth of the bacteria and control the intestinal conditions.

EXAMPLE B-6

Powdered Juice

Thirty-three parts by weight of an orange juice powder, prepared by spray drying, were well mixed by stirring with 50 parts by weight of cyclotetrasaccharide, penta- or hexa-hydrate, obtained by the method in Example A-7, 10 parts by weight of anhydrous crystalline maltitol, 0.65 part by weight of anhydrous citric acid, 0.1 part by weight of malic acid, 0.2 part by weight of 2-O-α-D-glucosyl-L-ascorbic acid, 0.1 part by weight of sodium citrate, 0.5 part by weight of pullulan, and an adequate amount of a powdered flavor. The mixture was pulverized into a minute powder which was then placed in a fluidized-bed granulator adjusted to blow air to 40° C., sprayed with an adequate amount of a concentrated solution enriched with cyclotetrasaccharide as a binder, obtained by the method in Example A-5, granulated for 30 min, weighed, and packed to obtain the desired product. The product is a powdered juice having a fruit juice content of about 30%. Also the product has a high product value as a high quality, low caloric juice because it has no unpleasant taste and smell.

EXAMPLE B-7

Custard Cream

One hundred parts by weight of corn starch, 100 parts by weight of cyclotetrasaccharide obtained by the method in Example A-2, 60 parts by weight of trehalose, 40 parts by weight of sucrose, and one part by weight of salt were sufficiently mixed, and then further mixed with 280 parts by weight of fresh eggs, followed by stirring. To the resulting mixture was gradually admixed with 1,000 parts by weight of a boiling milk. The mixture was continued stirring over a fire, and the heating was stopped when the whole contents became semitransparent after the corn starch was completely gelatinized, followed by cooling the resultant, admixing it with a vanilla flavor, and then weighing, injecting, and packing the resultant to obtain the desired product. The product is a high quality custard cream which has a smooth gloss, a satisfactory flavor and taste, and well-inhibited retrogradation of starch.

EXAMPLE B-8

Chocolate

Forty parts by weight of a cacao paste, 10 parts by weight of a cacao butter, and 50 parts by weight of a crystalline cyclotetrasaccharide monohydrate, obtained by the method in Experiment 24 were mixed, and the mixture was fed to a refiner to lower the granule size and then placed in a conche for kneading at 50° C. over two days and nights. During the processing, 0.5 part by weight of lecithin was added to and well dispersed in the kneaded mixture. Thereafter, the resulting mixture was adjusted to 31° C. using a thermo controller, and then poured into a mold just before solidification of butter, deairated, packed, and solidified by passing through a cooling tunnel kept at 10° C. The solidified contents were removed from the mold and packed to obtain the desired product. The product has substantially no hygroscopicity, satisfactory color, gloss, and internal texture; smoothly melts in the mouth; and has a high quality sweetness and a mild taste and flavor. Also the product can be useful as a low cariogenic, low caloric chocolate.

EXAMPLE B-9

Uiro-no-moto (a Premix of Uiro (Sweet Rice Jelly))

To 90 parts by weight of rice powder were added 20 parts by weight of corn starch, 70 parts by weight of anhydrous crystalline maltitol, 50 parts by weight of a powder containing cyclotetrasaccharide obtained by the method in Example A-1, and four parts by weight of pullulan, and the resulting mixture was mixed to homogeneity into a premix of uiro-no-moto. The premix and adequate amounts of matcha (a green tea powder) and water were kneaded and then placed in a container and steamed for 60 min to obtain a uiro with matcha. The product has a satisfactory gloss, mouth feel, flavor, and taste, and it can be suitably used as a long shelf-life low caloric uiro in which the retrogradation of starch is well prevented.

EXAMPLE B-10

An (a Bean Jam)

Ten parts by weight of beans as a material in a usual manner were boiled in a usual manner after the addition of water, removed the astringency, lye, and water-soluble impurities to obtain about 21 parts by weight of raw bean jam in the form of a granule. To the raw bean jam were added 14 parts by weight of sucrose, five parts by weight of a syrup containing cyclotetrasaccharide, obtained by the method in Example A-3, and four parts by weight of water, and the resulting mixture was boiled, admixed with a small amount of salad oil, and then kneaded up without pasting the beans to obtain about 35 parts by weight of the desired product, an. Since the product has a satisfactory stability, mouth feel, taste, and flavor, and does not substantially exhibit syneresis and excessive color upon baking, it can be arbitrarily used as a material for confectioneries such as a bean jam bun, "manju" (a kind of Japanese confectionery with bean jam), bean-jam-filled wafer, and ice cream/candy.

EXAMPLE B-11

Bread

One hundred parts by weight of wheat flour, two parts by weight of a yeast, five parts by weight of sucrose, one part by weight of a powder containing cyclotetrasaccharide obtained by the method in Example A-1, and 0.1 part by weight of a yeast food, were kneaded with water in a usual manner, fermented at 26° C. for two hours, aged for 30 min, and then baked up. The product is a high quality bread having satisfactory color and texture, and adequate elasticity and mild sweetness.

EXAMPLE B-12

Ham

To one thousand parts by weight of ham meat slices were added and ground to homogeneity 15 parts by weight of salt and three parts by weight of potassium nitrate, and the resultant slices were piled and allowed to stand over a day and night in a cold-storage room. Thereafter, the resultant slices were first soaked for seven days in a cold-storage room in a salt solution consisting of 500 parts by weight of water, 100 parts by weight of salt, three parts by weight potassium nitrate, 40 parts by weight of a powder containing cyclotetrasaccharide, penta- or hexa-hydrate, obtained by the method in Example A-5, and an adequate amount of a spice, then washed with cold water in a usual manner, tied up with a string, smoked, cooked, cooled, and packaged to obtain the desired product.

The product is a high quality ham having a satisfactory hue, flavor, and taste.

EXAMPLE B-13

Powdery Peptide

One part by weight of 40% of "HINUTE S", a peptide solution of edible soy beans commercialized by Fuji Oil Co., Ltd., Tokyo, Japan, was mixed with two parts by weight of a powder containing cyclotetrasaccharide, hepta- or hexa-hydrate, obtained by the method in Example A-6, and the resultant mixture was placed in a plastic vessel, dried in vacuo at 50° C., and pulverized to obtain a powdery peptide. The product having a satisfactory flavor and taste can be arbitrary used as a material for confectioneries such as premixes, sherbets and ice creams, as well as a substantially non-digestible edible fiber and a material for controlling intestinal conditions which are used for fluid diets for oral administration and intubation feeding.

EXAMPLE B-14

Powdery Egg Yolk

Egg yolks prepared from fresh eggs were sterilized at 60–64° C. by a plate heater, and one part by weight of the resultant liquid was mixed with four parts by weight of a powder containing anhydrous crystalline cyclotetrasaccharide powder, obtained in accordance with the method in Experiment 25. The resultant mixture was transferred to a vessel and allowed to stand overnight to form a block while the cyclotetrasaccharide was allowing to convert into crystalline cyclotetrasaccharide, hepta- or hexa-hydrate. The block thus obtained was pulverized by a cutter into a powdery egg yolk.

The product can be arbitrary used as a material for low caloric confectioneries for premixes, sherbets, ice creams, and emulsifiers, as well as a substantially non-digestible edible fiber and a material for controlling intestinal conditions which are used for fluid diets for oral administration and intubation feeding. Also the product can be arbitrarily used as a skin-beautifying agent, hair restorer, etc.

EXAMPLE B-15

Bath Salt

One part by weight of a peel juice of "yuzu" (a Chinese lemon) was admixed with 10 parts by weight of a powder containing anhydrous crystalline cyclotetrasaccharide obtained in accordance with the method in Experiment 25, followed by crystallizing to form crystalline cyclotetrasaccharide, hepta- or hexa-hydrate, ageing the formed crystal, and pulverizing the aged crystal to obtain a powder of crystalline cyclotetrasaccharide, hepta- or hexa-hydrate, containing a yuzu peel extract.

A bath salt was obtained by mixing five parts by weight of the above powder with 90 parts by weight of grilled salt, two parts by weight of hydrous crystalline trehalose, one part by weight of silicic anhydride, and 0.5 part by weight of "αG HESPERIDIN", α-glucosyl hesperidin commercialized by Hayashibara Shoji, Inc., Okayama, Japan.

The product is a high quality bath salt enriched with yuzu flavor and used by diluting in hot water by 100–10,000 folds, and it moisturizes and smooths the skin and does not make one feel cold after taking a bath therewith.

EXAMPLE B-16

Cosmetic Cream

Two parts by weight of polyoxyethylene glycol monostearate, five parts by weight of glyceryl monostearate, self-emulsifying, two parts by weight of a powder of crystalline cyclotetrasaccharide, hepta- or hexa-hydrate, obtained by the method in Example A-8, one part by weight of "αG RUTIN", α-glucosyl rutin commercialized by Hayashibara Shoji, Inc., Okayama, Japan, one part by weight of liquid petrolatum, 10 parts by weight of glyceryl tri-2-ethylhexanoate, and an adequate amount of an antiseptic were dissolved by heating in a usual manner. The resultant solution was admixed with two parts by weight of L-lactic acid, five parts by weight of 1,3-butylene glycol, and 66 parts by weight of refined water, and the resultant mixture was emulsified by a homogenizer and admixed with an adequate amount of a flavor while stirring to obtain a cosmetic cream. The product exhibits an antioxidant activity and has a relatively high stability, and these render it advantageously useful as a high quality sunscreen, skin-refining agent, and skin-whitening agent.

Example B-17

Toothpaste

A toothpaste was obtained by mixing 45 parts by weight of calcium secondary phosphate, 1.5 parts by weight of sodium lauryl sulfate, 25 parts by weight of glycerine, 0.5 part by weight of polyoxyethylene sorbitan laurate, 15 parts by weight of a syrup containing cyclotetrasaccharide obtained by the method in Example A-2, 0.02 part by weight of saccharine, 0.05 part by weight of an antiseptic, and 13 parts by weight of water. The product has an improved after taste and satisfactory feeling after use without lowering the washing power of the surfactant.

EXAMPLE B-18

Solid Preparation for Fluid Diet

One hundred parts by weight of a power of crystalline cyclotetrasaccharide, penta- or hexa-hydrate, obtained by the method in Example A-6, 200 parts by weight of hydrous crystalline trehalose, 200 parts by weight of high maltotetraose content powder, 270 parts by weight of an egg yolk powder, 209 parts by weight of a skim milk powder, 4.4 parts by weight of sodium chloride, 1.8 parts by weight of potassium chloride, four parts by weight of magnesium sulfate, 0.01 part by weight of thiamine, 0.1 part by weight of sodium L-ascorbate, 0.6 part by weight of vitamin E acetate, and 0.04 part by weight of nicotinamide were mixed. Twenty-five grams aliquots of the resulting composition were injected into moisture-proof laminated small bags which were then heat sealed to obtain the desired product.

The product is a fluid diet which is enriched with substantially non-digestible edible fiber due to cyclotetrasaccharide, and has a satisfactory intestinal-controlling action. One bag of the product is dissolved in about 150–300 ml of water into a fluid diet and arbitrarily used by administering orally or intubationally into nasal cavity, stomach, intestines, etc., to supplement energy to living bodies.

EXAMPLE B-19

Tablet

To 50 parts by weight of aspirin were sufficiently admixed with 14 parts by weight of a powder of crystalline cyclotetrasaccharide, penta- or hexa-hydrate, obtained by the method in Example A-7, and four parts by weight of corn starch. The resulting mixture was in a usual manner tabletted by a tabletting machine to obtain a tablet, 680 mg each, 5.25 mm in thickness.

The tablet, processed using the filler-imparting ability of cyclotetrasaccharide, has substantially no hygroscopicity, a sufficient physical strength, and a quite satisfactory degradability in water.

EXAMPLE B-20

Sugar Coated Tablet

A crude tablet as a core, 150 mg weight, was sugar coated with a first solution consisting of 40 parts by weight of a powder of crystalline cyclotetrasaccharide, penta- or hexa-hydrate, obtained by the method in Example A-7, two parts by weight of pullulan having an average molecular weight of 200,000, 30 parts by weight of water, 25 parts by weight of talc, and three parts by weight of titanium oxide until the total weight reached to about 230 mg. The resultant was then sugar coated with a second solution consisting of 65 parts by weight of a fresh preparation of the same powder of crystalline cyclotetrasaccharide, penta- or hexa-hydrate, one part by weight of pullulan, and 34 parts by weight of water, and glossed with a liquid wax to obtain a sugar coated tablet having a satisfactory gloss and appearance. The product has a relatively high shock tolerance and retains its high quality for a relatively-long period of time.

Example B-21

Ointment for Treating Trauma

To 100 parts by weight of a powder of crystalline cyclotetrasaccharide, penta- or hexa-hydrate, obtained by the method in Example A-7, and 300 parts by weight of maltose was added 50 parts by weight of methanol dissolving three parts by weight of iodine, and further added 200 parts by weight of a 10% (w/v) aqueous pullulan solution to obtain the desired product with an adequate extensibility and adhesiveness. The product is a high-valued ointment in which the dispersion of iodine and methanol is well inhibited by cyclotetrasaccharide and is relatively low in change during storing.

Because the product exerts a sterilizing action by iodine and acts, based on maltose, as an energy-supplementing agent to living cells, it shortens the curing term and well cures the affected parts and surfaces.

INDUSTRIAL APPLICABILITY

As described above, the present invention relates to a novel α-isomaltosylglucosaccharide-forming enzyme, and their process and uses, more particularly, to a novel α-isornaltosylglucosaccharide-forming enzyme, process thereof, microorganisms producing the enzyme, α-glucosyl-transferring method using the enzyme, a method for forming α-isomaltosylglucosaccharide, a process for producing cyclotetrasaccharide having the structure of cyclo{→6) -α-D-glucopyranosyl- (1→3) -α-D-glucopyranosyl- (1→6) -α-D- glucopyranosyl- (1→3) -α-D-glucopyranosyl- (1→}, and a composition comprising the saccharide obtainable therewith. According to the present invention, an industrially useful cyclotetrasaccharide having the structure of cyclo{66) -α-D-glucopyranosyl- (163) -α-D-glucopyranosyl- (166) -α-D-glucopyranosyl- (163) -α-D-glucopyranosyl- (16} or a composition. comprising the same can be produced on an industrial scale and at a relatively low cost. Since these cyclotetrasaccharides and the saccharide comprising the same have substantially no or low reducibility, substantially do not cause the amino carbonyl reaction, substantially do not exhibit hygroscopicity, have easily handleability, have mild sweetness, adequate viscosity, moisture-retaining ability, inclusion ability, and substantially no digestibility, they can be advantageously used in a variety of compositions such as food products, cosmetics, pharmaceuticals as a sweetener, material for low caloric foods, taste-improving agent, flavor-improving ability, quality-improving agent, syneresis-preventing agent, stabilizer, filler, inclusion agent, and base for pulverization. The present invention, having these outstanding functions and effects, is a significantly important invention that greatly contributes to this art.

---

The invention claimed is:

1. A purified α-isomatosylglucosaccharide-forming enzyme which forms a saccharide having a glucose polymerization degree of at least three and having both the α-1,6 glucosidic linkage as a linkage at the non-reducing end and the α-1,4 glucosidic linkage other than the linkage at the non-reducing end, by catalyzing α-glucosyl-transfer from a saccharide having a glucose polymerization degree of at least two and having an α-glucosidic linkage at the non-reducing end; which enzyme comprises an amino acid sequence of SEQ ID NO:1, SEQ ID NO:11 or SEQ ID NO:18 as a partial amino acid sequence; said enzyme being incapable of forming dextran, said enzyme being inhibited by EDTA, and said enzyme activated by $Ca^{2+}$ and $Mn^{2+}$; thermal stability of said enzyme being improved by $Ca^{2+}$; and said enzyme having the following physicochemical properties:

a. Molecular weight
    About 136,000±20,000 Daltons on SDS-PAGE;
  b. Isoelectric point (pI)
    About 7.3±0.5 on isoelectrophoresis using ampholine;
  c. Optimum temperature
    (i) About 50° C. when incubated at a pH of 6.0 for 60 minutes;
    (ii) About 55° C. when incubated at a pH of 6.0 for 60 minutes in the presence of 1 mM $Ca^{2+}$;
  d. Optimum pH
    About 6.0 when incubated at 35° C. for 60 minutes;
  e. Thermal stability
    (i) Stable up to a temperature of about 45° C. when incubated at a pH of 6.0 for 60 minutes;
    (ii) Stable up to a temperature of about 50° C. when incubated at a pH of 6.0 for 60 minutes in the presence of 1 mM $Ca^{2+}$;
  f. pH stability
  Stable at pHs of about 5.0 to about 9.0 when incubated at 4° C. for 24 hours.

2. The α-isomaltosyl -glucosaccharide-forming enzyme of claim 1 which is obtained from a microorganism of the genus *Bacillus* selected from the group consisting of *Bacillus globisporus* N75, FERM BP-7591 and mutants thereof.

3. The α-isomatosylglucosaccharide-forming enzyme of claim 1, wherein said saccharide, having a glucose polymerization degree of at least two and having the α-1, 4 glucosidic linkage as a linkage at the non-reducing end, is one or more members selected from the group consisting of maltooligosaccharides, maltodextrins, amylodextrins, amyloses, amylopectins, soluble starches, liquefied starches, and glycogens.

* * * * *

SEQUENCE LISTING

<160> NUMBER OF SEQ ID NOS: 19

<210> SEQ ID NO 1
<211> LENGTH: 9
<212> TYPE: PRT
<213> ORGANISM: Bacillus globisporus

<400> SEQUENCE: 1

Tyr Val Ser Ser Leu Gly Asn Leu Ile
1               5

<210> SEQ ID NO 2
<211> LENGTH: 10
<212> TYPE: PRT
<213> ORGANISM: Bacillus globisporus

<400> SEQUENCE: 2

Ile Asp Gly Val Tyr His Ala Pro Asn Gly
1               5                   10

<210> SEQ ID NO 3
<211> LENGTH: 10
<212> TYPE: PRT
<213> ORGANISM: Bacillus globisporus

<400> SEQUENCE: 3

Ile Asp Gly Val Tyr His Ala Pro Tyr Gly
1               5                   10

<210> SEQ ID NO 4
<211> LENGTH: 8
<212> TYPE: PRT
<213> ORGANISM: Bacillus globisporus

<400> SEQUENCE: 4

Ile Asp Gly Val Tyr His Ala Pro
1               5

<210> SEQ ID NO 5
<211> LENGTH: 8
<212> TYPE: PRT
<213> ORGANISM: Bacillus globisporus

<400> SEQUENCE: 5

Asp Ala Ser Ala Asn Val Thr Thr
1               5

<210> SEQ ID NO 6
<211> LENGTH: 8
<212> TYPE: PRT

```
<213> ORGANISM: Bacillus globisporus

<400> SEQUENCE: 6

Trp Ser Leu Gly Phe Met Asn Phe
1               5

<210> SEQ ID NO 7
<211> LENGTH: 8
<212> TYPE: PRT
<213> ORGANISM: Bacillus globisporus

<400> SEQUENCE: 7

Asn Tyr Thr Asp Ala Trp Met Phe
1               5

<210> SEQ ID NO 8
<211> LENGTH: 8
<212> TYPE: PRT
<213> ORGANISM: Bacillus globisporus

<400> SEQUENCE: 8

Gly Asn Glu Met Arg Asn Gln Tyr
1               5

<210> SEQ ID NO 9
<211> LENGTH: 8
<212> TYPE: PRT
<213> ORGANISM: Bacillus globisporus

<400> SEQUENCE: 9

Ile Thr Thr Trp Pro Ile Glu Ser
1               5

<210> SEQ ID NO 10
<211> LENGTH: 8
<212> TYPE: PRT
<213> ORGANISM: Bacillus globisporus

<400> SEQUENCE: 10

Trp Ala Phe Gly Leu Trp Met Ser
1               5

<210> SEQ ID NO 11
<211> LENGTH: 9
<212> TYPE: PRT
<213> ORGANISM: Bacillus globisporus

<400> SEQUENCE: 11

His Val Ser Ala Leu Gly Asn Leu Leu
1               5

<210> SEQ ID NO 12
<211> LENGTH: 8
<212> TYPE: PRT
<213> ORGANISM: Bacillus globisporus

<400> SEQUENCE: 12

Asp Phe Ser Asn Asn Pro Thr Val
1               5

<210> SEQ ID NO 13
<211> LENGTH: 8
<212> TYPE: PRT
<213> ORGANISM: Bacillus globisporus
```

```
<400> SEQUENCE: 13

Tyr Thr Val Asn Ala Pro Ala Ala
1               5

<210> SEQ ID NO 14
<211> LENGTH: 8
<212> TYPE: PRT
<213> ORGANISM: Bacillus globisporus

<400> SEQUENCE: 14

Tyr Glu Ala Glu Ser Ala Glu Leu
1               5

<210> SEQ ID NO 15
<211> LENGTH: 6
<212> TYPE: PRT
<213> ORGANISM: Bacillus globisporus

<400> SEQUENCE: 15

Asn Trp Trp Met Ser Lys
1               5

<210> SEQ ID NO 16
<211> LENGTH: 8
<212> TYPE: PRT
<213> ORGANISM: Bacillus globisporus

<400> SEQUENCE: 16

Thr Asp Gly Gly Glu Met Val Trp
1               5

<210> SEQ ID NO 17
<211> LENGTH: 8
<212> TYPE: PRT
<213> ORGANISM: Bacillus globisporus

<400> SEQUENCE: 17

Asn Ile Tyr Leu Pro Gln Gly Asp
1               5

<210> SEQ ID NO 18
<211> LENGTH: 13
<212> TYPE: PRT
<213> ORGANISM: Arthrobacter globiformis

<400> SEQUENCE: 18

Ala Pro Leu Gly Val Gln Arg Ala Gln Phe Gln Ser Gly
1               5                   10

<210> SEQ ID NO 19
<211> LENGTH: 10
<212> TYPE: PRT
<213> ORGANISM: Arthrobacter ramosus

<400> SEQUENCE: 19

Asp Thr Leu Ser Gly Val Phe His Gly Pro
1               5                   10
```